US008932732B2

(12) United States Patent
Buesing et al.

(10) Patent No.: US 8,932,732 B2
(45) Date of Patent: Jan. 13, 2015

(54) MATERIALS FOR ORGANIC ELECTROLUMINESCENT DEVICES

(75) Inventors: Arne Buesing, Frankfurt am Main (DE); Philipp Stoessel, Frankfurt am Main (DE); Holger Heil, Darmstadt (DE)

(73) Assignee: Merck Patent GmbH (DE)

( * ) Notice: Subject to any disclaimer, the term of this patent is extended or adjusted under 35 U.S.C. 154(b) by 494 days.

(21) Appl. No.: 12/303,200

(22) PCT Filed: May 3, 2007

(86) PCT No.: PCT/EP2007/003886
§ 371 (c)(1),
(2), (4) Date: Dec. 2, 2008

(87) PCT Pub. No.: WO2007/140847
PCT Pub. Date: Dec. 13, 2007

(65) Prior Publication Data
US 2009/0184313 A1 Jul. 23, 2009

(30) Foreign Application Priority Data
Jun. 2, 2006 (DE) .......................... 10 2006 025 846

(51) Int. Cl.
*H01L 51/50* (2006.01)
*C07C 13/72* (2006.01)
*C07C 13/24* (2006.01)
*C07C 13/26* (2006.01)
*C07C 13/62* (2006.01)
*C07C 25/22* (2006.01)
*C07C 25/24* (2006.01)
*C07C 33/26* (2006.01)
*C07C 211/54* (2006.01)
*C07C 211/58* (2006.01)
*C07C 211/61* (2006.01)
*C07D 209/86* (2006.01)
*C07D 209/94* (2006.01)
*C07D 235/16* (2006.01)
*C07D 239/26* (2006.01)
*C07D 307/42* (2006.01)
*C07D 307/77* (2006.01)
*C07D 307/93* (2006.01)
*C07D 333/18* (2006.01)
*C07D 333/50* (2006.01)
*C07D 333/78* (2006.01)
*C07D 487/04* (2006.01)
*C07D 493/04* (2006.01)
*C07D 495/04* (2006.01)
*C07F 5/02* (2006.01)
*C09B 57/00* (2006.01)
(Continued)

(52) U.S. Cl.
CPC ................ *C07C 13/72* (2013.01); *C07C 13/24* (2013.01); *C07C 13/26* (2013.01); *C07C 13/62* (2013.01); *C07C 25/22* (2013.01); *C07C 25/24* (2013.01); *C07C 33/26* (2013.01); *C07C 211/54* (2013.01); *C07C 211/58* (2013.01); *C07C 211/61* (2013.01); *C07D 209/86* (2013.01); *C07D 209/94* (2013.01); *C07D 235/16* (2013.01); *C07D 239/26* (2013.01); *C07D 307/42* (2013.01); *C07D 307/77* (2013.01); *C07D 307/93* (2013.01); *C07D 333/18* (2013.01); *C07D 333/50* (2013.01); *C07D 333/78* (2013.01); *C07D 487/04* (2013.01); *C07D 493/04* (2013.01); *C07D 495/04* (2013.01); *C07F 5/027* (2013.01); *C09B 57/00* (2013.01); *C09B 69/109* (2013.01); *H01L 51/0056* (2013.01); *H01L 51/006* (2013.01); *C07C 2101/14* (2013.01); *C07C 2103/24* (2013.01); *C07C 2103/50* (2013.01); *C07C 2103/54* (2013.01); *C07C 2103/94* (2013.01); *H01L 51/5012* (2013.01); *H01L 51/5016* (2013.01); *H01L 51/5048* (2013.01); *Y02E 10/52* (2013.01); *Y02E 10/549* (2013.01); *Y10S 428/917* (2013.01)
USPC ........... 428/690; 428/917; 313/504; 313/506; 257/40; 257/E51.05; 257/E51.026; 257/E51.032; 548/304.1; 548/418; 548/440; 548/444; 546/18; 546/79; 546/81; 546/101

(58) Field of Classification Search
USPC .................. 428/690, 917; 313/504, 505, 506; 257/40, E51.05, E51.026, E51.032; 448/440, 340.4, 418
See application file for complete search history.

(56) References Cited

U.S. PATENT DOCUMENTS 5,942,340 A * 8/1999 Hu et al. ....................... 428/690
7,060,369 B2   6/2006 Stössel et al.
(Continued)

FOREIGN PATENT DOCUMENTS

EP    1217668 A1   6/2002
EP    1533290 A1   5/2005
(Continued)

OTHER PUBLICATIONS

Wang et, al., Synthesis of 6H-Indolo[2,3-b][1,6] naphthyridines and Related Compounds as the 5-Aza Analogues of Ellipticine Alkaloids, 2000, J. Org. Chem., vol. 65, pp. 7977-7983.*
(Continued)

*Primary Examiner* — Gregory Clark
(74) *Attorney, Agent, or Firm* — Drinker Biddle & Reath LLP

(57) ABSTRACT

The present invention relates to organic electroluminescent devices, in particular blue-emitting devices, in which compounds of the formulae (1) to (4) are used as host material or dopant in the emitting layer and/or as hole-transport material and/or as electron-transport material.

18 Claims, No Drawings

(51) Int. Cl.
*C09B 69/10* (2006.01)
*H01L 51/00* (2006.01)

(56) References Cited

U.S. PATENT DOCUMENTS

| 7,279,603 B2 | 10/2007 | Stössel et al. |
| 2004/0147742 A1 | 7/2004 | Wong et al. |
| 2005/0112404 A1 | 5/2005 | Hamada et al. |
| 2005/0236977 A1 | 10/2005 | Yamada et al. |

FOREIGN PATENT DOCUMENTS

| JP | 2002154993 A | 5/2002 |
| JP | 2005325097 A | 11/2005 |
| JP | 2006151935 A | 6/2006 |
| WO | WO-03/095445 A1 | 11/2003 |
| WO | WO-2004/061048 A1 | 7/2004 |

OTHER PUBLICATIONS

Osman et, al., Reactions Between Chloro-p-benzoquinones, 1957, J. Org. Chem., vol. 22, pp. 342-344.*

Ruiz, et al., "Overcrowded 5,10,15-Trisubstituted Derivatives: Synthesis of 5,10,15-Tri(fluorenylidene)truxene," *Eur. J. Org. Chem.*, (2004), pp. 858-866.

Lee, et al., "Stable styrylamine-doped blue organic electroluminescent device based on 2-methyl-9, 10-*di*(2-naphthyl)anthracene," *Applied Physics Letters*, (Oct. 11, 2004), vol. 85, No. 15, pp. 3301-3303.

Saint-Ruf, et al., "Further Studies in the Cyclodehydratino of Arylidene-α-tetralones," *J. Chem. Soc.*, (1960), pp. 2690-2694.

Wang, et al., "5,11-Dihydro-5,11-di-1-naphthylindolo[3,2-*b*]carbazole: Atropisomerism in a Novel Hole-Transport Molecule for Organic Light-Emitting Diodes," *J. Am. Chem. Soc.* (1999), vol. 121, pp. 5097-5098.

\* cited by examiner

MATERIALS FOR ORGANIC ELECTROLUMINESCENT DEVICES

CROSS-REFERENCE TO RELATED APPLICATIONS

Related Applications

This application is a national stage application (under 35 U.S.C. §371) of PCT/EP2007/003886, filed May 3, 2007, which claims benefit of German application 102006025846.0, filed Jun. 2, 2006.

BACKGROUND OF THE INVENTION

1. Field of Invention

The present invention relates to organic semiconductors and to the use thereof in organic electronic devices.

2. Description of the Prior Art

Organic semiconductors are being developed for a number of different applications which can be ascribed to the electronics industry in the broadest sense. The structure of organic electroluminescent devices (OLEDs) in which these organic semiconductors are employed as functional materials is described, for example, in U.S. Pat. No. 4,539,507, U.S. Pat. No. 5,151,629, EP 0676461 and WO 98/27136. However, these devices still exhibit considerable problems which require urgent improvement:

1. The compounds usually used do not have a sufficiently low LUMO (lowest unoccupied molecular orbital). Compounds having a relatively low LUMO are required for easier electron injection and thus for a reduction in the operating voltage.
2. In systems in accordance with the prior art, one or more dopants are usually used in a host material in the emitting layer. It would be sensible to have compounds which can be used as pure substance in the emitting layer since this represents a technical simplification in device production.
3. The lifetime of the organic electroluminescent device is still inadequate for long-lived, high-quality applications.
4. The thermal stability of many organic compounds currently used in organic electroluminescent devices is inadequate, meaning that considerable problems arise both in the purification of the material by bulk sublimation and also during application of the material by thermal evaporation. This applies, in particular, to compounds which contain styrylamino groups, as are frequently used as blue-emitting compounds.

For fluorescent OLEDs, principally condensed aromatic compounds, in particular anthracene or pyrene derivatives, are used in accordance with the prior art as host materials, especially for blue-emitting electroluminescent devices, for example 9,10-bis(2-naphthyl)anthracene (U.S. Pat. No. 5,935,721). WO 03/095445 and CN 1362464 disclose 9,10-bis(1-naphthyl)anthracene derivatives for use in OLEDs. Further anthracene derivatives are disclosed in WO 011076323, in WO 01/021729, in WO 04/013073, in WO 04/018588, in WO 03/087023 or in WO 04/018587. Host materials based on aryl-substituted pyrenes and chrysenes are disclosed in WO 04/016575. For high-quality applications, it is necessary to have available improved host materials.

As prior art in blue-emitting compounds, mention may be made of the use of arylvinylamines (for example WO 04/013073, WO 04/016575, WO 04/018587). However, these compounds are thermally unstable and cannot be evaporated without decomposition, which requires high technical complexity for the synthesis and OLED production and thus represents a technical disadvantage. A further disadvantage is the emission colour of these compounds: whereas dark-blue emission (CIE y coordinates in the range 0.15-0.18) is described in the prior art with these compounds, it has not been possible to reproduce these colour coordinates in simple devices in accordance with the prior art. By contrast, green-blue emission is obtained here. It is not evident how truly blue emission can be produced using these compounds. For high-quality applications, it is therefore necessary to have available improved emitters, particularly in relation to device and sublimation stability and emission colour.

In phosphorescent OLEDs, the matrix material used is frequently 4,4'-bis-(N-carbazolyl)biphenyl (CBP). The disadvantages are short lifetimes of the devices produced therewith and frequently high operating voltages, which result in low power efficiencies. In addition, CBP has an inadequately high glass transition temperature. Furthermore, it has been found that CBP is unsuitable for blue-emitting electroluminescent devices, which results in poor efficiency. In addition, the structure of the devices comprising CBP is complex since a hole-blocking layer and an electron-transport layer additionally have to be used. Improved triplet matrix materials based on keto compounds are described in WO 04/093207. However, toxic inorganic cyanides are disclosed for the synthesis of the best of the matrix materials described therein, and consequently the preparation of these materials is ecologically unacceptable. The glass transition temperature of other matrix materials described therein is still inadequate.

The electron-transport compound used in organic electroluminescent devices is usually $AlQ_3$ (aluminium trishydroxyquinolinate) (U.S. Pat. No. 4,539,507).

This has a number of disadvantages: it cannot be vapour-deposited without leaving a residue, since it partially decomposes at the sublimation temperature, which represents a major problem, in particular for production plants. A further disadvantage is the high hygroscopicity of $AlQ_3$, as is the low electron mobility, which results in higher voltages and thus in lower power efficiency. In order to prevent short-circuits in the display, it is desirable to increase the layer thickness; this is not possible with $AlQ_3$ owing to the low charge-carrier mobility and the resultant increase in voltage. Furthermore, the inherent colour of $AlQ_3$ (yellow in the solid), which can result in colour shifts, especially in blue OLEDs, due to reabsorption and weak re-emission, has proven very unfavourable. Blue OLEDs can only be produced here with considerable reductions in efficiency or colour location. In spite of the said disadvantages, $AlQ_3$ to date still represents the best compromise for the various requirements of an electron-transport material in OLEDs.

Thus, there continues to be a demand for improved materials, in particular host materials for blue-fluorescent emitters and triplet emitters, but also emitting compounds, in particular blue-emitting compounds, hole-transport materials and electron-transport materials, which are thermally stable, result in good efficiencies and at the same time in long lifetimes in organic electronic devices, give reproducible results in the production and operation of the device, are readily accessible synthetically and in high yields and have high thermal stability.

BRIEF SUMMARY OF THE INVENTION

Surprisingly, it has been found that compounds in which a phenylene group is linked to two naphthyl groups in the para-position, where the naphthyl groups may be linked to the phenylene group via the 1- or 2-position, and in which, in addition, at least one bridge exists in each case between the phenylene group and the two naphthyl groups, and heterocyclic derivatives of these compounds are very highly suitable for use in organic electroluminescent devices. These compounds have high thermal stability. Using these materials, an increase in the efficiency and lifetime of the organic electronic device compared with materials in accordance with the prior art is furthermore possible. Furthermore, these materials are very highly suitable for use in organic electronic devices since they have a very high glass transition temperature. The present invention therefore relates to these materials and to the use thereof in organic electronic devices, in particular in organic electroluminescent devices The invention relates to compounds of the formula (1) to formula (4)

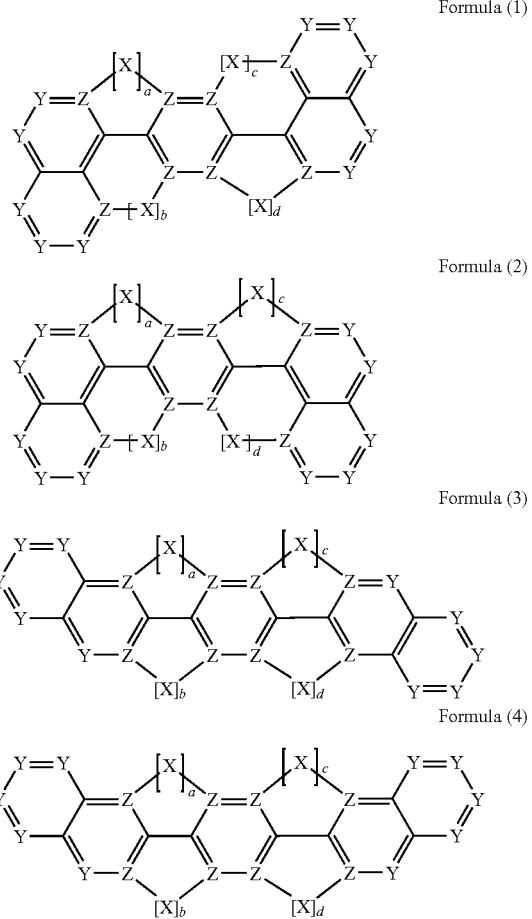

Formula (1)

Formula (2)

Formula (3)

Formula (4)

where the following applies to the symbols and indices:

Y is on each occurrence, identically or differently, $CR^1$ or N;

Z is equal to C if a bridge X is bonded to the group Z and is equal to Y if no bridge X is bonded to the group Z;

X is on each occurrence, identically or differently, a divalent bridge selected from $B(R^1)$, $C(R^1)_2$, $Si(R^1)_2$, C=O, C=$NR^1$, C=$C(R^1)_2$, O, S, S=O, $SO_2$, $N(R^1)$, $P(R^1)$ and P(=O)$R^1$;

$R^1$ is on each occurrence, identically or differently, H, F, Cl, Br, I, $N(Ar)_2$, C(=O)Ar, P(=O)$Ar_2$, S(=O)Ar, S(=O)$_2$Ar, $CR^2$=$CR^2$Ar, CN, $NO_2$, $Si(R^2)_3$, $B(OR^2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$ and in which one or more non-adjacent $CH_2$ groups may be replaced by $R^2C$=$CR^2$, C=C, $Si(R^2)_2$, $Ge(R^2)_2$, $Sn(R^2)_2$, C=O, C=S, C=Se, C=$NR^2$, P(=O)($R^2$), SO, $SO_2$, $NR^2$, O, S or $CONR^2$ and in which one or more H atoms may be replaced by F, Cl, Br, I, CN or $NO_2$, or an aromatic or heteroaromatic ring system having 5 to 40 aromatic ring atoms, which may in each case be substituted by one or more radicals $R^2$, or an aryloxy or heteroaryloxy group having 5 to 40 aromatic ring atoms, which may be substituted by one or more radicals $R^2$, or a combination of these systems; two or more adjacent substituents $R^1$ here may also form a mono- or polycyclic aliphatic or aromatic ring system with one another;

Ar is on each occurrence, identically or differently, an aromatic or heteroaromatic ring system having 5-30 aromatic ring atoms, which may be substituted by one or more non-aromatic radicals $R^1$; two radicals Ar here on the same nitrogen or phosphorus atom may also be linked to one another by a single bond or a bridge X;

$R^2$ is on each occurrence, identically or differently, H or an aliphatic, aromatic and/or heteroaromatic hydrocarbon radical having 1 to 20 C atoms, in which, in addition, H atoms may be replaced by F; two or more adjacent substituents $R^2$ here may also form a mono- or polycyclic aliphatic or aromatic ring system with one another;

a, b, c, d are on each occurrence, identically or differently, 0 or 1, with the proviso that a+b=1 or 2 and c+d=1 or 2, where a=0 and b=0 and c=0 and d=0 in each case means that the corresponding bridge X is not present;

with the exception of the following compounds:

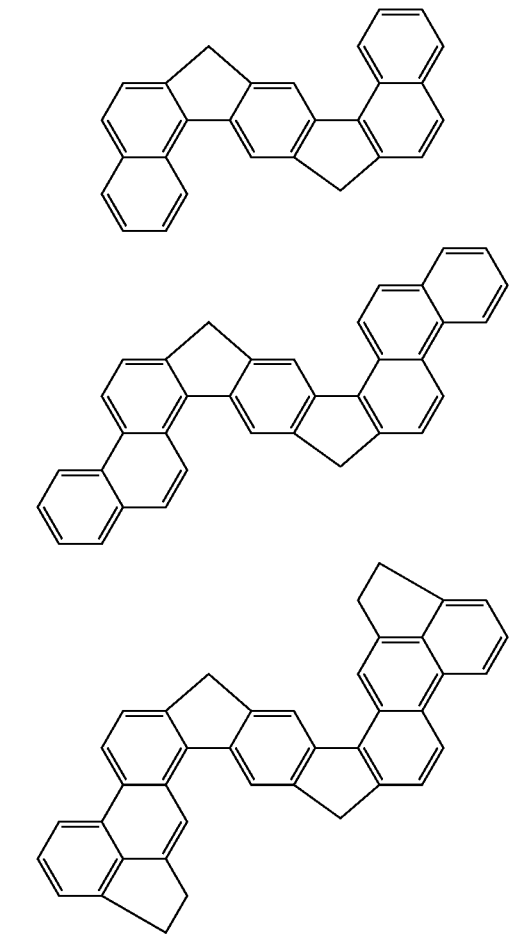

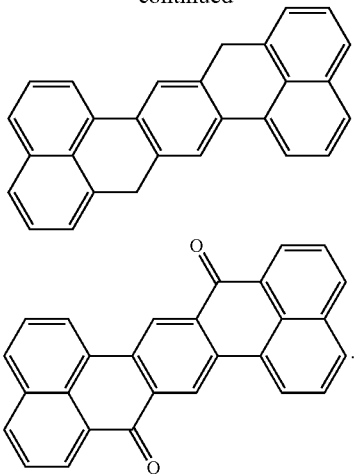

The compounds of the formula (1) to formula (4) preferably have a glass transition temperature $T_g$ of greater than 70° C., particularly preferably greater than 100° C., very particularly preferably greater than 130° C.

DETAILED DESCRIPTION OF THE INVENTION

For the purposes of this invention, adjacent radicals $R^1$ and $R^2$ are taken to mean radicals which are either bonded to the same carbon atom or to the same heteroatom or are bonded to adjacent carbon atoms or heteroatoms.

For the purposes of this invention, an aryl group contains 6 to 40 C atoms; for the purposes of this invention, a heteroaryl group contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a single aromatic ring, i.e. benzene, or a single heteroaromatic ring, for example pyridine, pyrimidine, thiophene, etc., or a condensed aryl or heteroaryl group, for example naphthalene, anthracene, pyrene, quinoline, isoquinoline, etc.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an $sp^3$-hybridised C, N or O atom.

Thus, for example, systems such as 9,9'-spirobifluorene, 9,9-diarylfluorene, triarylamine, diaryl ether, stilbene, etc., are also intended to be taken to mean aromatic ring systems for the purposes of this invention.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethyl hexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-40 aromatic ring atoms, which may also in each case be substituted by the above-mentioned radicals R and which may be linked to the aromatic or heteroaromatic ring system via any desired positions, is taken to mean, in particular, groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to structures of the formulae (1) to (4) in which a+b=1 and c+d=1.

Preference is given to the compounds of the formulae (1) to (4) selected from the structures of the formula (5), (6), (7), (8), (9), (10), (11), (12), (13), (14), (15) or (16)

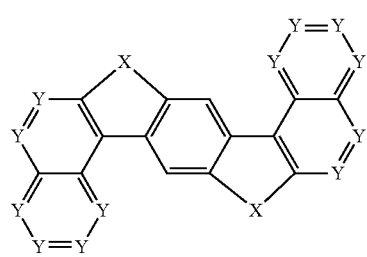

Formula (5)

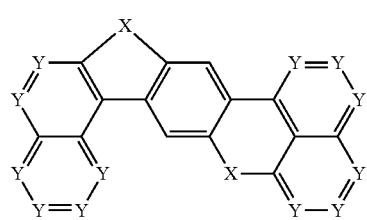

Formula (6)

Formula (7)
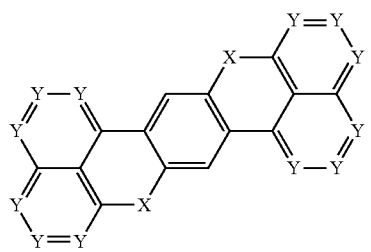

Formula (8)
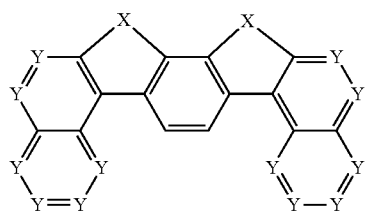

Formula (9)
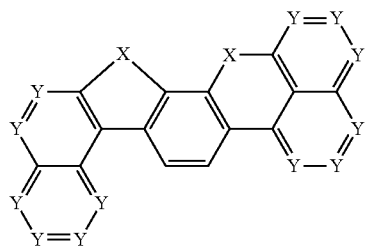

Formula (10)
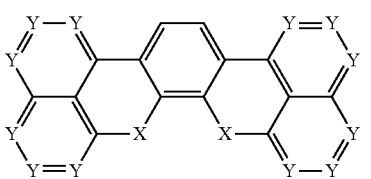

Formula (11)
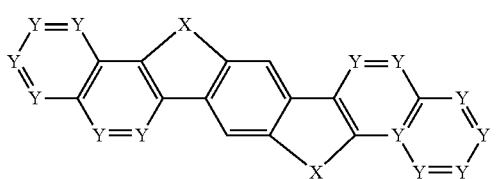

Formula (12)
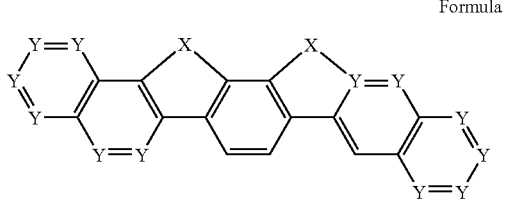

Formula (13)
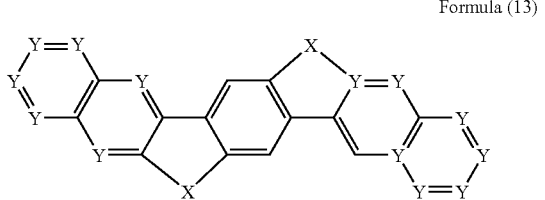

Formula (14)
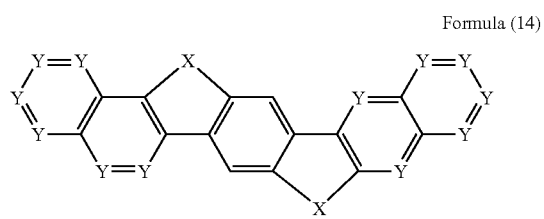

Formula (15)
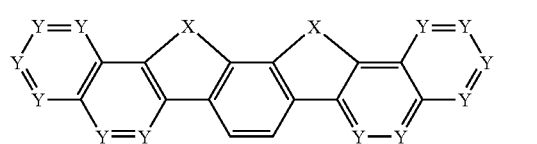

Formula (16)
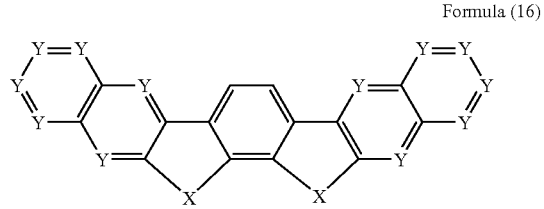

where the symbols X and Y have the same meaning as described above.

Preference is furthermore given to compounds of the formula (1) to formula (16) in which the symbol Y stands for nitrogen a total of 0, 1, 2, 3 or 4 times, where the other symbols Y stand for $CR^1$. Particular preference is given to compounds of the formula (1) to formula (16) in which the symbol Y stands for nitrogen a total of 0, 1 or 2 times. In a particularly preferred embodiment of the invention, the symbol Y stands for $CR^1$.

In a very particularly preferred embodiment, the structures of the formulae (1) to (4) are selected from the formulae (5a), (6a), (7a), (8a), (9a), (10a) and (11a)

Formula (5a)
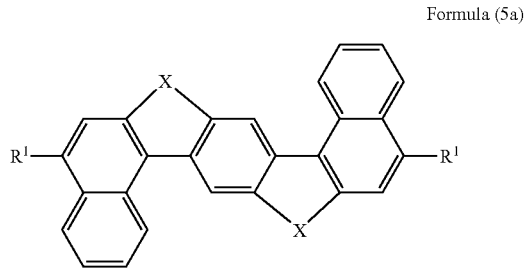

Formula (6a)
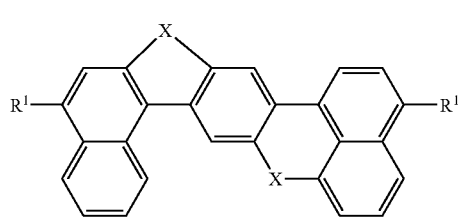

-continued

Formula (7a)
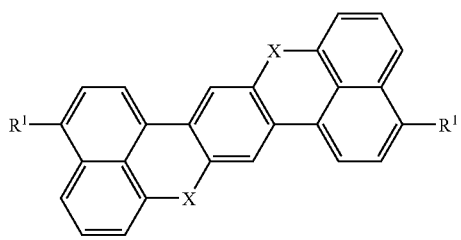

Formula (8a)
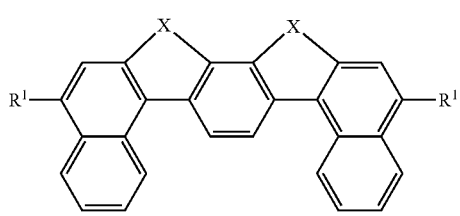

Formula (9a)
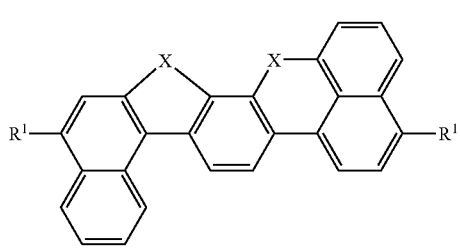

Formula (10a)
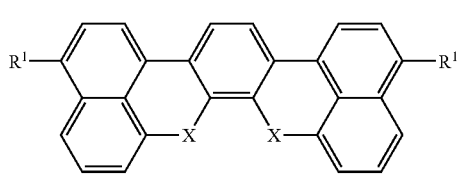

Formula (11a)
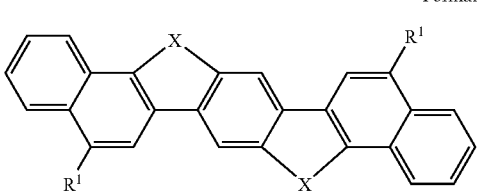

where the symbols X and $R^1$ have the same meaning as described above.

In the structures of the formulae (5a) to (11a), the two radicals $R^1$ are in each case particularly preferably other than hydrogen.

Preference is furthermore given to compounds of the formulae (1) to (16) and (5a) to (11a) in which the symbol $R^1$, identically or differently on each occurrence, stands for H, F, Br, C(=O)Ar, P(=O)Ar$_2$, CR$^2$=CR$^2$Ar, a straight-chain alkyl group having 1 to 5 C atoms or a branched alkyl group having 3 to 5 C atoms, in which one or more non-adjacent CH$_2$ groups may be replaced by —R$^2$C=CR$^2$—, —C≡C— or —O— and in which one or more H atoms may be replaced by F, or an aryl group having 6 to 16 C atoms or a heteroaryl group having 2 to 16 C atoms or a spirobifluorene group, each of which may be substituted by one or more radicals $R^2$, or a combination of two or three of these systems. Particularly preferred radicals $R^1$ are, identically or differently on each occurrence, H, F, Br, C(=O)Ar, P(=O)Ar$_2$, methyl, ethyl, isopropyl, tert-butyl, in which one or more H atoms may be replaced by F, or an aryl group having 6 to 14 C atoms or a spirobifluorene group, each of which may be substituted by one or more radicals $R^2$, or a combination of two of these systems.

On incorporation into polymers, oligomers or dendrimers and in the case of compounds which are processed from solution, linear or branched alkyl chains having up to 10 C atoms are also preferred. Bromine as substituent is particularly preferred for use of this compound as intermediate for the preparation of other compounds according to the invention or for use as monomer for the preparation of polymers.

Preference is furthermore given to compounds of the formulae (1) to (16) and (5a) to (11a) in which at least one symbol $R^1$ stands for a group N(Ar)$_2$ of the formula (17) or (18)

Formula (17)
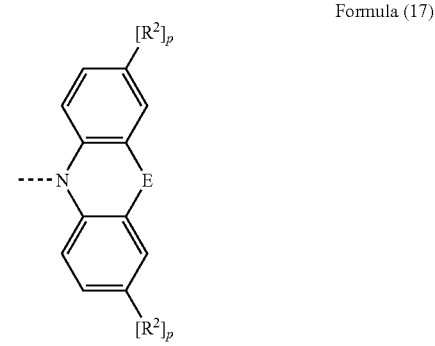

Formula (18)

where $R^2$ has the above-mentioned meaning and furthermore:
E stands for a single bond, O, S, N(R$^2$) or C(R$^2$)$_2$;
Ar$^1$ is, identically or differently on each occurrence, an aryl or heteroaryl group having 5 to 20 aromatic ring atoms or a triarylamine group having 15 to 30 aromatic ring atoms, each of which may be substituted by one or more radicals $R^2$, preferably an aryl or heteroaryl group having 6 to 14 aromatic ring atoms or a triarylamine group having 18 to 22 aromatic ring atoms, each of which may be substituted by one or more radicals $R^2$;
p is on each occurrence, identically or differently, 0 or 1.

Particular preference is given to compounds of the above-mentioned formulae (5a) to (11a) in which the radicals $R^1$ stand for a group of the formula (17) or formula (18).

Ar$^1$ particularly preferably stands, identically or differently, for phenyl, ortho-, meta- or para-tolyl, para-fluorophenyl, 1-naphthyl, 2-naphthyl, triphenylamine, naphthyidiphenylamine or dinaphthylphenylamine.

Preference is furthermore given to compounds of the formulae (1) to (16) and (5a) to (11a) in which the symbols X are on each occurrence, identically or differently, a divalent bridge selected from C(R$^1$)$_2$, C=O, C=NR$^1$, O, S, S=O, SO$_2$, N(R$^1$), P(R$^1$) and P(=O)R$^1$. Particular preference is given to compounds of the formulae (1) to (16) and (5a) to (11a) in which the symbols X on each occurrence, identically or differently, are selected from C(R$^1$)$_2$, N(R$^1$), P(R$^1$) and P(=O)(R$^1$), very particularly preferably C(R$^1$)$_2$ and N(R$^1$), in particular C(R$^1$)$_2$. It should again explicitly be pointed out here that a plurality of adjacent radicals $R^1$ may likewise form an aromatic or aliphatic ring system with one another here. If a plurality of radicals $R^1$ on a group C(R$^1$)$_2$ form a ring system with one another, this results in spiro structures. The formation of Spiro structures of this type by the formation of ring systems between two groups $R^1$ on C(R$^1$)$_2$ is a further preferred embodiment of the invention. This applies, in particular, if R¹ stands for a substituted or unsubstituted phenyl group, and the two phenyl groups form a ring system together with the bridge X.

Preferred radicals R¹ which are bonded to the bridges X are identical or different and are selected from H, straight-chain alkyl groups having 1 to 5 C atoms or branched alkyl groups having 3 to 5 C atoms, in which in each case one or more non-adjacent CH₂ groups may be replaced by —R²C═CR²—, —C≡C— or —O— and in which one or more H atoms may be replaced by F, or aryl groups having 6 to 16 C atoms or heteroaryl groups having 2 to 16 C atoms, each of which may be substituted by one or more radicals R², or a combination of two or three of these systems; two of the radicals R¹ which are bonded to the same bridge atom here may also form a ring system with one another. Particularly preferred radicals R¹ which are bonded to the bridges X are identical or different and are selected from methyl, ethyl, isopropyl, tert-butyl, in which in each case one or more H atoms may be replaced by F, or aryl groups having 6 to 14 C atoms, which may be substituted by one or more radicals R², or a combination of two of these systems; two of the radicals R¹ which are bonded to the same bridge atom here may also form a ring system with one another. On incorporation into polymers, oligomers or dendrimers and in the case of compounds which are processed from solution, linear or branched alkyl chains having up to 10 C atoms are also preferred.

Preference is furthermore given to symmetrical and symmetrically substituted compounds, i.e. compounds in which the symbols X are identical. The substituents R¹ in the structures of the formulae (5a) to (11a) are furthermore preferably selected identically.

Examples of preferred compounds of the formula (1) to formula (16) and (5a) to (11a) are structures (1) to (132) depicted below.

(1)

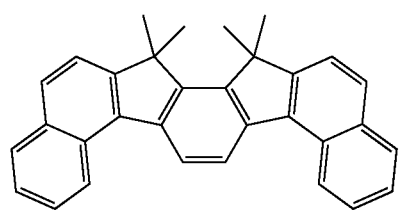

(2)

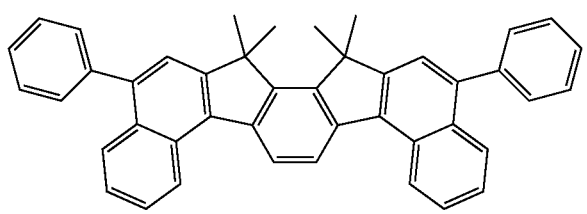

(3)

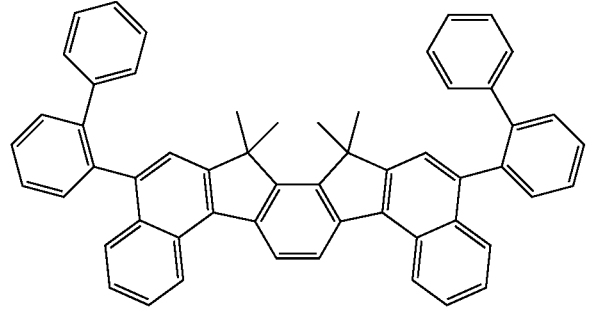

(4)

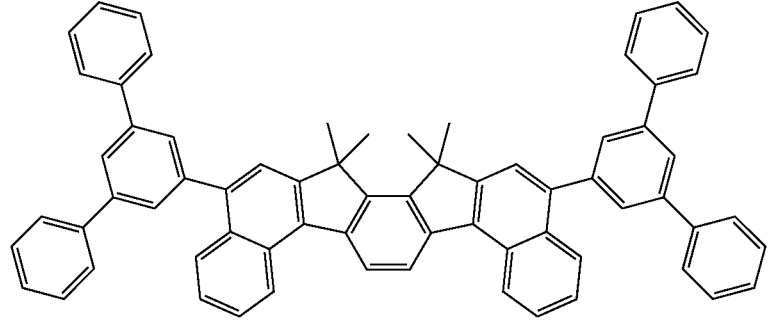

(5)

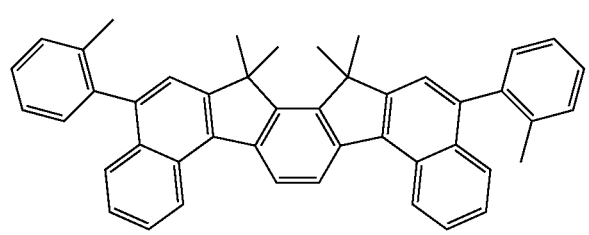

(6)

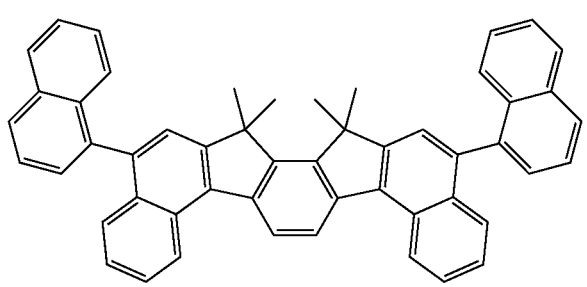

-continued
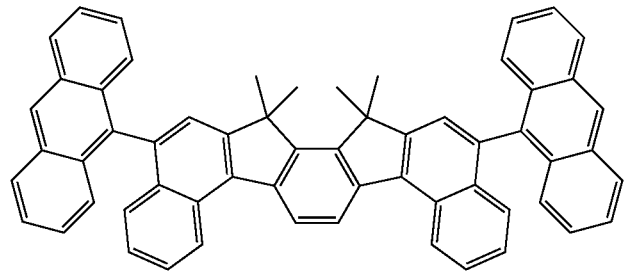
(7)
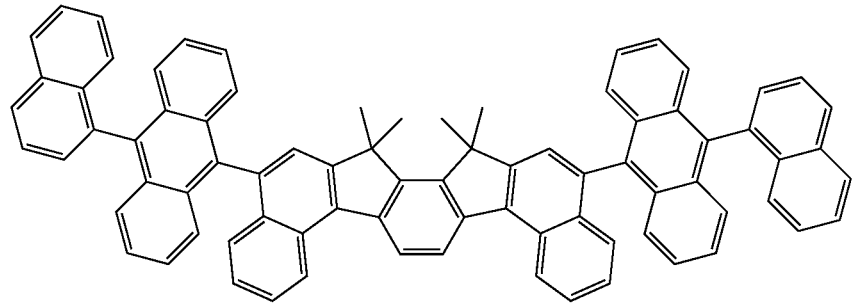
(8)
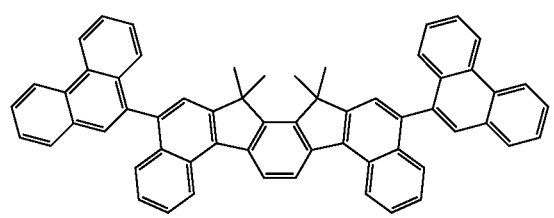
(9)
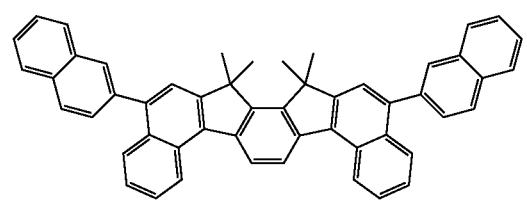
(10)
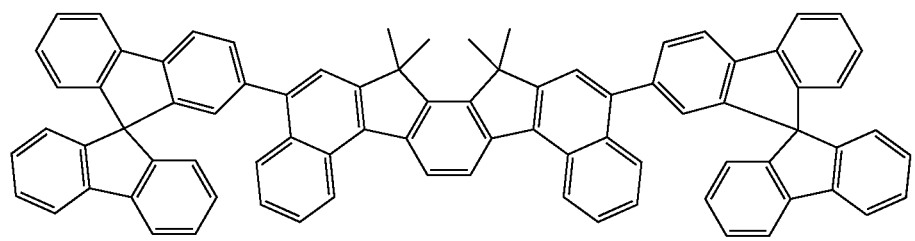
(11)
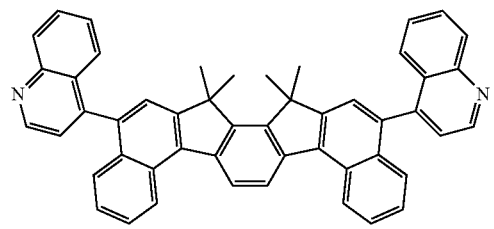
(12)
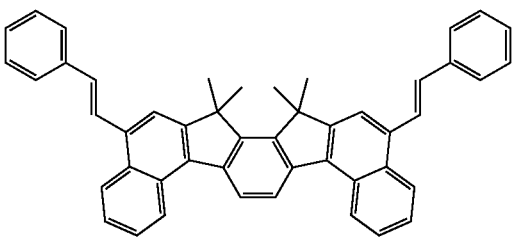
(13)
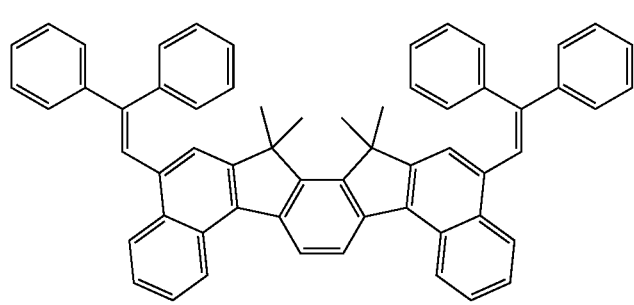
(14)

(15)
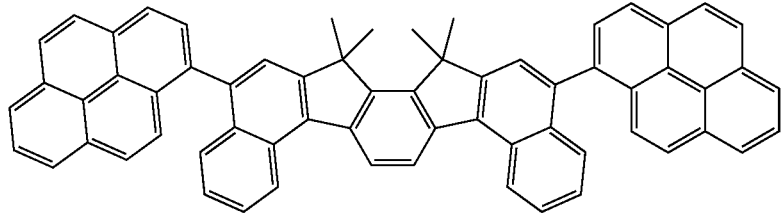
(16)
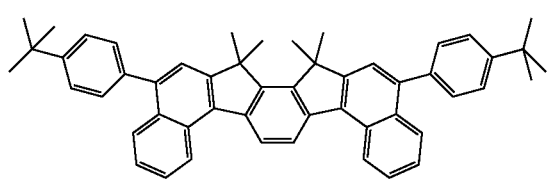
(17)
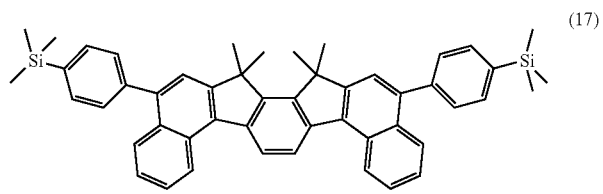
(18)
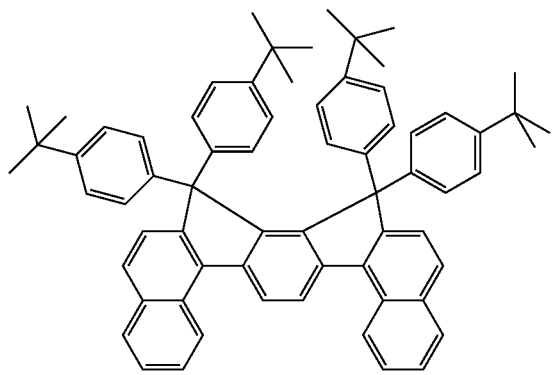
(19)
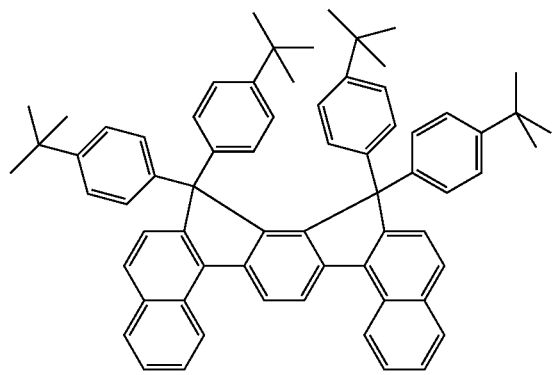
(20)
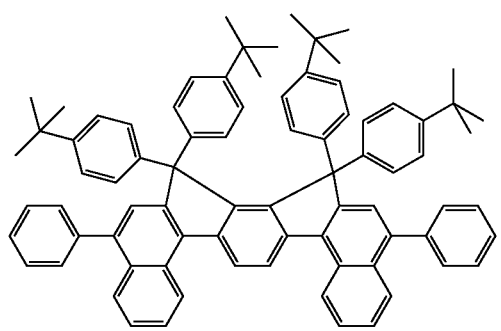
(21)
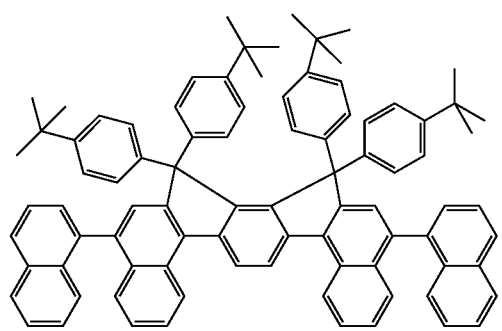
(22)
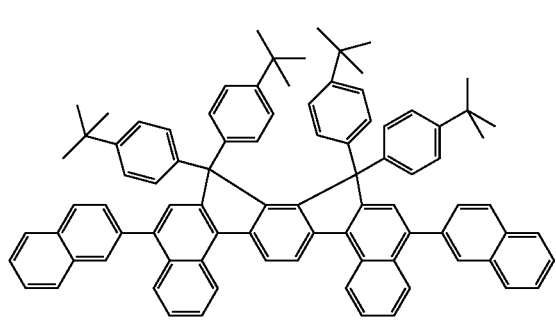
(23)
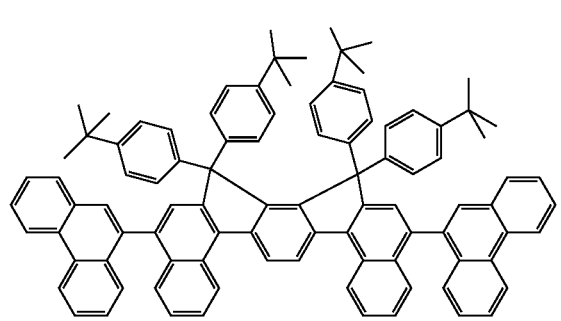

(24)
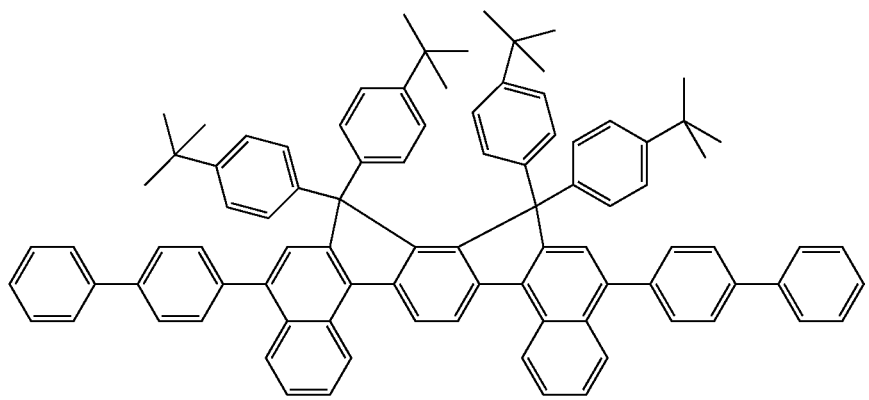
(25)
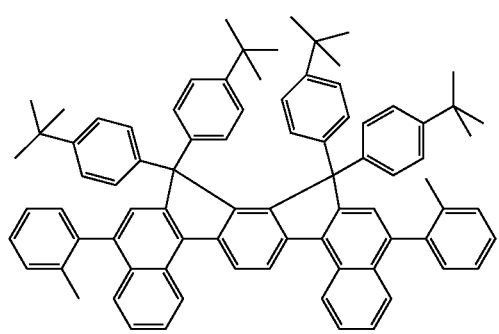
(26)
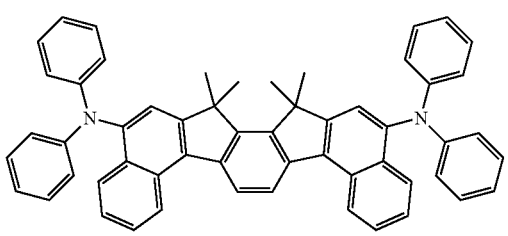
(27)
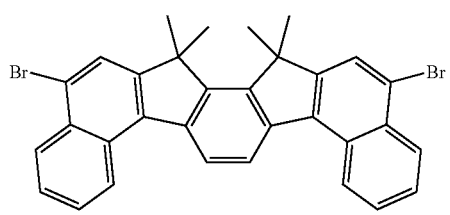
(28)
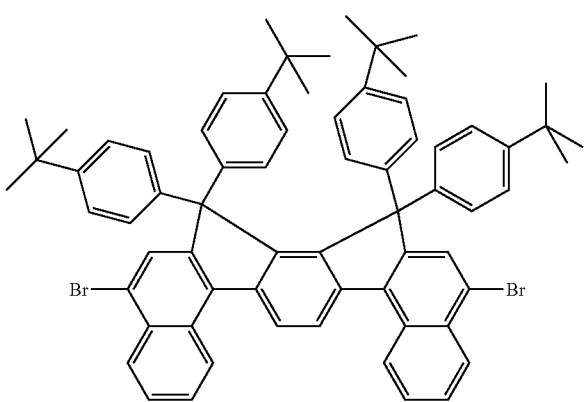
(29)
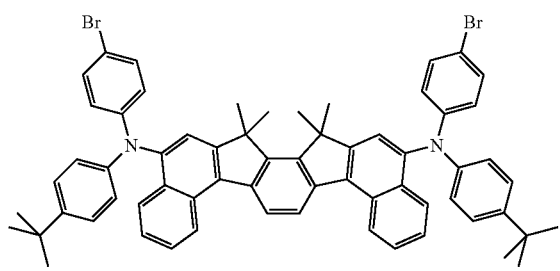
(30)
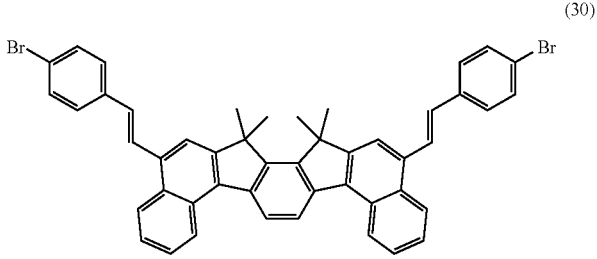

-continued
(31)
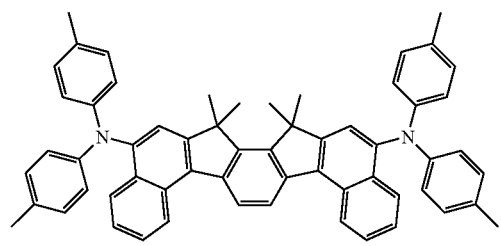
(32)
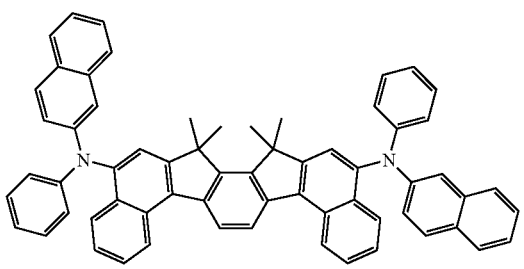
(33)
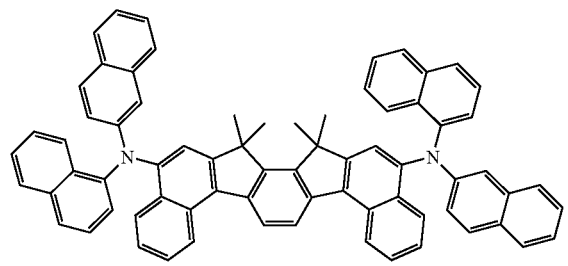
(34)
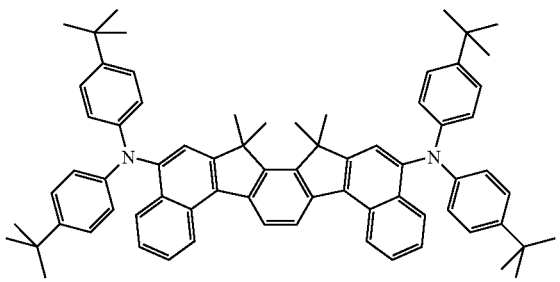
(35)
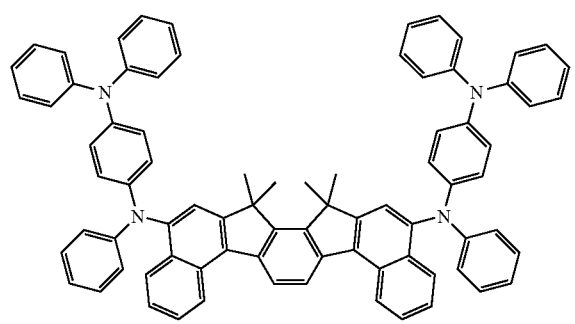
(36)
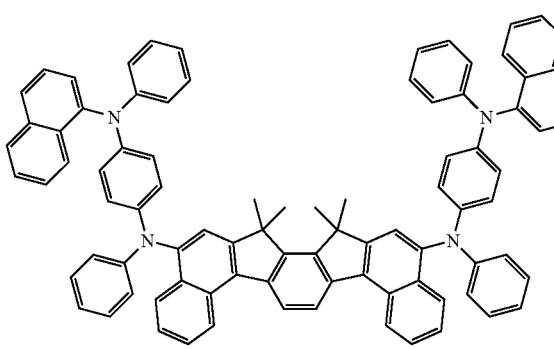
(37)
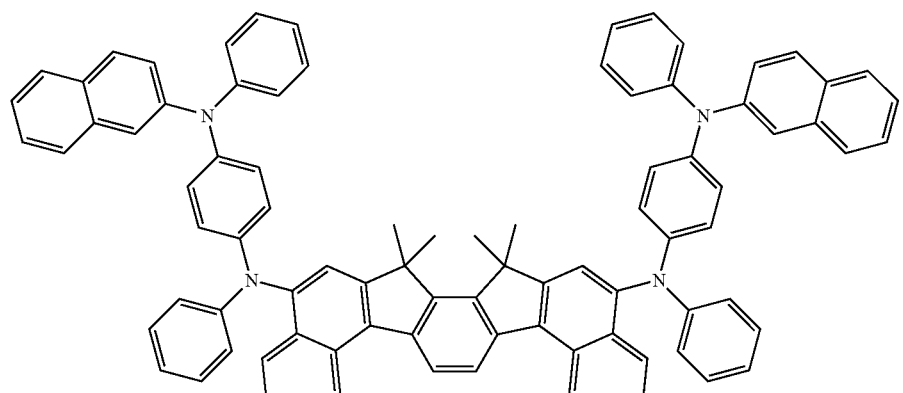
(38)
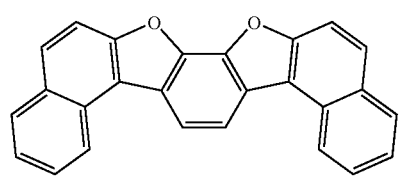
(39)
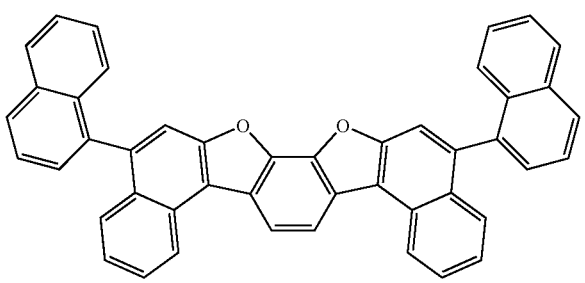

-continued
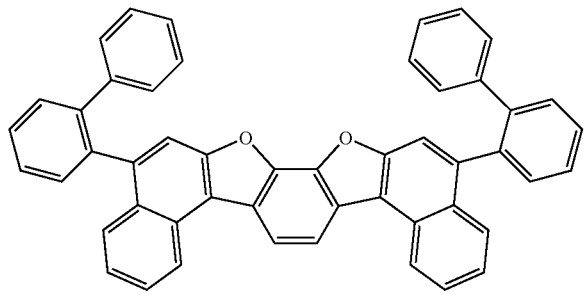
(40)
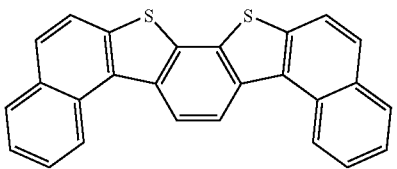
(41)
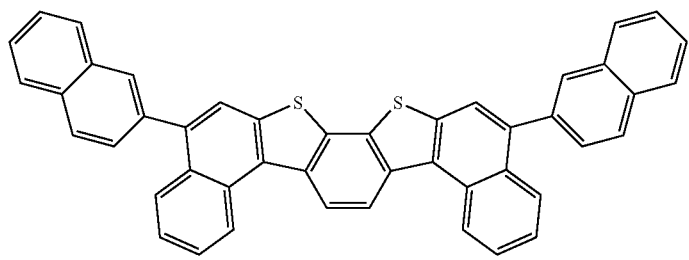
(42)
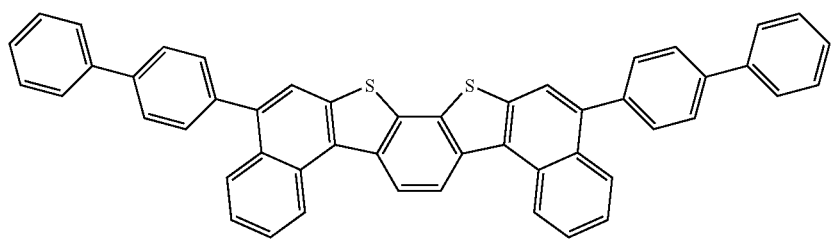
(43)
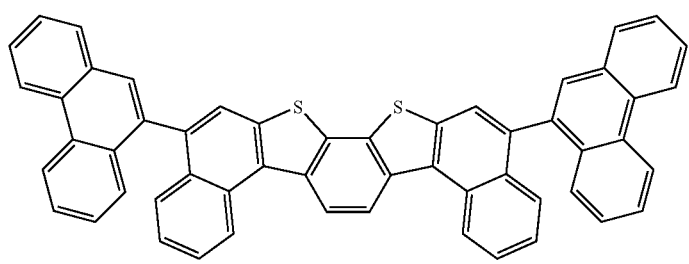
(44)
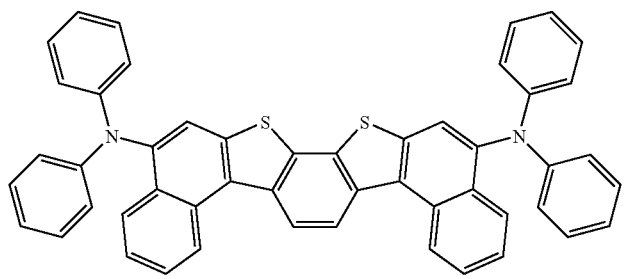
(45)
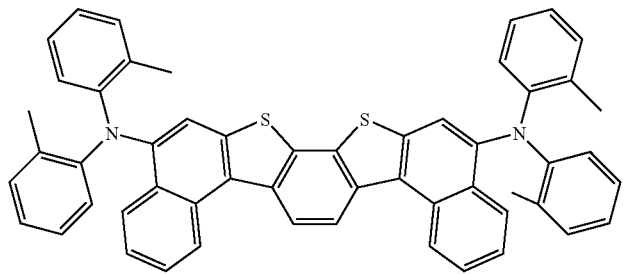
(46)

-continued
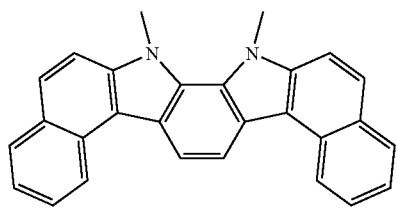
(47)
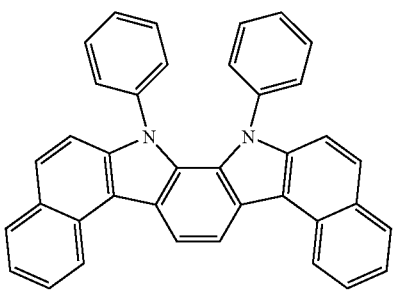
(48)
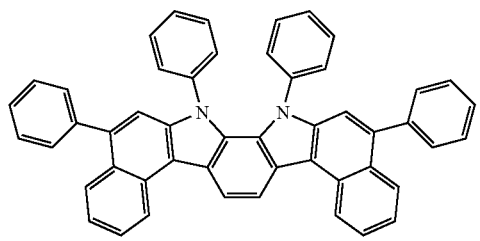
(49)
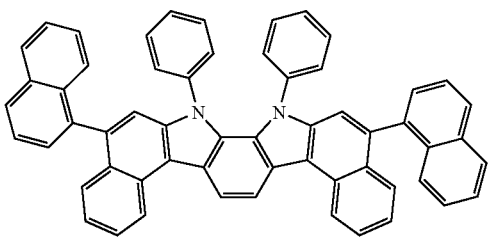
(50)
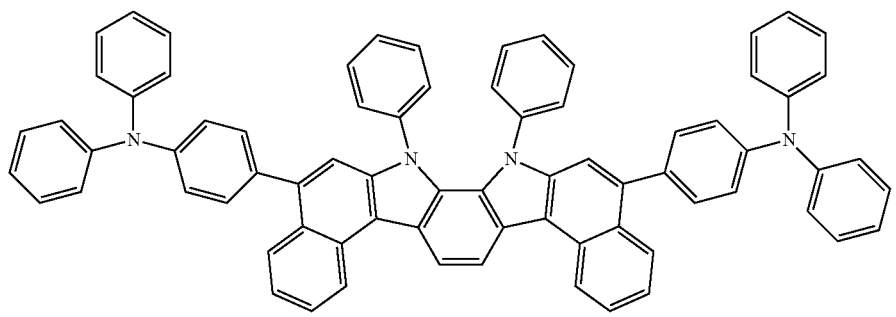
(51)
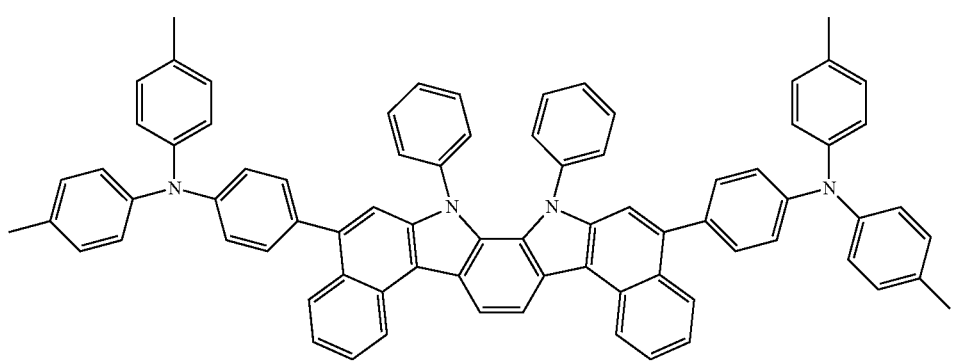
(52)
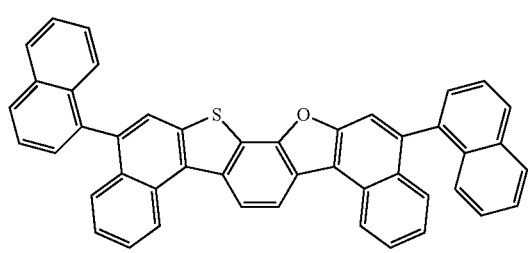
(53)
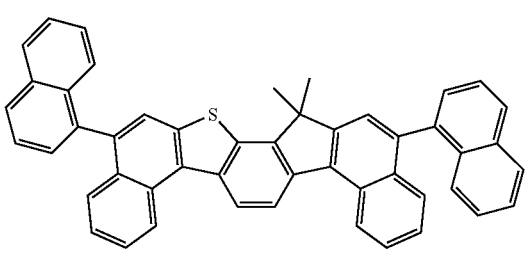
(54)

-continued
(55)
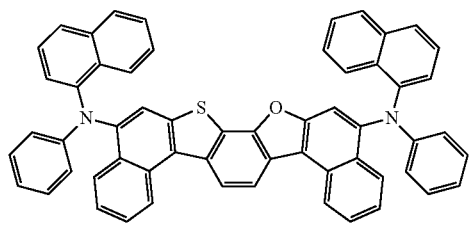
(56)
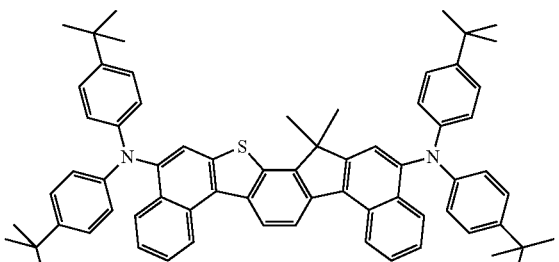
(57)
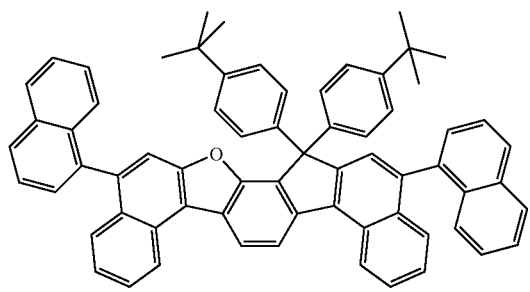
(58)
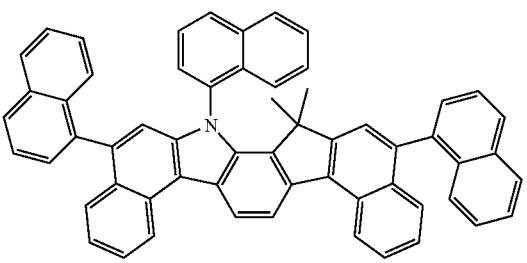
(59)
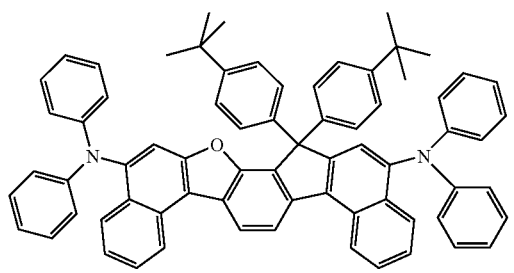
(60)
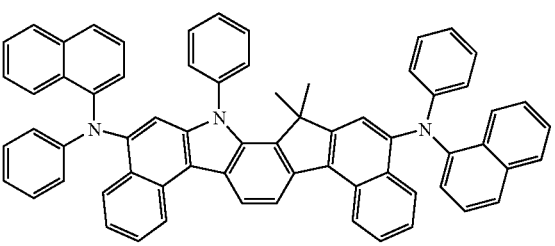
(61)
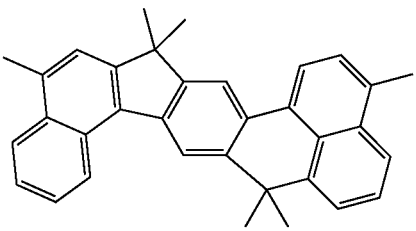
(62)
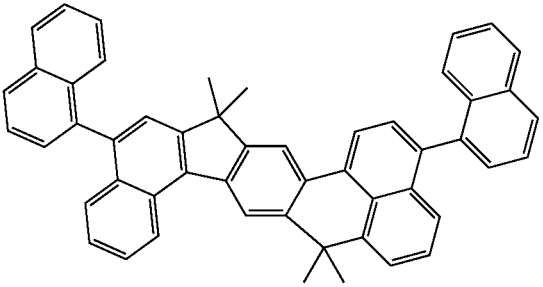
(63)
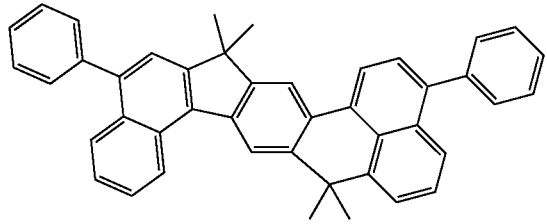
(64)
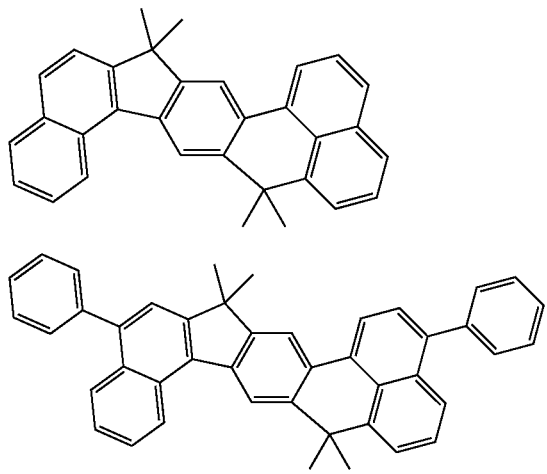
(65)
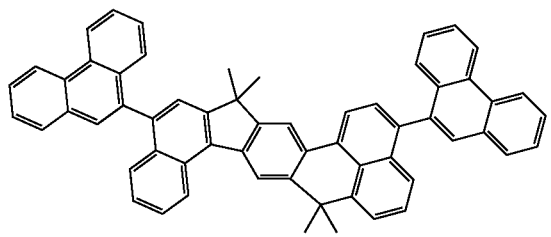
(66)
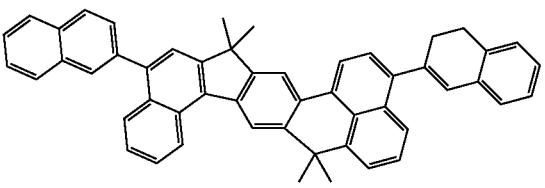

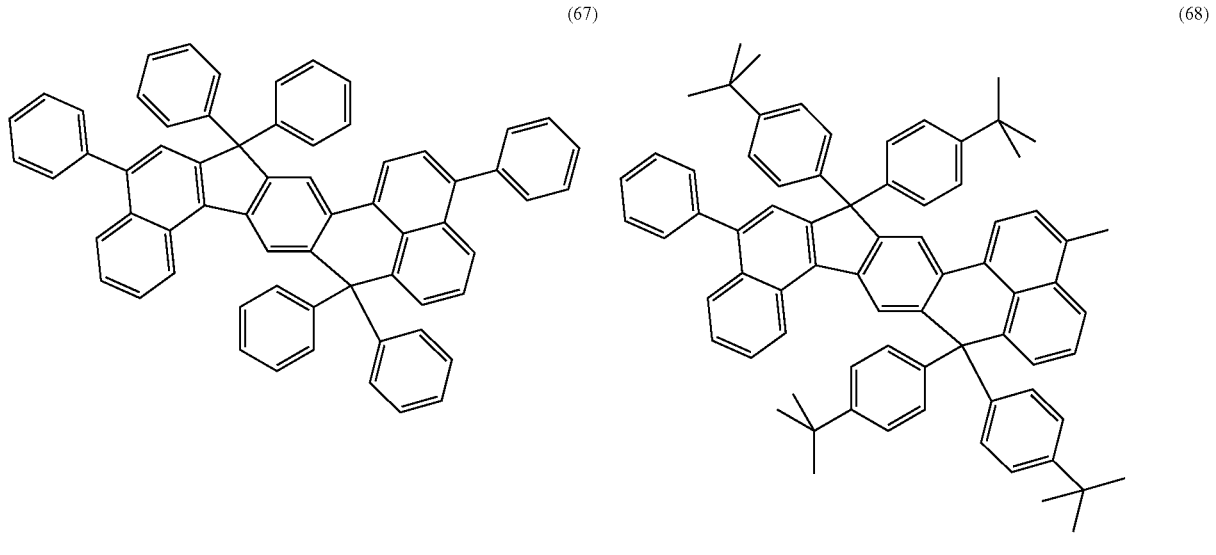
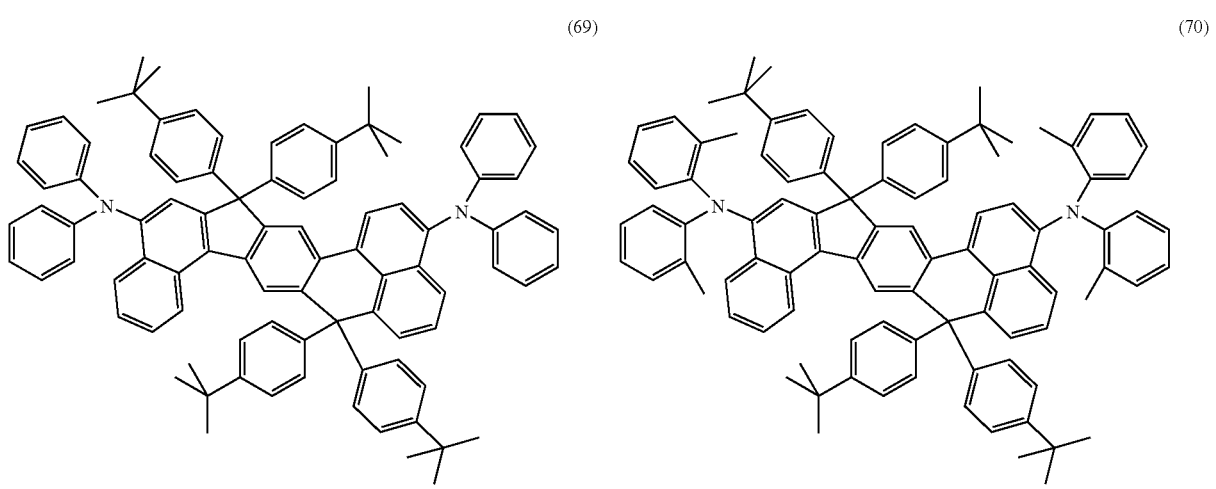
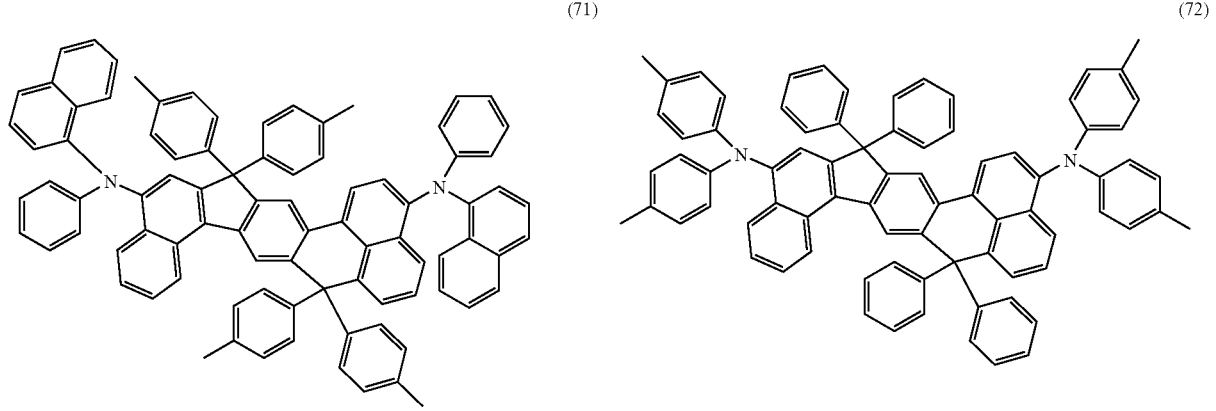

(73)
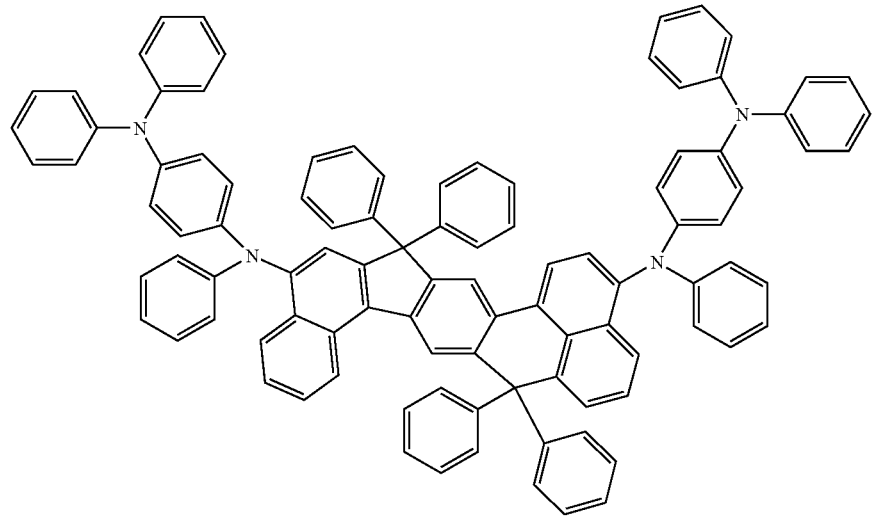
(74)
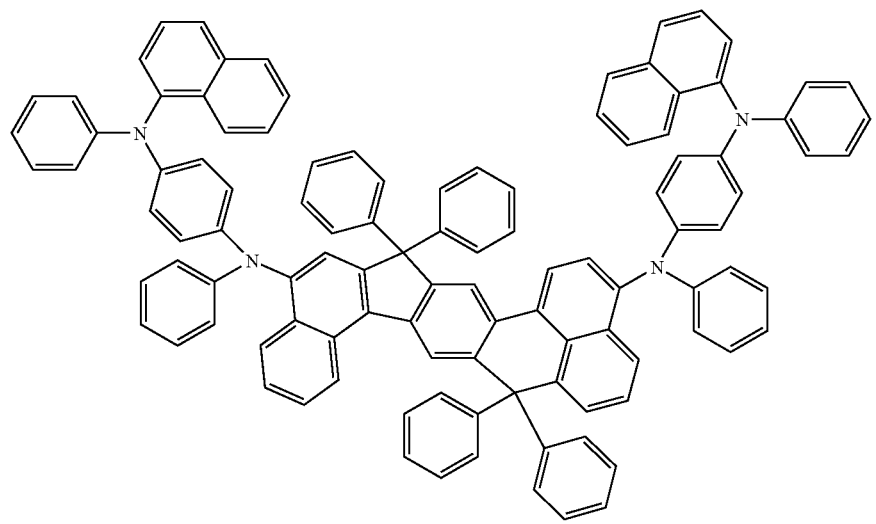
(75)
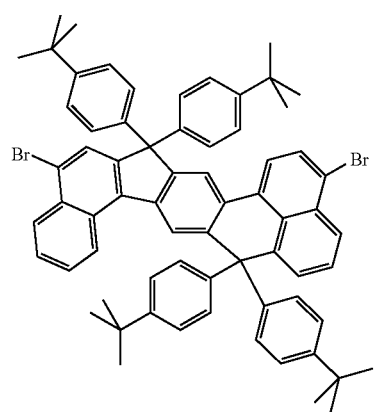
(76)
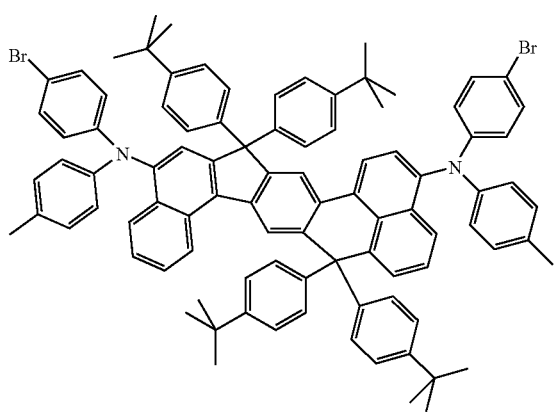

-continued
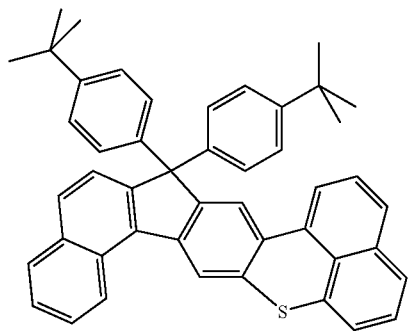
(77)
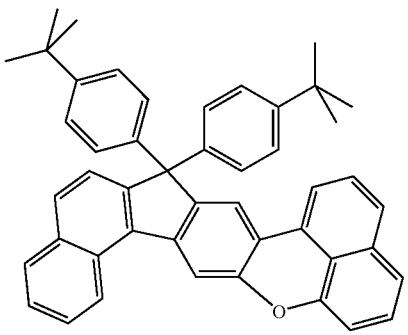
(78)
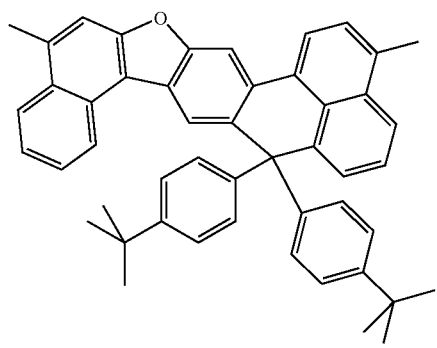
(79)
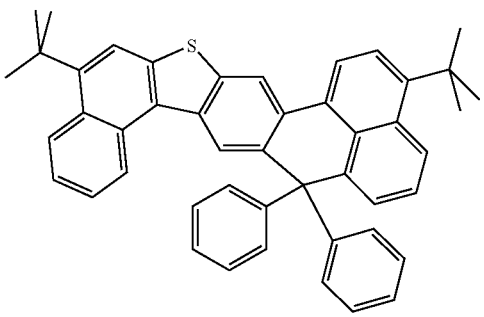
(80)
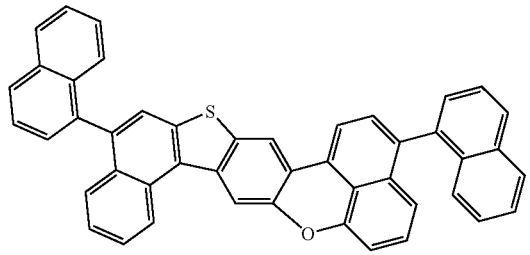
(81)
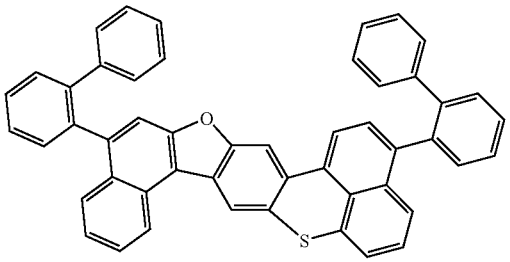
(82)
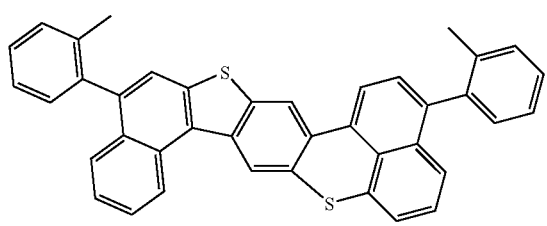
(83)
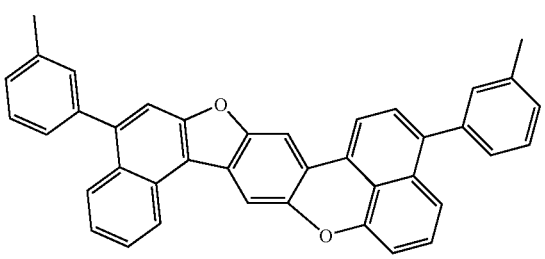
(84)
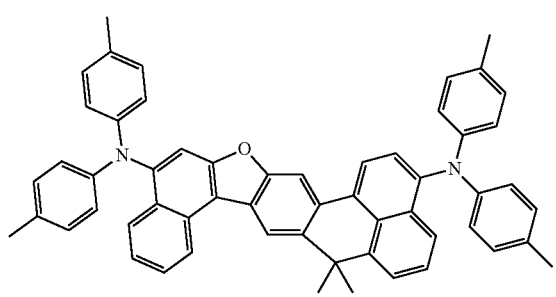
(85)
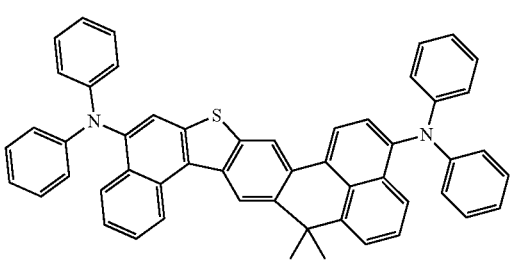
(86)

-continued
(87)
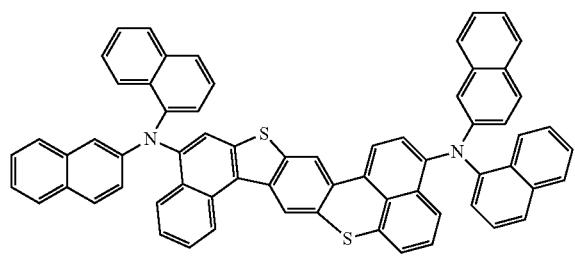
(88)
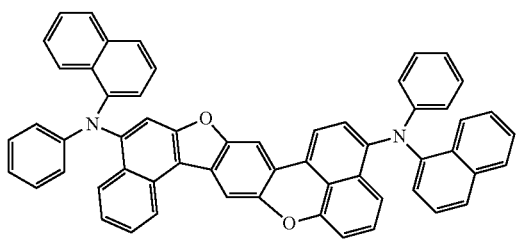
(89)
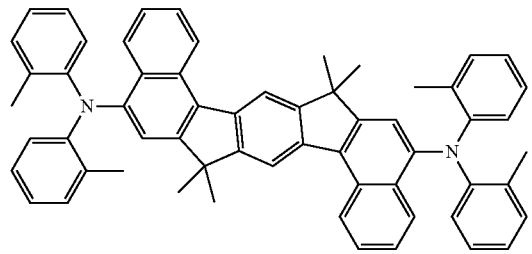
(90)
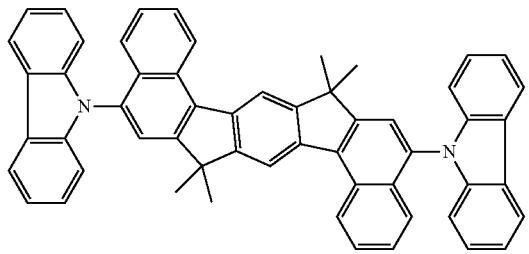
(91)
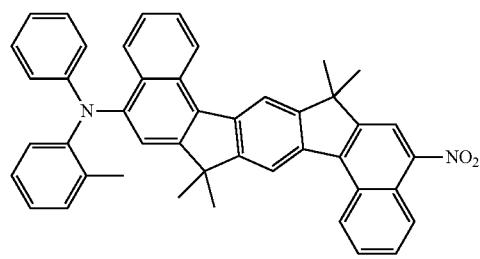
(92)
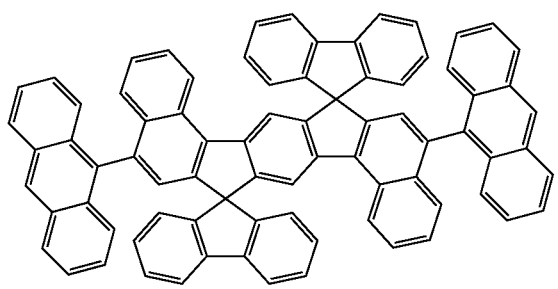
(93)
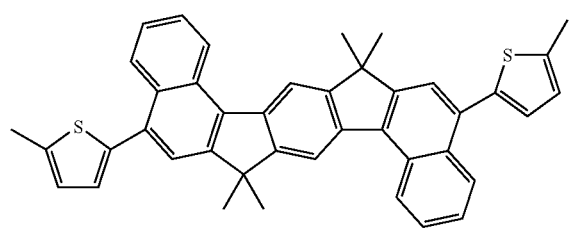
(94)
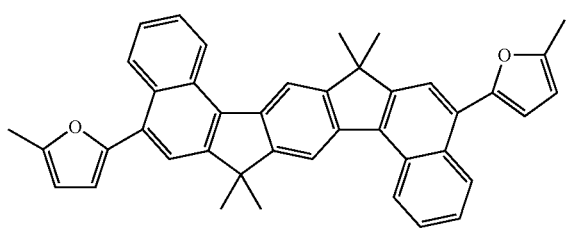
(95)
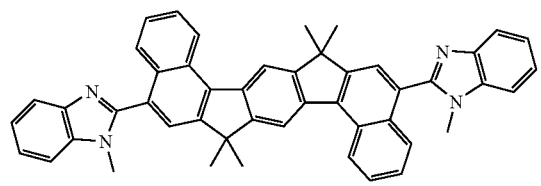
(96)
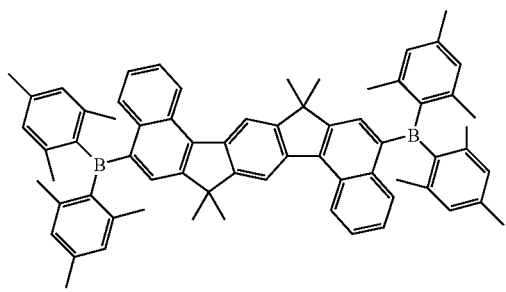
(97)
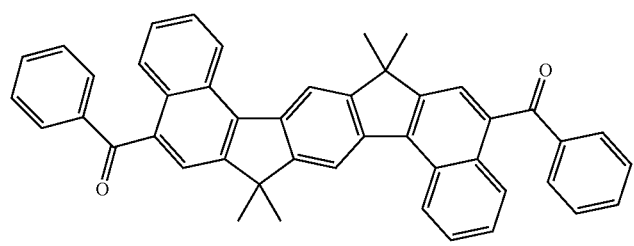

(98)
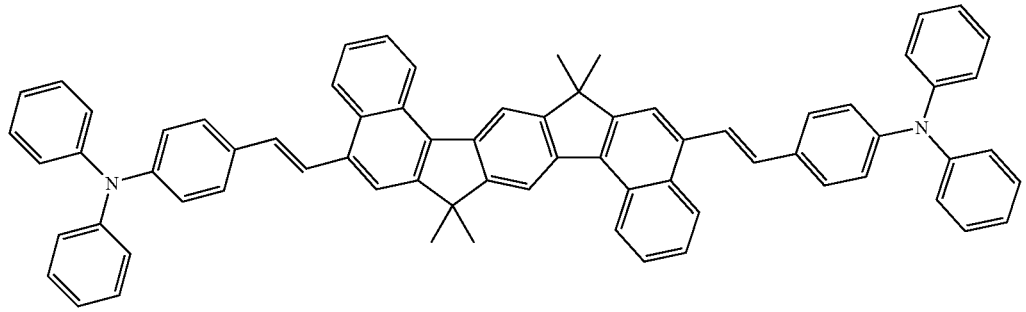
(99)
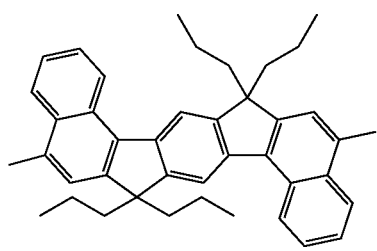
(100)
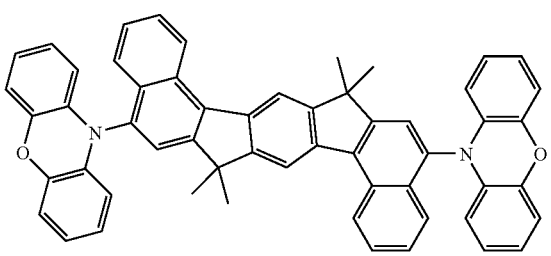
(101)
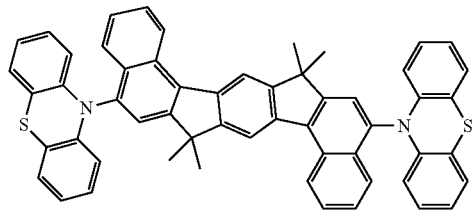
(102)
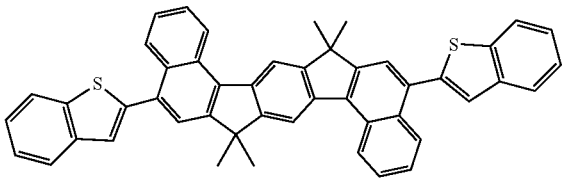
(103)
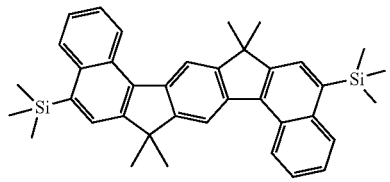
(104)
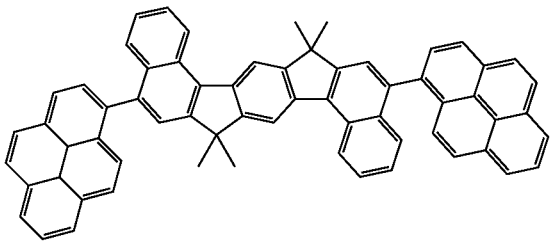
(105)
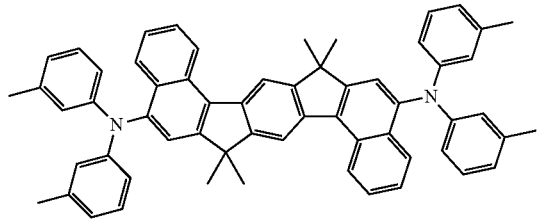
(106)
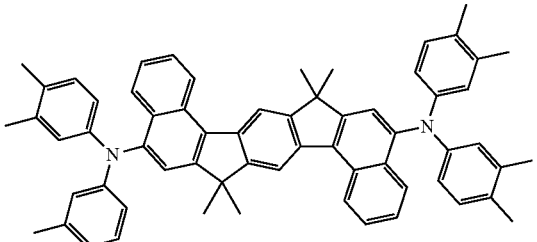
(107)
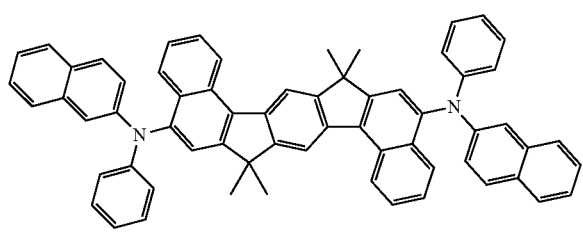
(108)
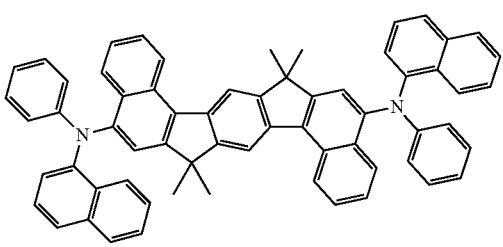

-continued
(109)
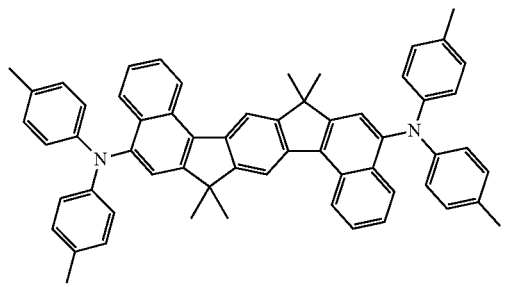
(110)
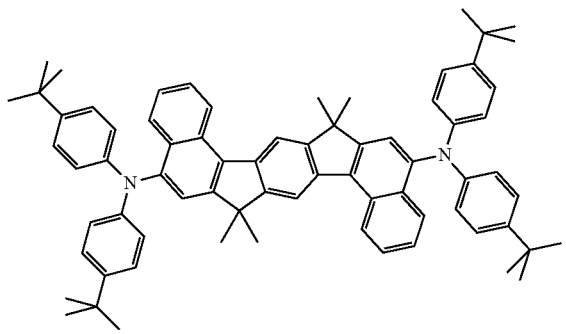
(111)
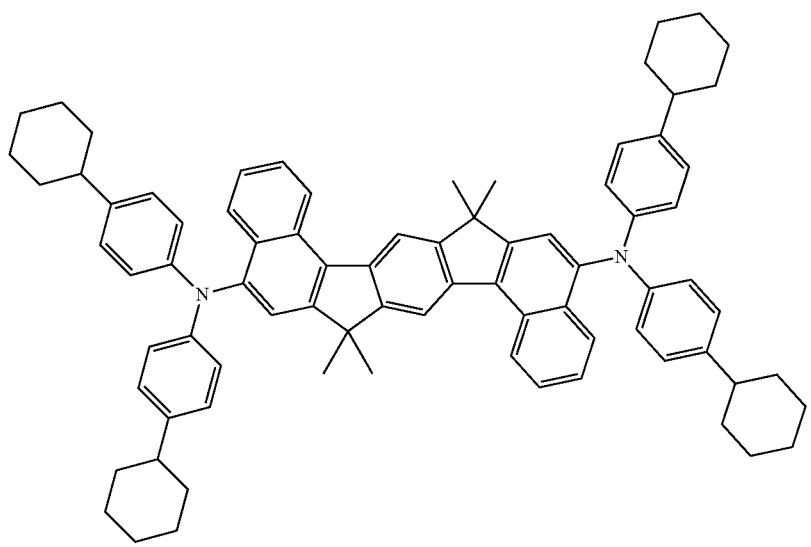
(112)
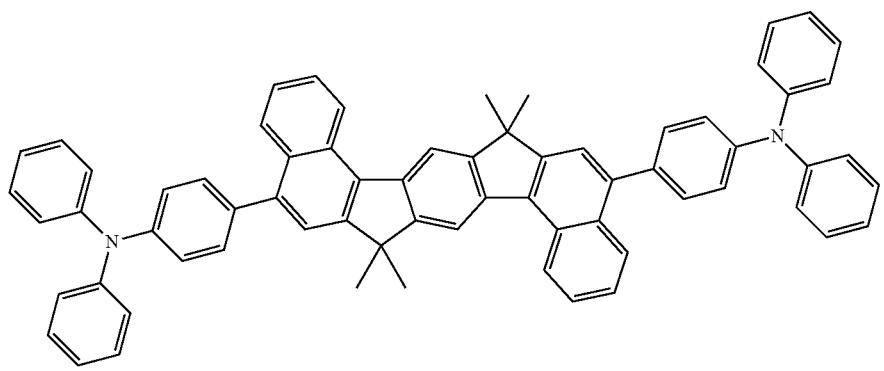
(113)
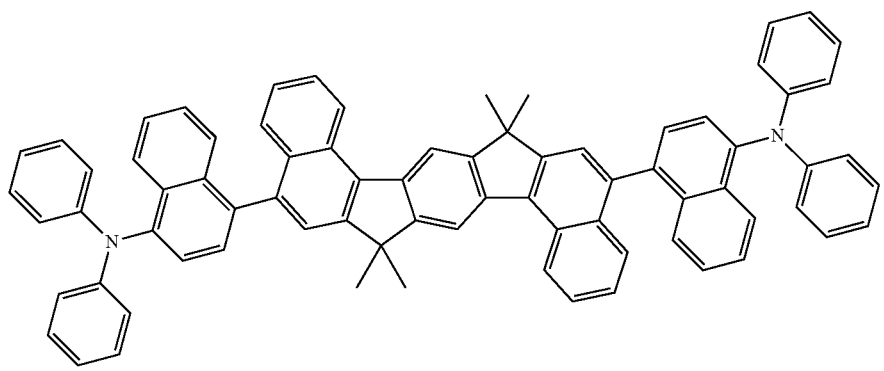

-continued
(114)
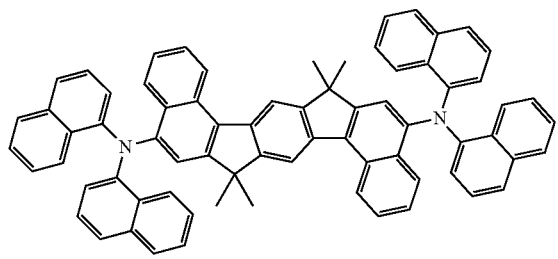
(115)
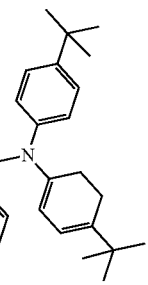
(116)
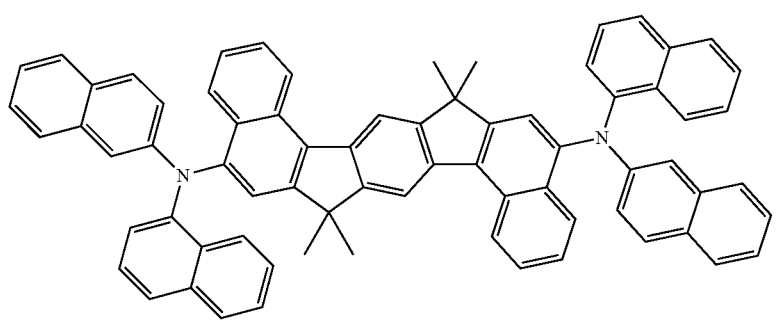
(117)
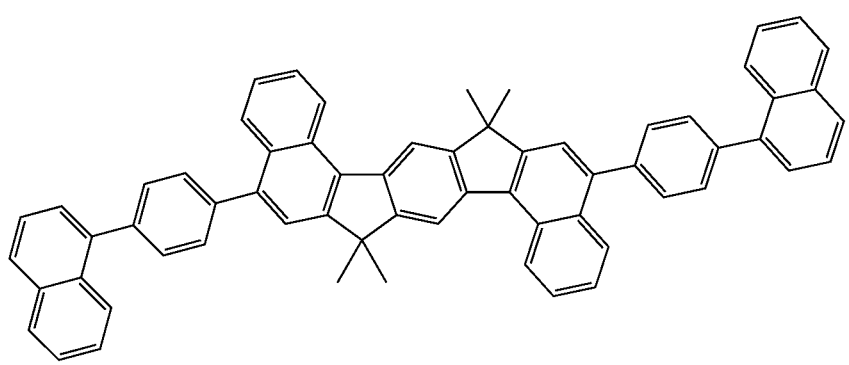
(118)
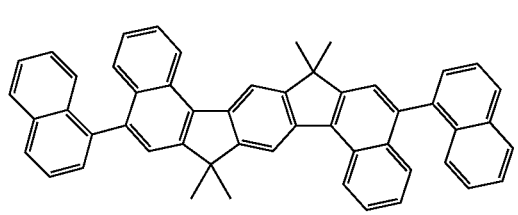
(119)
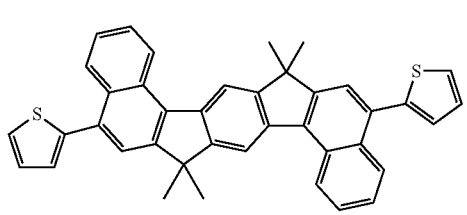
(120)
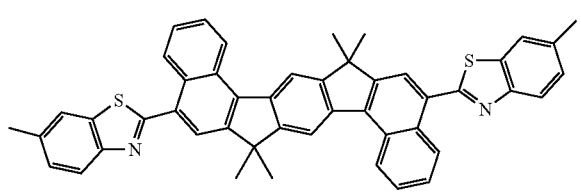
(121)
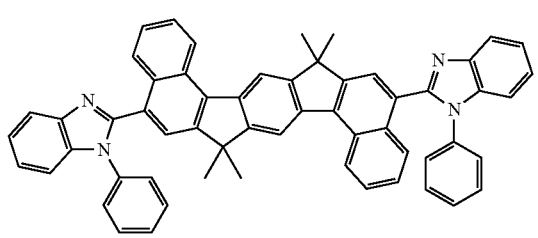

-continued
(122)
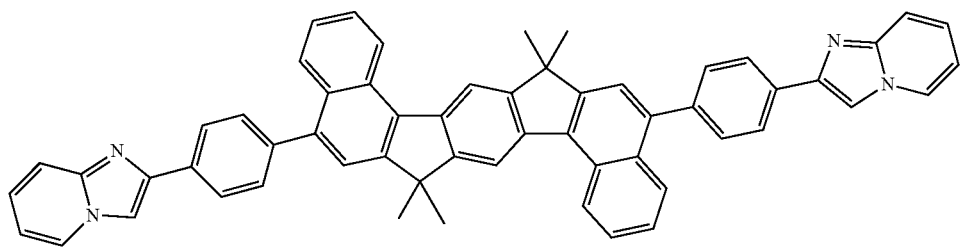
(123)
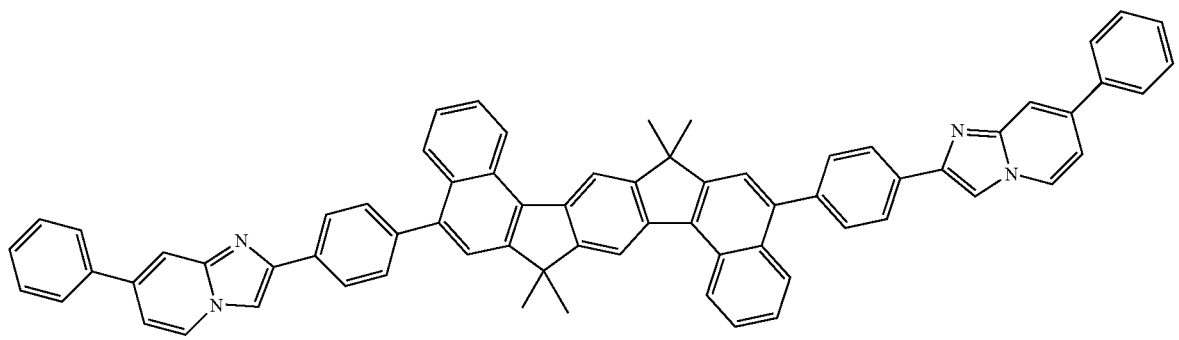
(124)
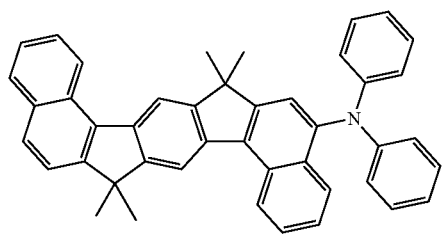
(125)
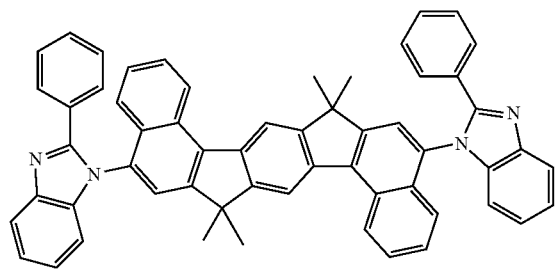
(126)
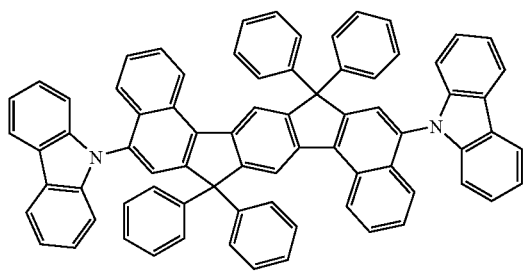
(127)
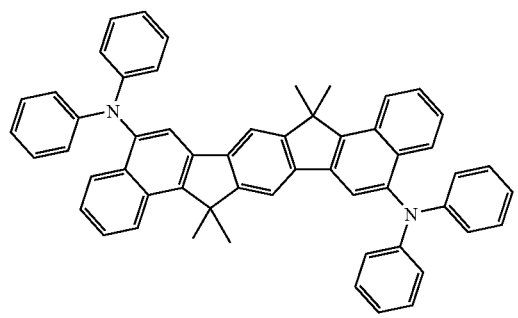
(128)
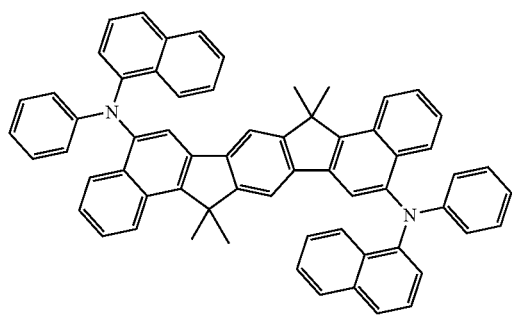
(129)
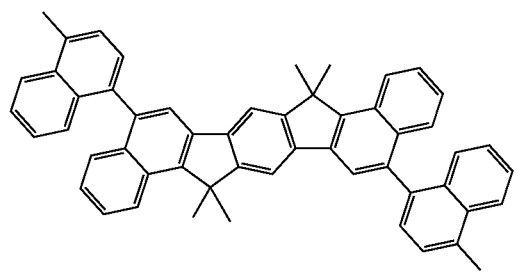

-continued

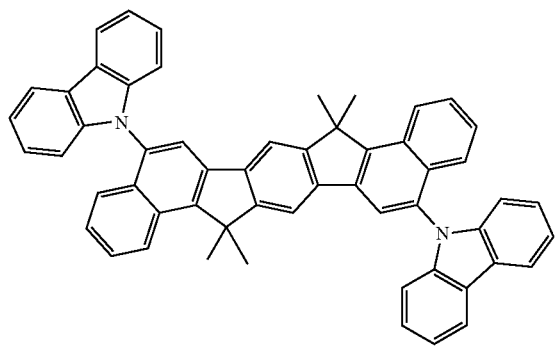
(130)

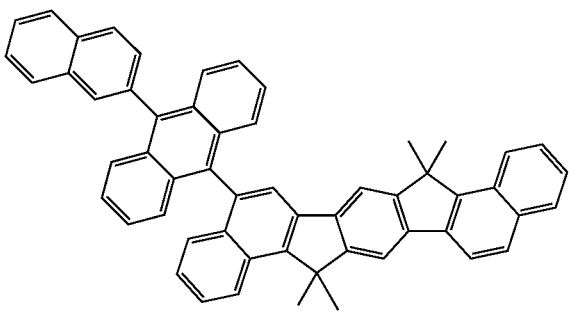
(131)

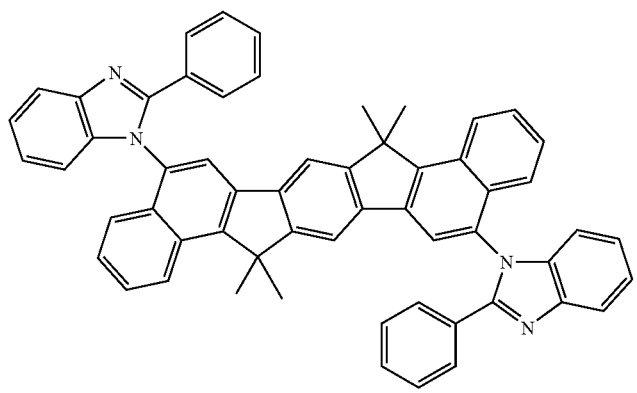
(132)

The compounds according to the invention described above, in particular compounds which are substituted by reactive leaving groups, such as bromine, iodine, boronic acid or boronic acid ester, can also be used as comonomers for the production of corresponding conjugated, partially conjugated or non-conjugated polymers, oligomers or also as the core of dendrimers. The polymerisation here is preferably carried out via the halogen functionality or the boronic acid functionality.

The invention thus furthermore relates to polymers, oligomers or dendrimers containing one or more compounds of the formulae (1) to (16) and (5a) to (11a) in which one or more radicals $R^1$ represent bonds from the compound of the formulae (1) to (16) and (5a) to (11a) to the polymer or dendrimer. These polymers, oligomers or dendrimers may be conjugated, partially conjugated or non-conjugated.

The same preferences as described above apply to the recurring units of the formulae (1) to (16) or (5a) to (11a).

These compounds are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or the unpublished application DE 102005037734.3) or also a plurality of these units. These polymers usually also contain further units, for example emitting (fluorescent or phosphorescent) units, such as, for example, vinyltriarylamines (for example in accordance with the unpublished application DE 102005060473.0) or phosphorescent metal complexes (for example in accordance with WO 06/003000), and/or charge-transport units, in particular those based on triarylamines.

The compounds of the formulae (1) to (16) and (5a) to (11a) according to the invention can be prepared by synthesis steps known to the person skilled in the art. Thus, the various skeletons can be prepared, for example, by acid-catalysed cyclisation of the corresponding tertiary alcohols, as shown in general terms in scheme 1 for the compounds of the formula (1). This skeleton can be functionalised by standard methods, for example by Friedel-Crafts alkylation or acylation. Furthermore, the skeleton can be brominated by standard methods of organic chemistry. The brominated compounds represent the basis for further functionalisations. Thus, they can be reacted with arylboronic acids or arylboronic acid derivatives by Suzuki coupling or with organotin compounds by the Stille method to give extended aromatic compounds. Coupling to aromatic or aliphatic amines by the Hartwig-Buchwald method gives the corresponding amines. Furthermore, the brominated derivatives can be converted into ketones by lithiation and reaction with electrophiles, such as benzonitrile, and subsequent acidic hydrolysis or into phosphine oxides by reaction with chlorodiphenylphosphines followed by oxidation.

Scheme 1

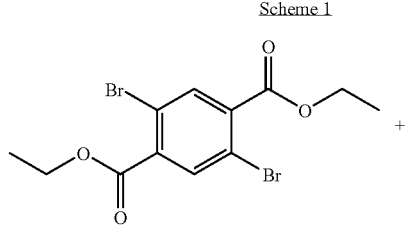

+

-continued

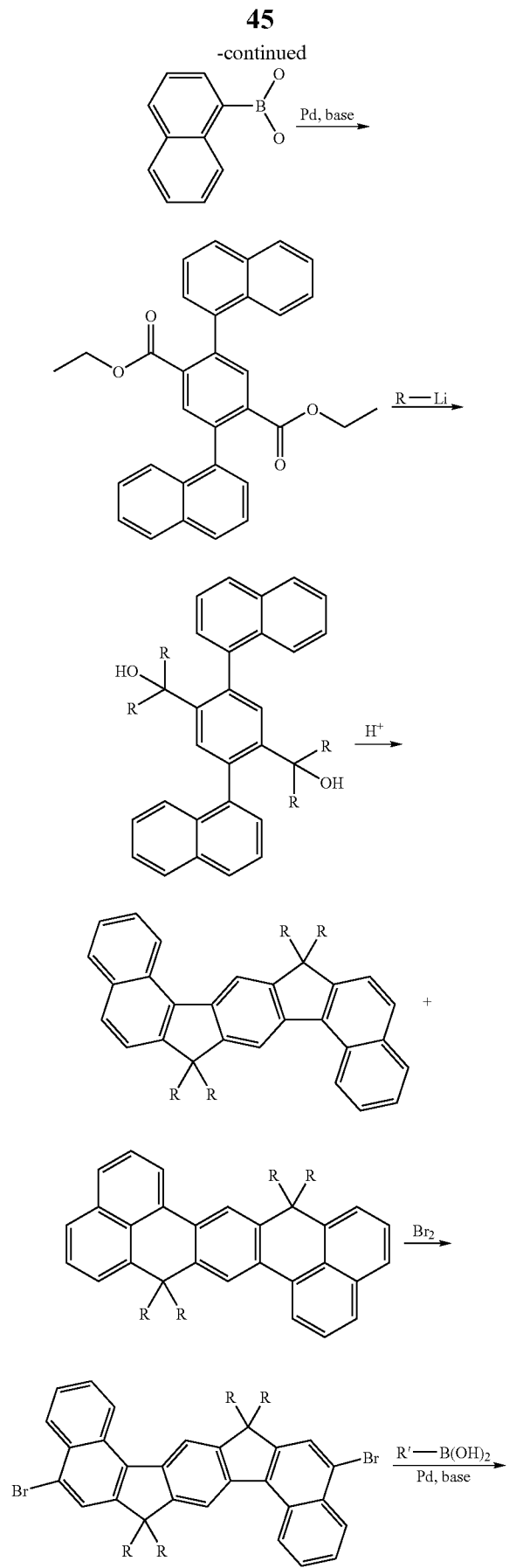

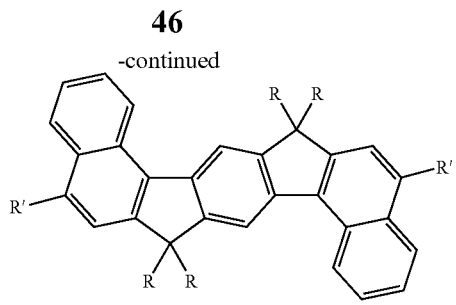

The process described above leads entirely analogously to compounds of the formula (3) or formula (4) if 2-naphthylboronic acid is employed instead of 1-naphthylboronic acid in the first coupling step.

Furthermore, the brominated compounds can be employed, either directly or after conversion into a boronic acid derivative, as monomers for polymers, oligomers or dendrimers.

In the synthesis, both the 5-membered ring/5-membered ring derivatives and also the 6-membered ring/6-membered ring derivatives, the 5-membered ring/6-membered ring derivatives or mixtures of these compounds are formed, depending on the synthetic conditions. These can either be separated and processed further as pure compounds or they can also be employed as a mixture.

The present invention furthermore relates to a process for the synthesis of compounds of the formulae (1) to (4), comprising the following steps:
a) coupling of a functionalised naphthalene to a tetra-functionalised benzene derivative;
b) optionally further functionalisation of the functional groups on the benzene derivative;
c) ring closure with acid catalysis; and
d) functionalisation of the parent structure obtained by steps a) to c) by bromination, followed by Hartwig-Buchwald coupling to an aromatic amine or Suzuki coupling to an arylboronic acid or an arylboronic acid derivative.

The functional group on the naphthalene here is preferably a boronic acid group or a boronic acid derivative. The two functional groups for the coupling on the benzene derivative are preferably chlorine, bromine or iodine, particularly preferably bromine. The further two functional groups on the benzene derivative are preferably two ester groups of the formula C(=O)—O—R, where R stands for an alkyl group having 1 to 20 C atoms. The further functionalisation in step b) can be carried out, for example, by addition of an organolithium compound, giving a tertiary alcohol.

The compounds of the formula (1) to formula (16) and (5a) to (11a) are suitable for use in organic electroluminescent devices (OLEDs, PLEDs). Depending on the substitution, the compounds are employed in different functions and layers in the OLED.

The invention therefore furthermore relates to the use of compounds of the formulae (1) to (16) and (5a) to (11a) and in particular the preferred embodiments mentioned above in organic electronic devices, in particular in organic electroluminescent devices.

The invention still further relates to organic electronic devices comprising at least one compound selected from compounds of the formulae (1) to (16) and (5a) to (11a), in particular organic electroluminescent devices comprising anode, cathode and at least one emitting layer, characterised in that at least one layer comprises at least one compound selected from compounds of the formulae (1) to (16) and (5a) to (11a), in particular the preferred embodiments mentioned above.

Apart from cathode, anode and emitting layer, the organic electroluminescent device may also comprise further layers. These can be selected, for example, from: hole-injection layer, hole-transport layer, electron-transport layer, electron-injection layer and/or charge-generation layer (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*). However, it should be pointed out that each of these layers does not necessarily have to be present.

In a further preferred embodiment of the invention, the organic electroluminescent device comprises a plurality of emitting layers, where at least one layer comprises at least one compound of the formulae (1) to (16) and (5a) to (11a). These emission layers particularly preferably have in total a plurality of emission maxima between 380 nm and 750 nm, resulting overall in white emission, i.e. various emitting compounds which are able to fluoresce or phosphoresce and emit yellow, orange or red light are used in the emitting layers. Particular preference is given to three-layer systems, in which at least one of these layers comprises at least one compound of the formulae (1) to (16) and (5a) to (11a) and in which the three layers exhibit blue, green and orange or red emission (for the basic structure see, for example, WO 05/011013). Emitters which have broad-band emission bands and thus exhibit white emission are likewise suitable for white emission.

In an embodiment of the invention, the compounds of the formulae (1) to (16) and (5a) to (11a) are employed as host for a fluorescent dopant. In this case, one or more substituents $R^1$ are preferably selected from simple or condensed aryl or heteroaryl groups, in particular phenyl, o-, m- or p-biphenyl, 1- or 2-naphthyl, anthryl, in particular phenylanthryl or 1- or 2-naphthylanthryl, 2-fluorenyl and 2-spirobifluorenyl, each of which may be substituted by one or more radicals $R^2$. This applies, in particular, to the radicals $R^1$ on the structures of the formulae (5a) to (11a).

A host material in a system comprising host and dopant is taken to mean the component which is present in the system in the higher proportion. In a system comprising a host and a plurality of dopants, the host is taken to mean the component whose proportion is the highest in the mixture.

The proportion of the host material according to the invention in the emitting layer is between 50.0 and 99.9% by weight, preferably between 80.0 and 99.5% by weight, particularly preferably between 90.0 and 99.0% by weight. Correspondingly, the proportion of the dopant is between 0.1 and 50.0% by weight, preferably between 0.5 and 20.0% by weight, particularly preferably between 1.0 and 10.0% by weight.

Preferred dopants in fluorescent devices are selected from the class of the monostyrylamines, the distyrylamines, the tristyrylamines, the tetrastyrylamines and the arylamines. A monostyrylamine is taken to mean a compound which contains one styryl group and at least one amine, which is preferably aromatic. A distyrylamine is taken to mean a compound which contains two styryl groups and at least one amine, which is preferably aromatic. A tristyrylamine is taken to mean a compound which contains three styryl groups and at least one amine, which is preferably aromatic. A tetrastyrylamine is taken to mean a compound which contains four styryl groups and at least one amine, which is preferably aromatic. For the purposes of this invention, an arylamine or an aromatic amine is taken to mean a compound which contains three aromatic or heteroaromatic ring systems bonded directly to the nitrogen, at least one of which is preferably a condensed ring system having at least 14 aromatic ring atoms if no styryl group is present in the system. The styryl groups are particularly preferably stilbenes, which may also be further substituted on the double bond or on the aromatic rings. Examples of dopants of this type are substituted or unsubstituted tristilbenamines or further dopants which are described, for example, in WO 06/000388, WO 06/058737, WO 06/000389 and the unpublished patent applications DE 102005058543.4 and DE 102006015183.6. In addition, preference is given to compounds as described in WO 06/122630, likewise the dopants of the formulae (1) to (16) and (5a) to (11a) according to the invention mentioned below.

In a further embodiment of the invention, the compounds of the formulae (1) to (16) and (5a) to (11a) are employed as matrix for phosphorescent dopants. In this case, one or more substituents $R^1$ and/or bridges X preferably contain at least one group $C=O$, $P(=O)$ and/or $SO_2$. These groups are particularly preferably bonded directly to the central unit according to the invention and furthermore particularly preferably also contain one or in the case of phosphine oxide two further aromatic substituents. This applies, in particular, to the radicals $R^1$ on the structures of the formulae (5a) to (11a).

In phosphorescent devices, the dopant is preferably selected from the class of the metal complexes containing at least one element having an atomic number of greater than 20, preferably greater than 38 and less than 84, particularly preferably greater than 56 and less than 80. Preference is given to the use of metal complexes which contain copper, molybdenum, tungsten, rhenium, ruthenium, osmium, rhodium, iridium, palladium, platinum, silver, gold or europium, in particular iridium or platinum. Phosphorescent materials as used in accordance with the prior art are generally suitable for this purpose.

In still a further embodiment of the invention, the compounds of the formulae (1) to (16) and (5a) to (11a) are employed as emitting materials. The compounds are suitable as emitting compounds in particular if at least one substituent $R^1$ contains at least one vinylaryl unit, at least one vinylarylamine unit and/or at least one diarylamino unit $N(Ar)_2$. This applies, in particular, to the radicals $R^1$ on the structures of the formulae (5a) to (11a). The two radicals $R^1$ on the structures of the formulae (5a) to (11a) are preferably selected identically.

The proportion of the emitting compound of the formulae (1) to (16) and (5a) to (11a) in the mixture of the emitting layer is between 0.1 and 50.0% by weight, preferably between 0.5 and 20.0% by weight, particularly preferably between 1.0 and 10.0% by weight. Correspondingly, the proportion of the host material is between 50.0 and 99.9% by weight, preferably between 80.0 and 99.5% by weight, particularly preferably between 90.0 and 99.0% by weight.

Suitable host materials for this purpose are various classes of substance. Preferred host materials are selected from the classes of the oligoarylenes (for example 2,2',7,7'-tetraphenylspirobifluorene as described in EP 676461 or dinaphthylanthracene), in particular the oligoarylenes containing condensed aromatic groups, the oligoarylenevinylenes (for example DPVBi or spiro-DPVBi as described in EP 676461), the polypodal metal complexes (for example as described in WO 04/081017), the hole-conducting compounds (for example as described in WO 04/058911), the electron-conducting compounds, in particular ketones, phosphine oxides, sulfoxides, etc. (for example as described in WO 05/084081 and WO 05/084082), the atropisomers (for example as described in WO 06/048268) or the boronic acid derivatives (for example as described in WO 06/117052). Suitable host materials are furthermore also the compounds of the formulae (1) to (16) and (5a) to (11a) according to the invention described above. Particularly preferred host materials, in addition to the compounds according to the invention, are selected from the classes of the oligoarylenes containing naphthalene, anthracene and/or pyrene or atropisomers of these compounds, the oligoarylenevinylenes, the ketones, the phosphine oxides and the sulfoxides. Very particularly preferred host materials, in addition to the compounds according to the invention, are selected from the classes of the oligoarylenes containing anthracene and/or pyrene or atropisomers of these compounds, the phosphine oxides and the sulfoxides, in particular anthracene derivatives which are substituted by two aromatic groups, which may be identical or different. For the purposes of this invention, an oligoarylene is intended to be taken to mean a compound in which at least three aryl or arylene groups are bonded to one another.

In still a further embodiment of the invention, the compounds of the formulae (1) to (16) and (5a) to (11a) are employed as hole-transport material or as hole-injection material. The compounds are then preferably substituted by at least one group $N(Ar)_2$, preferably by at least two groups $N(Ar)_2$, The groups $N(Ar)_2$ are preferably selected from the formulae (17) and (18) described above. This applies, in particular, to the radicals $R^1$ on the structures of the formulae (5a) to (11a). The compound is preferably employed in a hole-transport or hole-injection layer. For the purposes of this invention, a hole-injection layer is a layer which is directly adjacent to the anode. For the purposes of this invention, a hole-transport layer is a layer which lies between a hole-injection layer and an emission layer. If compounds according to the invention are used as hole-transport or hole-injection material, it may be preferred for them to be doped with electron-acceptor compounds, for example with $F_4$-TCNQ or with compounds as described in EP 1476881 or EP 1596445.

In still a further embodiment of the invention, the compounds of the formulae (1) to (16) and (5a) to (11a) are employed as electron-transport material. It is preferred here for one or more substituents $R^1$ to contain at least one unit C=O, P(=O) and/or $SO_2$. These groups are particularly preferably bonded directly to the central unit according to the invention and furthermore particularly preferably also contain one or in the case of phosphine oxide two further aromatic substituents. This applies, in particular, to the radicals $R^1$ on the structures of the formulae (5a) to (11a). It may furthermore be preferred for the compound to be doped with electron-donor compounds.

In polymers too, recurring units of the formulae (1) to (16) and (5a) to (11a) can be employed either as polymer backbone, as emitting unit, as hole-transporting unit and/or as electron-transporting unit. The preferred substitution patterns here correspond to those described above.

Preference is furthermore given to an organic electroluminescent device, characterised in that one or more layers are coated by a sublimation process, in which the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electroluminescent device, characterised in that one or more layers are coated by the OVPD (organic vapour phase deposition) process or with the aid of carrier-gas sublimation, in which the materials are applied at a pressure between $10^{-5}$ mbar and 1 bar.

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose. High solubility can be achieved through suitable substitution of the compounds.

The compounds according to the invention have the following surprising advantages over the prior art on use in organic electroluminescent devices:

1. The compounds according to the invention have a lower LUMO (lowest unoccupied molecular orbital) than compounds which are usually used in accordance with the prior art, and are consequently easier to reduce. This results in improved electron injection and thus a reduction in the operating voltage.
2. The compounds according to the invention have a small band separation and can thus be regarded as bipolar structures which can be both reduced well and also oxidised well. They are thus equally suitable for hole injection and electron injection. These compounds are thus a step in the direction of emitting layers which comprise only one pure substance. This represents a technical simplification in device production.
3. On use in organic electroluminescent devices, the compounds according to the invention result in significantly improved lifetimes compared with the prior art.
4. The compounds according to the invention have very high thermal stability, which facilitates both straightforward bulk sublimation for purification of the compounds and also decomposition-free thermal vapour deposition of the compounds during production of the organic electroluminescent devices.

The present application text is directed to the use of the compounds according to the invention in relation to OLEDs and PLEDs and the corresponding displays. In spite of this restriction of the description, it is possible for the person skilled in the art, without further inventive step, also to employ the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photoreceptors.

The present invention likewise relates to the use of the compounds according to the invention in the corresponding devices and to these devices themselves.

The invention is explained in greater detail by the following examples without wishing thereby to restrict it.

EXAMPLES

The following syntheses were carried out under a protective-gas atmosphere, unless indicated otherwise. The starting materials were purchased from ALDRICH or ABCR.

Example 1

Synthesis of 3,8-bis(N,N-diphenylamino)-1,2,6,7-dibenzo-6,6,12,12-tetramethyl-6,12-dihydroindeno[1,2-b]fluorene a) Diethyl 2,5-dinaphth-1-ylterephthalate

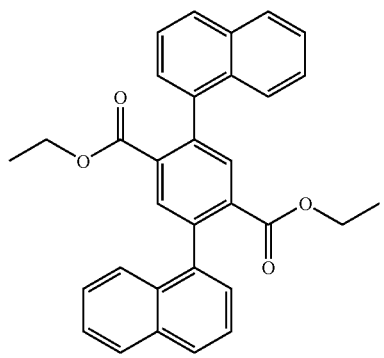 [SMILES: CCOC(=O)c1cc(-c2cccc3ccccc23)c(C(=O)OCC)cc1-c1cccc2ccccc12]

193.3 g (0.82 mol) of naphthylboronic acid, 180.4 g (474 mmol) of diethyl dibromoterephthalate and 315.9 g (2-29 mol) of potassium carbonate are initially introduced in a mixture of 850 ml of toluene and 850 ml of water and saturated with $N_2$ for 30 min. After addition of 1.36 g (1.18 mmol) of $Pd(PPh_3)_4$, the mixture is heated at the boil for 4 h. After cooling to RT and addition of 400 ml of EtOH, the mixture is cooled to room temperature and stirred for 1 h, and the precipitate is filtered off with suction, washed with water, EtOH and heptane and dried at 80° C. in vacuo. The yield of colourless solid is 160.7 g (71%).

b) 2-[4-(1-Hydroxy-1-methylethyl)-2,5-dinaphth-1-ylphenyl]propan-2-ol

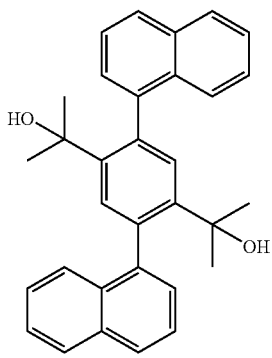 [SMILES: CC(C)(O)c1cc(-c2cccc3ccccc23)c(C(C)(C)O)cc1-c1cccc2ccccc12]

64.6 g (136.4 mmol) of diethyl 2,5-dinaphth-1-ylterephthalate are initially introduced in 600 ml of THF, the mixture is cooled to −70° C., and 400 ml (600 mmol) of 1.6 M methyllithium solution are added dropwise over the course of 60 min at −70° C. After 2 h at −70° C., firstly 30 ml of ice-water, then 60 ml of 50% acetic acid are added dropwise, the reaction mixture is worked up by extraction with ethyl acetate/water, and the organic phase is dried over $Na_2SO_4$ and freed from solvent in vacuo, giving 60.3 g (99%) of a colourless solid.

c) 1,2,6,7-Dibenzo-6,6,12,12-tetramethyl-6,12-dihydroindeno[1,2-b]-fluorene

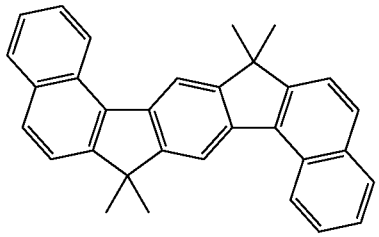 [SMILES: CC1(C)c2cc3c(cc2-c2c1ccc1ccccc21)C(C)(C)c1ccc2ccccc2c1-3]

34.12 g (76 mmol) of 2-[4-(1-hydroxy-1-methylethyl)-2,5-dinaphth-1-yl-phenyl]propan-2-ol are initially introduced in 600 ml of toluene, 1 ml of conc. $H_2SO_4$ is added, and the mixture is heated at the boil on a water separator until the discharge of water is complete. After cooling to RT, the precipitated reaction product (exclusively with two 5-membered rings according to $^1$H-NMR) is filtered off with suction and recrystallised from NMP, giving a yellowish powder having a purity >99.5% in a yield of 32 g (78%).

d) 3,8-Dibromo-1,2,6,7-dibenzo-6,6,12,12-tetramethyl-6,12-dihydroindeno[1,2-b]fluorene

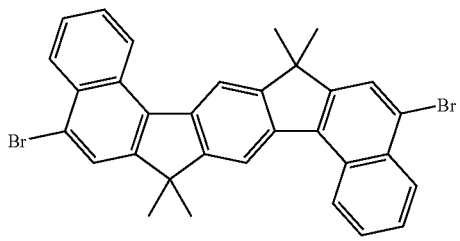 [SMILES: CC1(C)c2cc3c(cc2-c2c1cc(Br)c1ccccc21)C(C)(C)c1cc(Br)c2ccccc2c1-3]

17.5 g (43 mmol) of 1,2,6,7-dibenzo-6,6,12,12-tetramethyl-6,12-dihydroindeno[1,2-b]fluorene are initially introduced in 500 ml of dichloromethane with exclusion of light, and cooled to 5° C., 4.7 ml (86 mmol) of bromine in 40 ml of dichloromethane are added dropwise over the course of 15 min, and the mixture is stirred at 5° C. for 6 h. The reaction is monitored by HPLC analysis of reaction aliquots. When the conversion is complete, the reaction is terminated by addition of 20 ml of EtOH, and the product is filtered off with suction, washed a number of times with EtOH and subsequently recrystallised twice from NMP, giving 21.3 g (88%) of a pale-yellow solid, which, according to HPLC analysis, has a content of >99.8%.

e) 3,8-Bis(N,N-diphenylamino)-1,2,6,7-dibenzo-6,6,2,12-tetramethyl-6,12-dihydroindeno[1,2-b]fluorene

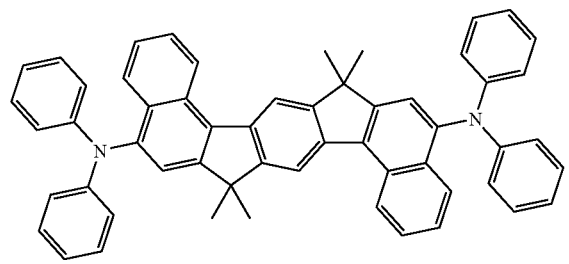 [SMILES: CC1(C)c2cc3c(cc2-c2c1cc(N(c1ccccc1)c1ccccc1)c1ccccc21)C(C)(C)c1cc(N(c2ccccc2)c2ccccc2)c2ccccc2c1-3]

40 g (70 mmol) of 3,8-dibromo-1,2,6,7-dibenzo-6,6,12,12-tetramethyl-6,12-dihydroindeno[1,2-b]fluorene and 31 g (184 mmol) of diphenylamine are suspended in 750 ml of anhydrous toluene, 600 mg (3 mmol) of tri-tert-butylphosphine and 340 mg (1.5 mmol) of Pd(OAc)$_2$ and 20 g (211 mmol) of NaO$^t$Bu are subsequently added, and the reaction mixture is heated at the boil for 4 h. When the reaction is complete, 400 ml of water are added, and the solid is filtered off with suction, washed with EtOH and dried. Re-crystallisation four times from NMP, washing once with boiling ethanol and subsequent double sublimation (340° C., 2×10$^{-5}$ mbar) gives 41.7 g (80%) of a pale-yellow solid having a purity, determined by HPLC, of >99.9%.

The following compounds are prepared analogously to the process described above (yields after sublimation with a purity of >99.9%) (Examples 2 to 9).

| Ex. | Structure | Yield (%) |
|---|---|---|
| 2 | 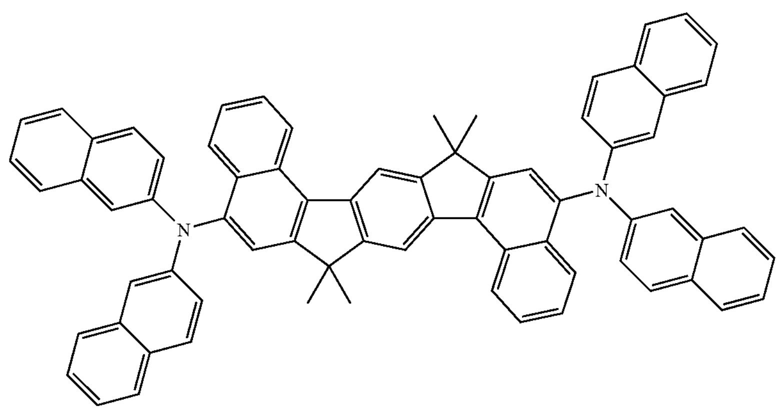 [SMILES: CC1(C)c2cc3c(cc2-c2c1cc(N(c1ccc4ccccc4c1)c1ccc4ccccc4c1)c1ccccc21)C(C)(C)c1cc(N(c2ccc4ccccc4c2)c2ccc4ccccc4c2)c2ccccc2c1-3] | 67 |
| 3 | 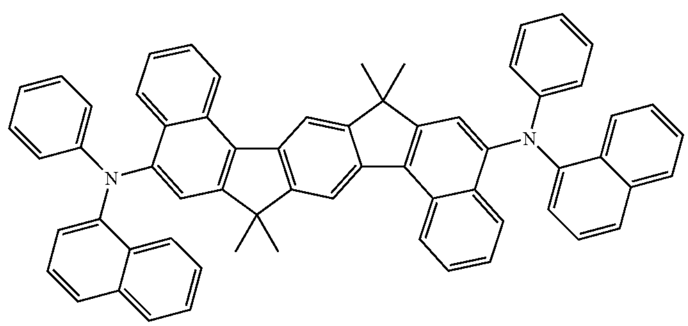 [SMILES: CC1(C)c2cc3c(cc2-c2c1cc(N(c1ccccc1)c1cccc4ccccc14)c1ccccc21)C(C)(C)c1cc(N(c2ccccc2)c2cccc4ccccc24)c2ccccc2c1-3] | 73 |
| 4 | 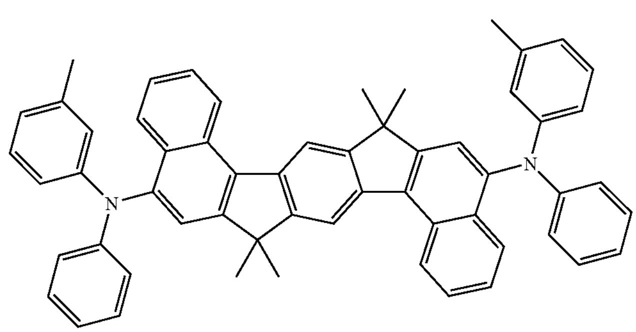 [SMILES: Cc1cccc(N(c2ccccc2)c2cc3c(c4ccccc24)-c2cc4c(cc2C3(C)C)-c2c(cc(N(c3ccccc3)c3cccc(C)c3)c3ccccc23)C4(C)C)c1] | 84 |

-continued
| Ex. | Structure | Yield (%) |
|---|---|---|
| 5 | 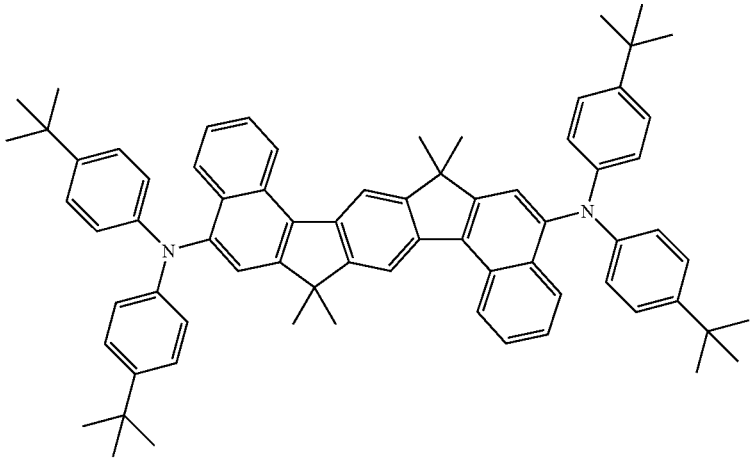 [SMILES: CC(C)(C)c1ccc(N(c2ccc(C(C)(C)C)cc2)c2cc3c(c4ccccc24)-c2cc4c(cc2C3(C)C)-c2c(cc(N(c3ccc(C(C)(C)C)cc3)c3ccc(C(C)(C)C)cc3)c3ccccc23)C4(C)C)cc1] | 64 |
| 6 | 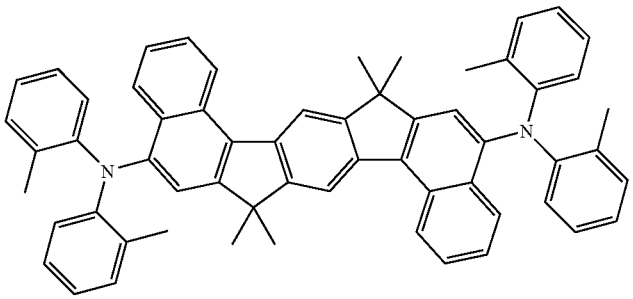 [SMILES: Cc1ccccc1N(c1ccccc1C)c1cc2c(c3ccccc13)-c1cc3c(cc1C2(C)C)-c1c(cc(N(c2ccccc2C)c2ccccc2C)c2ccccc12)C3(C)C] | 55 |
| 7 | 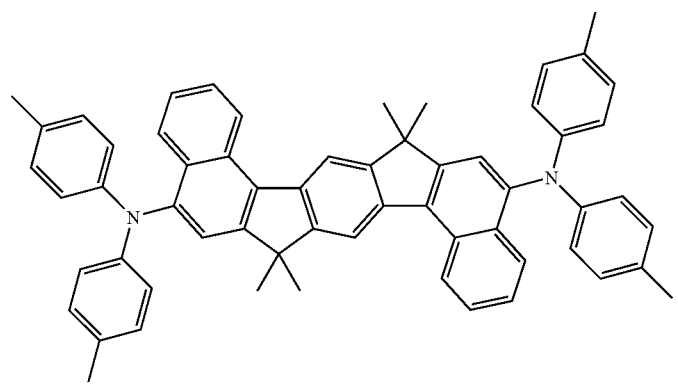 | 88 |
| 8 | 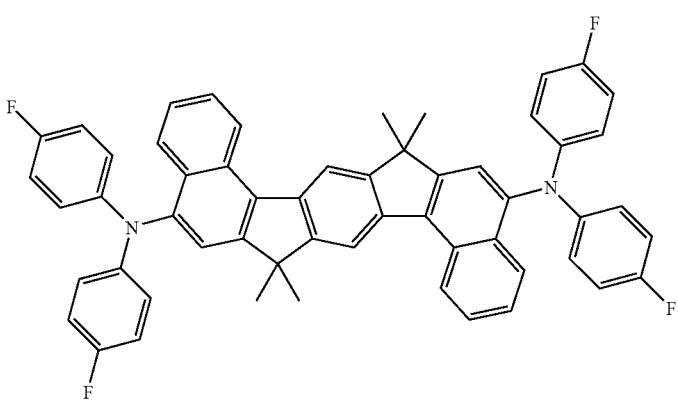 [SMILES: CC1(C)c2cc3c(cc2-c2c1cc(N(c1ccc(F)cc1)c1ccc(F)cc1)c1ccccc21)C(C)(C)c1cc(N(c2ccc(F)cc2)c2ccc(F)cc2)c2ccccc2c1-3] | 77 |

| Ex. | Structure | Yield (%) |
|---|---|---|
| 9 | 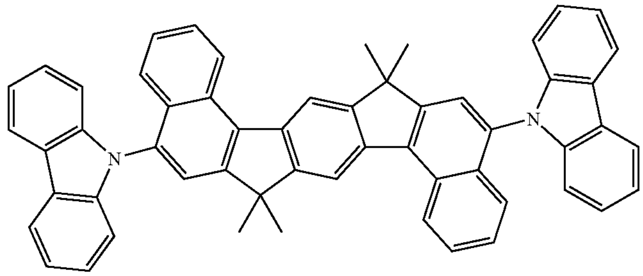 [SMILES: CC1(C)c2cc3c(cc2-c2c1cc(-n1c4ccccc4c4ccccc41)c1ccccc21)C(C)(C)c1cc(-n2c4ccccc4c4ccccc42)c2ccccc2c1-3] | 54 |

Example 10

Synthesis of 3,8-bis(4-triphenylamino)-1,2,6,7-dibenzo-6,6,12,12-tetramethyl-6,12-dihydroindeno[1,2-b]fluorene

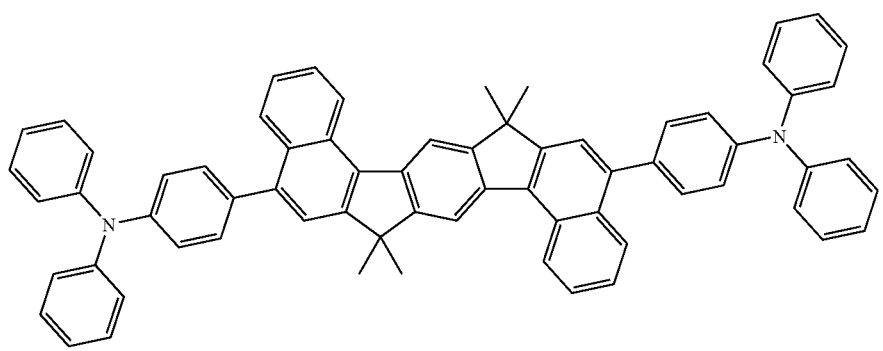 [SMILES: CC1(C)c2cc3c(cc2-c2c1cc(-c1ccc(N(c4ccccc4)c4ccccc4)cc1)c1ccccc21)C(C)(C)c1cc(-c2ccc(N(c4ccccc4)c4ccccc4)cc2)c2ccccc2c1-3]

69 g (122 mmol) of 3,8-dibromo-1,2,6,7-dibenzo-6,6,12,12-tetramethyl-6,12-dihydroindeno[1,2-b]fluorene (from Example 1d), 115 g (365 mmol) of triphenylamine-4-boronic acid ethylene glycol ester and 109 g (512 mmol) of tripotassium phosphate are suspended in a mixture of 450 ml of toluene, 150 ml of dioxane and 600 ml of water, the mixture is saturated with nitrogen, 4.4 g (14.6 mmol) of tris-o-tolylphosphine, followed by 0.5 g (2.4 mmol) of palladium acetate are added, and the mixture is heated at the boil for 12 h. After addition of 500 ml of EtOH, the precipitate is filtered off with suction, dried and recrystallised five times from NMP. Washing with boiling EtOH and double sublimation (370° C., 2×10$^{-5}$ mbar) gives 70 g (78 mmol) of the diamine having a purity >99.9% (HPLC).

The following compounds are prepared analogously to the process described above (yields after sublimation with a purity >99.9%) (Examples 11 to 13).

| Ex. | Structure | Yield (%) |
|---|---|---|
| 11 | 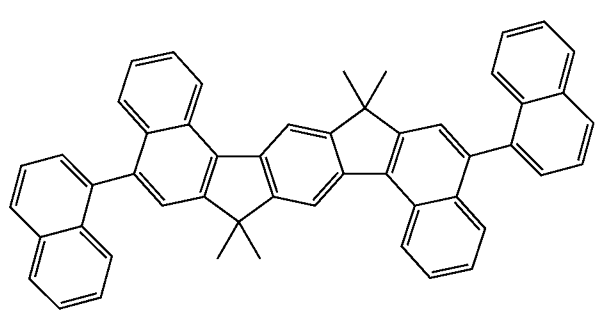 [SMILES: CC1(C)c2cc3c(cc2-c2c1cc(-c1cccc4ccccc14)c1ccccc21)C(C)(C)c1cc(-c2cccc4ccccc24)c2ccccc2c1-3] | 54 |

-continued

| Ex. | Structure | Yield (%) |
|---|---|---|
| 12 | 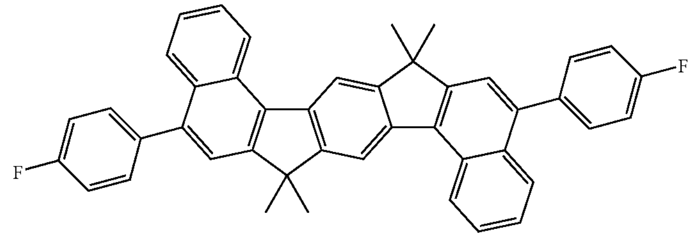 [SMILES: CC1(C)c2cc3c(cc2-c2c1cc(-c1ccc(F)cc1)c1ccccc21)C(C)(C)c1cc(-c2ccc(F)cc2)c2ccccc2c1-3] | 77 |
| 13 | 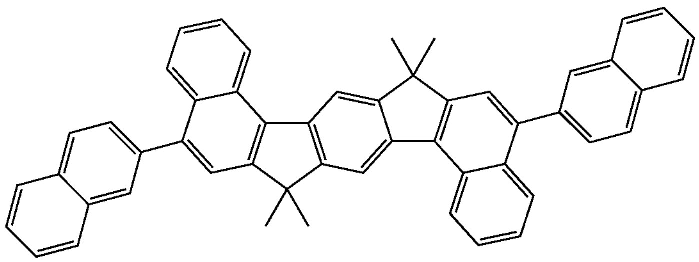 [SMILES: CC1(C)c2cc3c(cc2-c2c1cc(-c1ccc4ccccc4c1)c1ccccc21)C(C)(C)c1cc(-c2ccc4ccccc4c2)c2ccccc2c1-3] | 65 |

Example 14

Synthesis of 1,2,6,7-dibenzo-6,6,12,12-tetra(4-tert-butyl-phenyl)-6,12-dihydroindeno[1,2-b]fluorene a) {4-[Bis(4-tert-butylphenyl)hydroxymethyl]-2,5-dinaphth-1yl-phenyl}bis(4-tert-butylphenyl)methanol

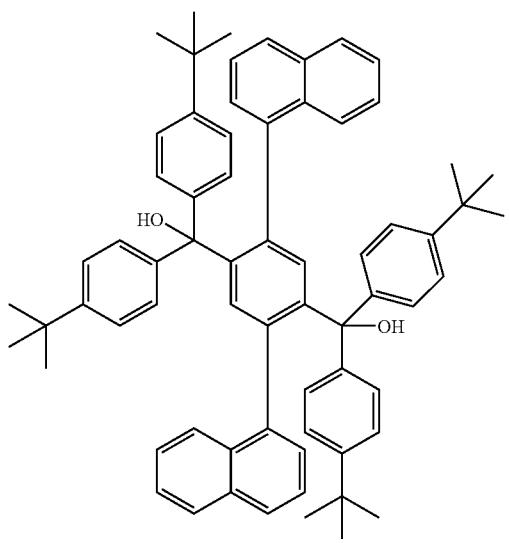 [SMILES: CC(C)(C)c1ccc(C(O)(c2ccc(C(C)(C)C)cc2)c2cc(-c3cccc4ccccc34)c(C(O)(c3ccc(C(C)(C)C)cc3)c3ccc(C(C)(C)C)cc3)cc2-c2cccc3ccccc23)cc1]

42.5 g (200 mmol) of t-butylbromobenzene are initially introduced in 200 ml of dried THF the mixture is cooled to −75° C. 100 ml (200 mmol) of n-BuLi (2 M in cyclohexane) are added dropwise over the course of 30 min, and the mixture is stirred at −75° C. for a further 2 h. 21.3 g (45 mmol) of diethyl 2,5-dinaphth-1-ylterephthalate (prepared as described in Example 1a) are dissolved in 160 ml of dry THF, the solution is added dropwise over the course of 30 min at −75° C. the mixture is stirred at −75° C. for 1 h, and, after warming to RT, 20 ml of 50% acetic acid are added dropwise. The reaction mixture is worked up by extraction with ethyl acetate and water, the organic phase is dried over $Na_2SO_4$, and the solvent is removed in vacuo, giving the diol as a colourless solid having a purity of >99%, determined by $^1$H-NMR spectroscopy (40.5 g, 98%).

b) 1,2,6,7-Dibenzo-6,6,12,12-tetra-(4-tert-butylphenyl)-6,12-dihydroindeno[1,2-b]fluorene

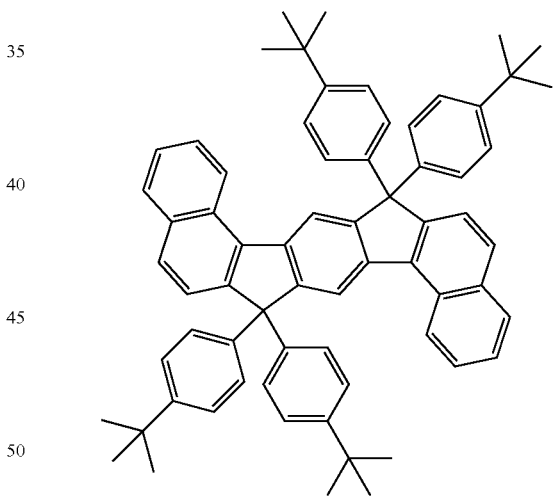

41.4 g (45 mmol) of {4-[bis(4-tert-butylphenyl)hydroxymethyl]-2,5-dinaphth-1-ylphenyl}bis(4-tert-butylphenyl) methanol are suspended in 500 ml of conc. acetic acid, 2 ml of conc. HCl are added, and the mixture is heated at the boil for 4 h. The crude product is filtered off and, according to $^1$H-NMR analysis, consists of a mixture of the product linked to give two 5-membered rings and the product linked to give two 6-membered rings (about 3:1). The separation and purification are carried out by recrystallisation seven times from dichlorobenzene. Double addition and removal of toluene by distillation, washing with boiling n-heptane and final double sublimation (400° C., 2×10$^{-5}$ mbar) gives the product in the form of a colourless solid (16.7 g, 42%).

The compound according to Example 14 can be functionalised further analogously to Examples 1 and 10.

Example 15

Synthesis of 2,7-bis(N,N-diphenylamino)-3,4,8,9-dibenzo-6,6,12,12-tetramethyl-6,12-dihydroindeno[1,2-b]fluorene a) 2,7-Bis(N,N-diphenylamino)-3,4,8,9-dibenzo-6,6,12,12-tetramethyl-6,12-dihydroindeno[1,2-b]fluorene

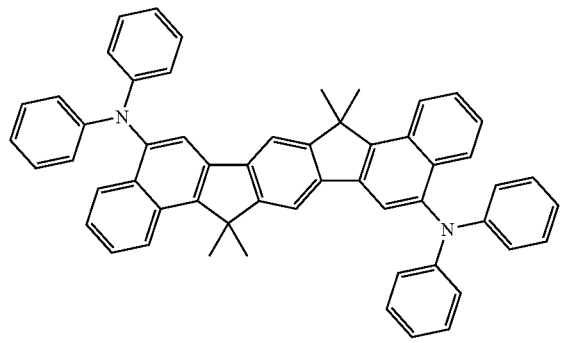 [SMILES: CC1(C)c2cc3c(cc2-c2cc(N(c4ccccc4)c4ccccc4)c4ccccc4c21)C(C)(C)c1c-3cc(N(c2ccccc2)c2ccccc2)c2ccccc12]

The compound is prepared analogously to Example 1 starting from 2-naphthaleneboronic acid instead of 1-naphthaleneboronic acid and is purified by recrystallisation four times from chlorobenzene and final sublimation (350° C., 2×10$^{-5}$ mbar). The yield for the amination is 66% with a purity of >99.9% (HPLC).

The following compounds are prepared analogously to the process described above (yields after sublimation with a purity of >99.9%) (Examples 16 to 23).

| Ex. | Structure | Yield (%) |
|---|---|---|
| 16 | 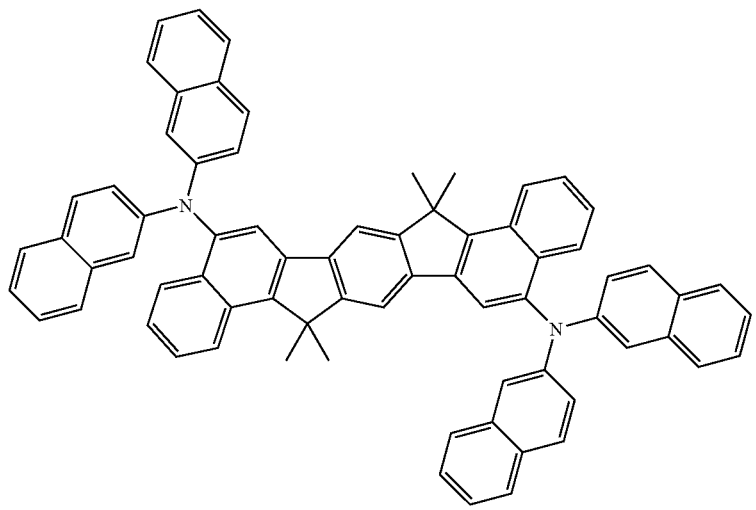 [SMILES: CC1(C)c2cc3c(cc2-c2cc(N(c4ccc5ccccc5c4)c4ccc5ccccc5c4)c4ccccc4c21)C(C)(C)c1c-3cc(N(c2ccc3ccccc3c2)c2ccc3ccccc3c2)c2ccccc12] | 88 |
| 17 | 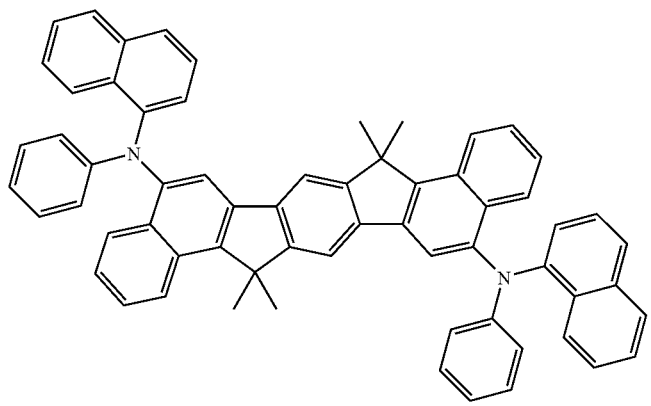 [SMILES: CC1(C)c2cc3c(cc2-c2cc(N(c4ccccc4)c4cccc5ccccc45)c4ccccc4c21)C(C)(C)c1c-3cc(N(c2ccccc2)c2cccc3ccccc23)c2ccccc12] | 71 |

| Ex. | Structure | Yield (%) |
|---|---|---|
| 18 | 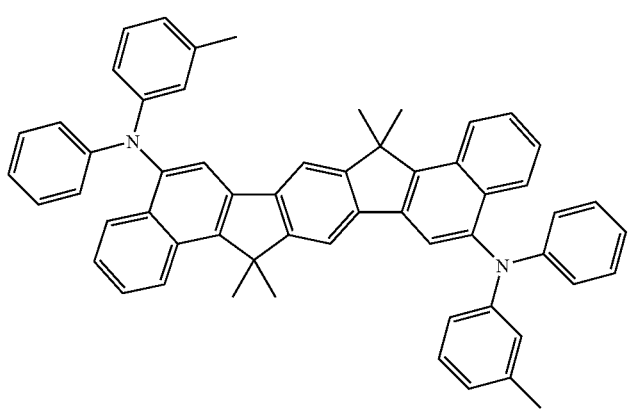 [SMILES: Cc1cccc(N(c2ccccc2)c2cc3c(c4ccccc24)C(C)(C)c2cc4c(cc2-3)C(C)(C)c2c-4cc(N(c3ccccc3)c3cccc(C)c3)c3ccccc23)c1] | 82 |
| 19 | 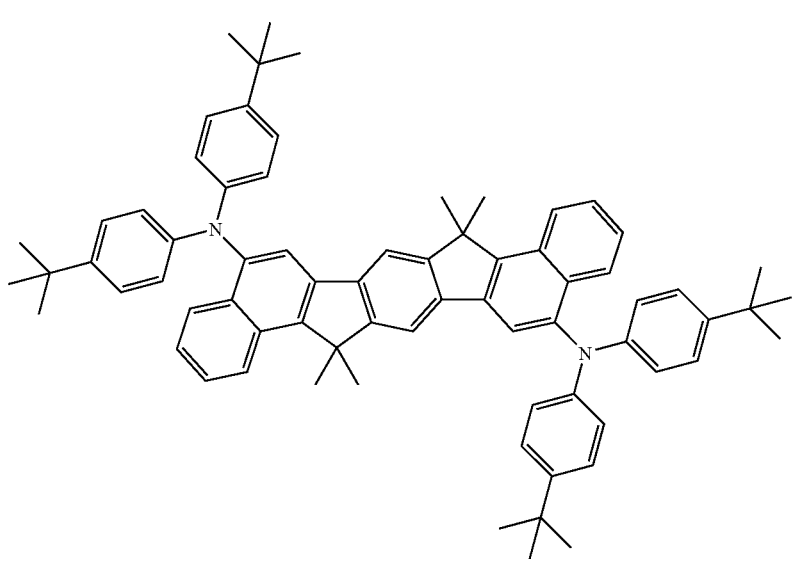 [SMILES: CC(C)(C)c1ccc(N(c2ccc(C(C)(C)C)cc2)c2cc3c(c4ccccc24)C(C)(C)c2cc4c(cc2-3)C(C)(C)c2c-4cc(N(c3ccc(C(C)(C)C)cc3)c3ccc(C(C)(C)C)cc3)c3ccccc23)cc1] | 66 |
| 20 | 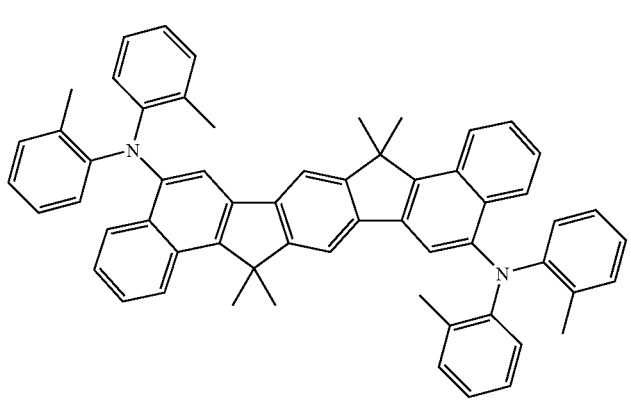 [SMILES: Cc1ccccc1N(c1ccccc1C)c1cc2c(c3ccccc13)C(C)(C)c1cc3c(cc1-2)C(C)(C)c1c-3cc(N(c2ccccc2C)c2ccccc2C)c2ccccc12] | 49 |

-continued

| Ex. | Structure | Yield (%) |
| --- | --- | --- |
| 21 | 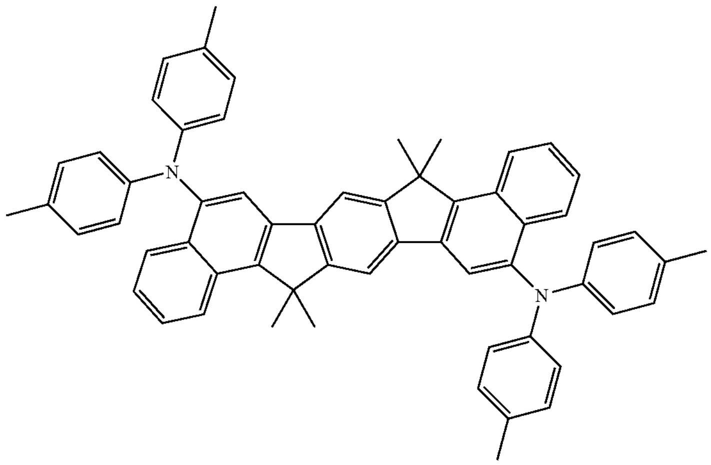 | 86 |
| 22 | 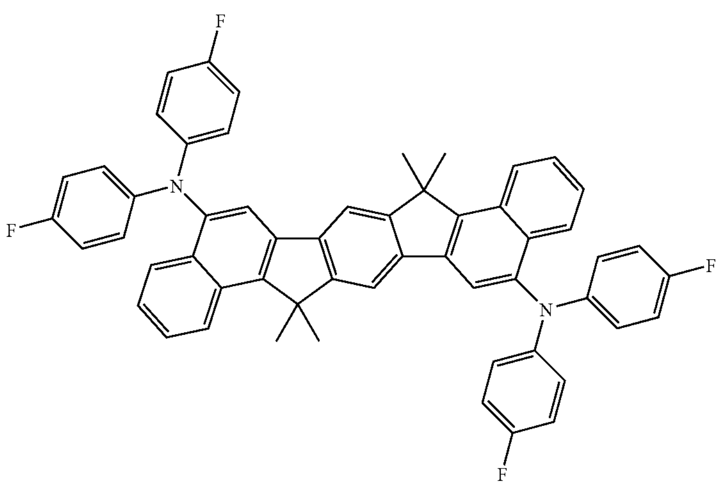 [SMILES: CC1(C)c2cc3c(cc2-c2cc(N(c4ccc(F)cc4)c4ccc(F)cc4)c4ccccc4c21)C(C)(C)c1c-3cc(N(c2ccc(F)cc2)c2ccc(F)cc2)c2ccccc12] | 75 |
| 23 | 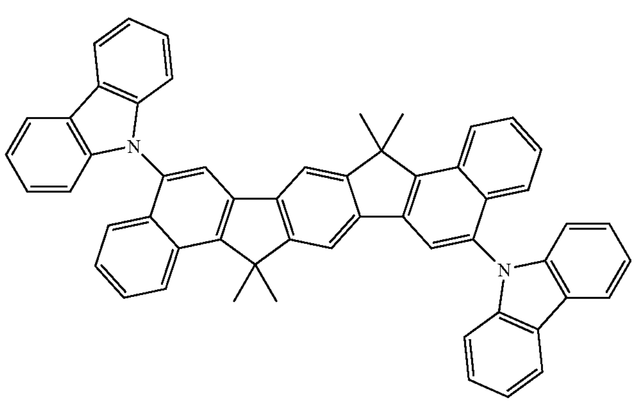 [SMILES: CC1(C)c2cc3c(cc2-c2cc(-n4c5ccccc5c5ccccc54)c4ccccc4c21)C(C)(C)c1c-3cc(-n2c3ccccc3c3ccccc32)c2ccccc12] | 59 |

Example 24

Synthesis of 2,7-bis(4-triphenylamino)-3,4,8,9-dibenzo-6,6,12,12-tetramethyl-6,12-dihydroindeno[1,2-b]fluorene

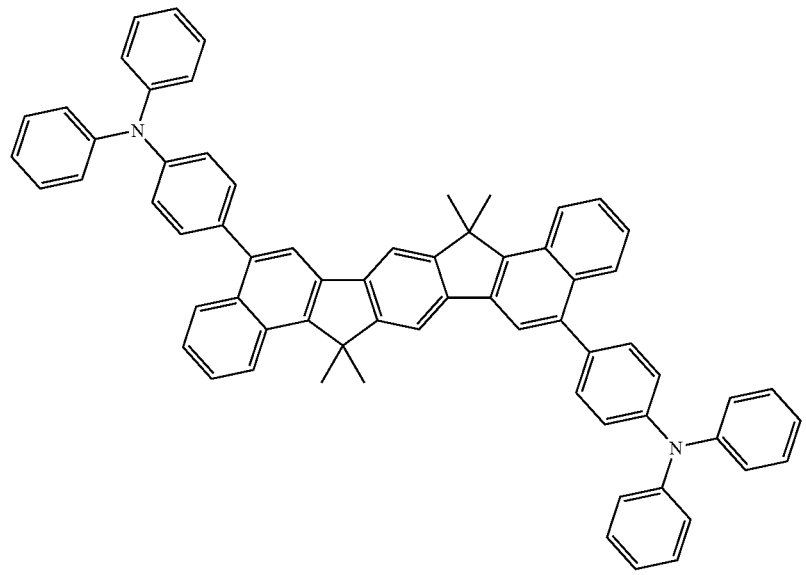 [SMILES: CC1(C)c2cc3c(cc2-c2cc(-c4ccc(N(c5ccccc5)c5ccccc5)cc4)c4ccccc4c21)C(C)(C)c1c-3cc(-c2ccc(N(c3ccccc3)c3ccccc3)cc2)c2ccccc12]

The compound is prepared analogously to Example 10 starting from 2-naphthaleneboronic acid instead of 1-naphthaleneboronic acid and is purified by recrystallisation four times from NMP and subsequent sublimation (390° C., $2\times10^{-3}$ mbar). The yield for the Suzuki reaction is 77% with a purity of >99.9% (HPLC).

The following compounds are prepared analogously to the process described above (yields after sublimation with a purity of >99.9%) (Examples 25 to 27).

| Ex. | Structure | Yield (%) |
|---|---|---|
| 25 | 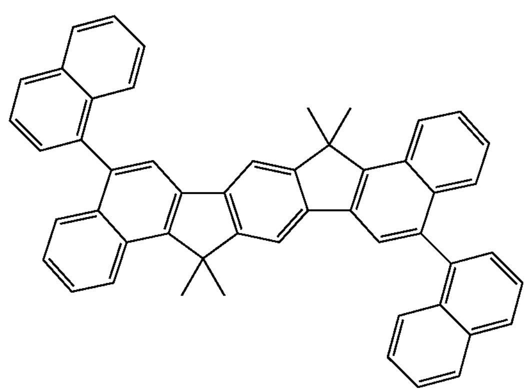 [SMILES: CC1(C)c2cc3c(cc2-c2cc(-c4cccc5ccccc45)c4ccccc4c21)C(C)(C)c1c-3cc(-c2cccc3ccccc23)c2ccccc12] | 58 |
| 26 | 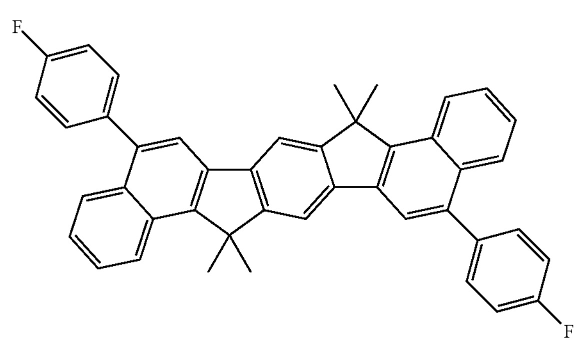 [SMILES: CC1(C)c2cc3c(cc2-c2cc(-c4ccc(F)cc4)c4ccccc4c21)C(C)(C)c1c-3cc(-c2ccc(F)cc2)c2ccccc12] | 82 |

-continued

| Ex. | Structure | Yield (%) |
|---|---|---|
| 27 | 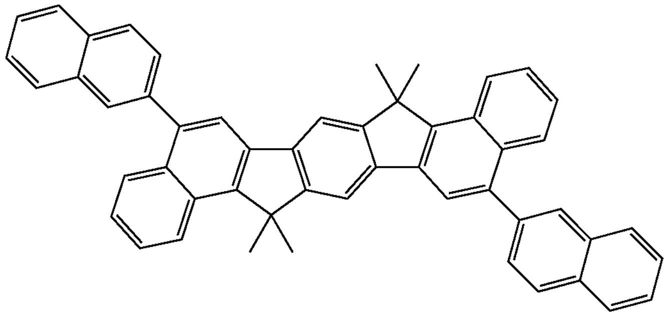 [SMILES: CC1(C)c2cc3c(cc2-c2cc(-c4ccc5ccccc5c4)c4ccccc4c21)C(C)(C)c1c-3cc(-c2ccc3ccccc3c2)c2ccccc12] | 78 |

Example 28

Production of OLEDs

OLEDs are produced by a general process as described in WO 04/058911, which is matched in individual cases to the particular circumstances (for example layer-thickness variation in order to achieve optimum efficiency or colour).

The results for various OLEDs are presented in Examples 29 to 47 below. Glass plates coated with structured ITO (indium tin oxide) form the substrates. For improved processing, PEDOT (spin-coated from water; purchased from H. C. Starck, Goslar, Germany; poly(3,4-ethylenedioxy-2,5-thiophene)) is applied directly to the substrate. The OLEDs always consist of the following layer sequence: substrate/PEDOT 20 nm/hole-injection layer (HIL 1) 20 nm/hole-transport layer (HTM1) 20 nm/emission layer (EML) 30 nm/electron-transport layer (ETM) 20 nm and finally a cathode. The materials apart from PEDOT are thermally vapour-deposited in a vacuum chamber. The EML here always consists of a matrix material (host, abbreviated to H) and a dopant (guest or dopant, abbreviated to D), which is admixed with the host by co-evaporation. The cathode is formed by a 1 nm thin LiF layer and a 100 nm Al layer deposited on top. Table 1 shows the structures of the materials used.

TABLE I

Structures of the materials used

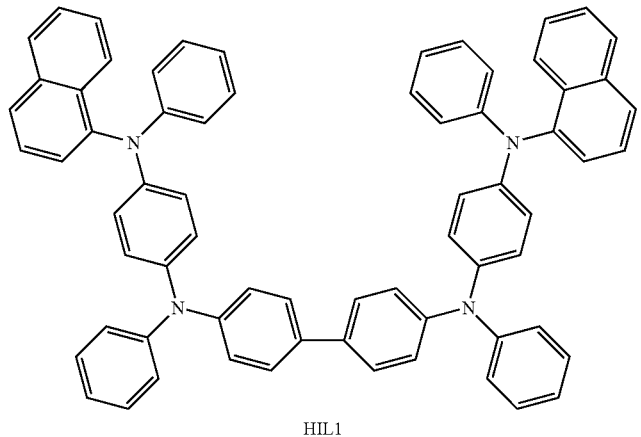

HIL1

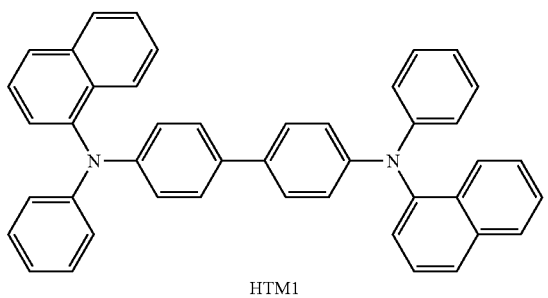

HTM1

TABLE I-continued
Structures of the materials used
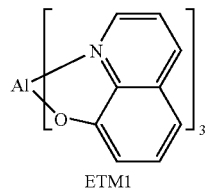
ETM1
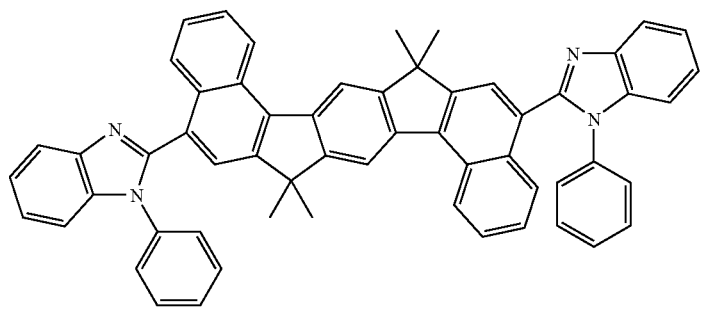 [SMILES: CC1(C)c2cc3c(cc2-c2c1cc(-c1nc4ccccc4n1-c1ccccc1)c1ccccc21)C(C)(C)c1cc(-c2nc4ccccc4n2-c2ccccc2)c2ccccc2c1-3]
ETM2
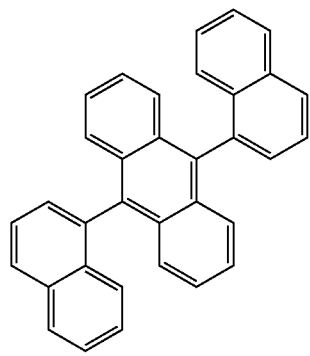 [SMILES: c1ccc2c(-c3c4ccccc4c(-c4cccc5ccccc45)c4ccccc34)cccc2c1]
H1
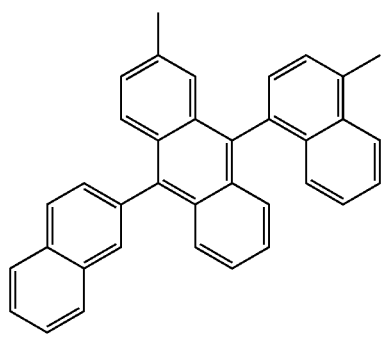 [SMILES: Cc1ccc2c(-c3ccc4ccccc4c3)c3ccccc3c(-c3ccc(C)c4ccccc34)c2c1]
H2

TABLE I-continued
Structures of the materials used
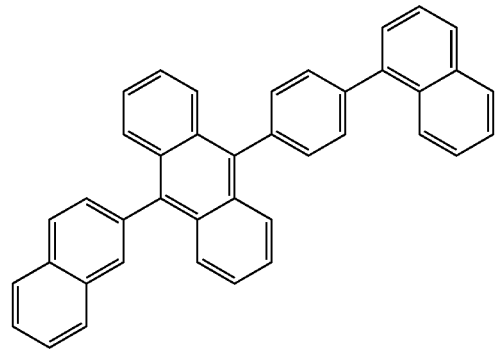 [SMILES: c1ccc2cc(-c3c4ccccc4c(-c4ccc(-c5cccc6ccccc56)cc4)c4ccccc34)ccc2c1]
H3
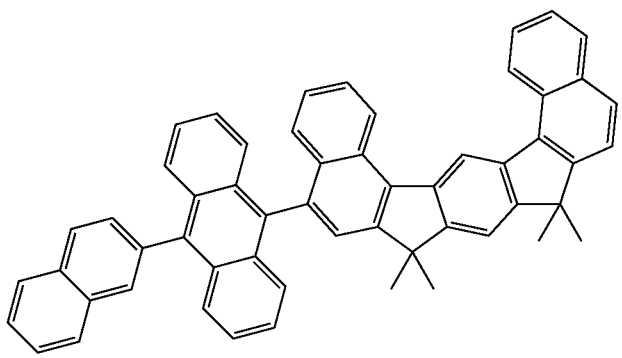 [SMILES: CC1(C)c2cc3c(cc2-c2c1ccc1ccccc21)-c1c(cc(-c2c4ccccc4c(-c4ccc5ccccc5c4)c4ccccc24)c2ccccc12)C3(C)C]
H4
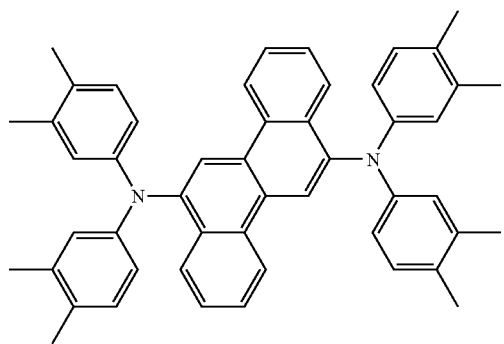
D1
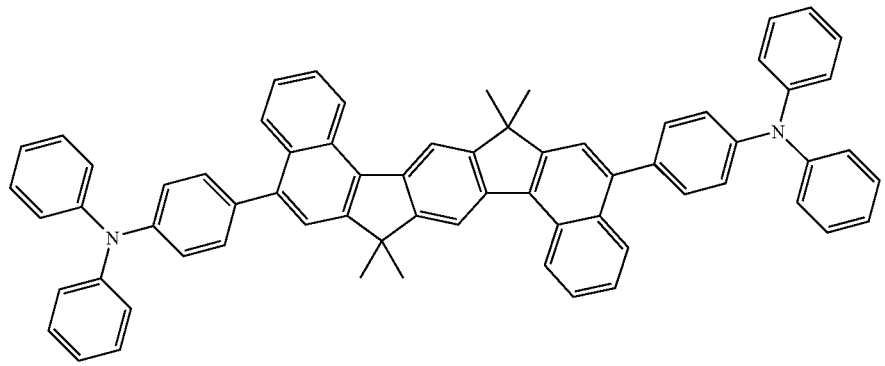 [SMILES: CC1(C)c2cc3c(cc2-c2c1cc(-c1ccc(N(c4ccccc4)c4ccccc4)cc1)c1ccccc21)C(C)(C)c1cc(-c2ccc(N(c4ccccc4)c4ccccc4)cc2)c2ccccc2c1-3]
D2

TABLE I-continued
Structures of the materials used
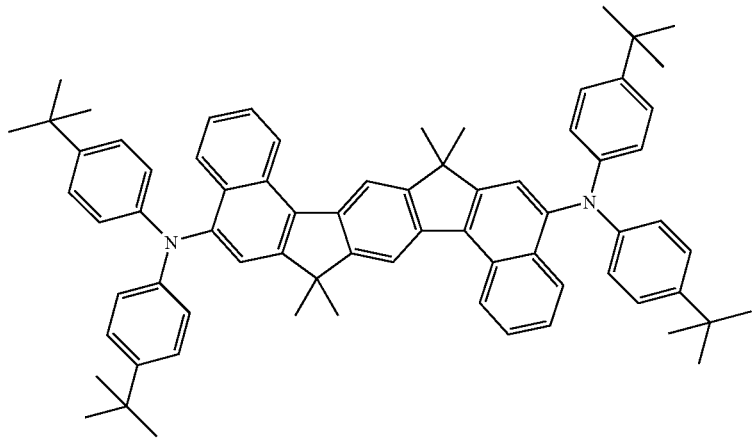 [SMILES: CC(C)(C)c1ccc(N(c2ccc(C(C)(C)C)cc2)c2cc3c(c4ccccc24)-c2cc4c(cc2C3(C)C)-c2c(cc(N(c3ccc(C(C)(C)C)cc3)c3ccc(C(C)(C)C)cc3)c3ccccc23)C4(C)C)cc1]
D3
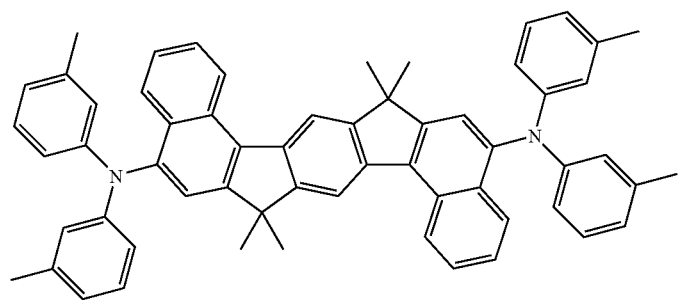
D4
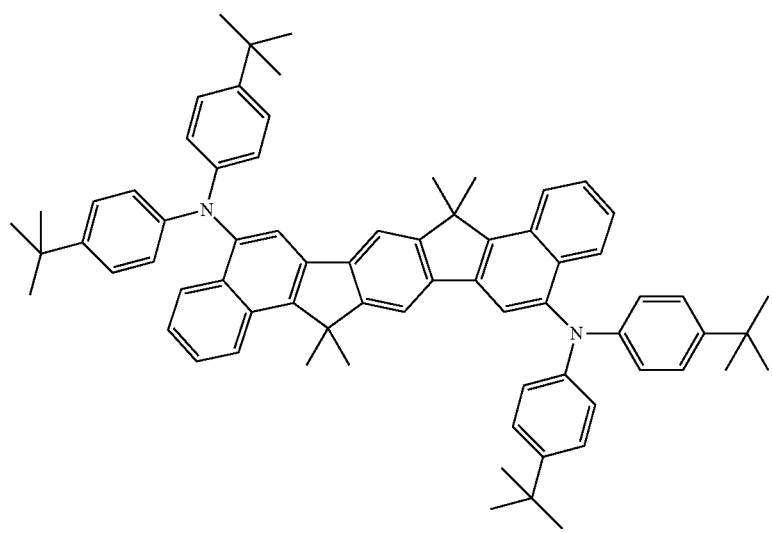 [SMILES: CC(C)(C)c1ccc(N(c2ccc(C(C)(C)C)cc2)c2cc3c(c4ccccc24)C(C)(C)c2cc4c(cc2-3)C(C)(C)c2c-4cc(N(c3ccc(C(C)(C)C)cc3)c3ccc(C(C)(C)C)cc3)c3ccccc23)cc1]
D5

TABLE I-continued

Structures of the materials used

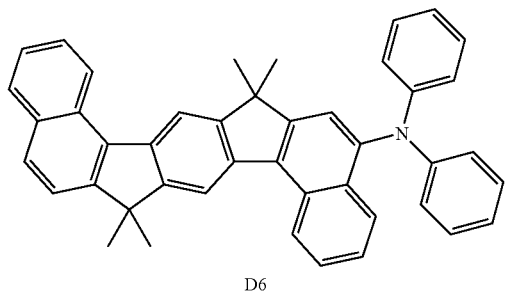

D6

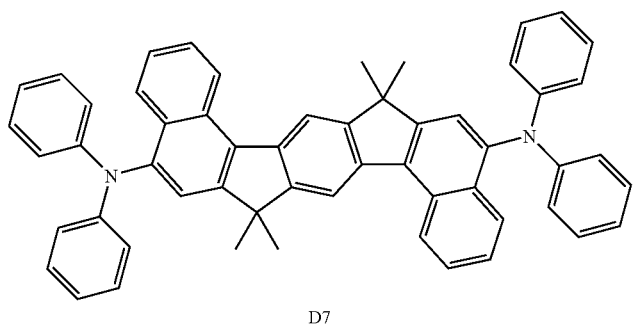

D7

ETM-1 here is an electron-transport material in accordance with the prior art. ETM-2 is an electron-transport material according to the invention. H1, H2 and H3 are host materials in accordance with the prior art. H4 is a host material according to the invention. D1 is a dopant in accordance with the prior art. D2, D3, D4, D5, D6 and D7 are dopants according to the invention.

The OLEDs described above are characterised by standard methods; for this purpose, the electroluminescence spectra, the efficiency (measured in cd/A), the power efficiency (measured in lm/W) as a function of the luminance, calculated from current/voltage/luminance characteristics (IUL characteristics), and the lifetime are determined. The lifetime is defined as the time after which the initial luminance of 2000 cd/m² has dropped to half.

Table 2 shows the layer structures (Examples 29 to 47) for some OLEDs and their results.

TABLE 2

Layer structures and results for OLEDs

| Ex. | EML | ETL | Max. efficiency (cd/A) | Voltage (V) at 1000 cd/m² | CIE | Lifetime (h) at 2000 cd/m² |
|---|---|---|---|---|---|---|
| 29 [a] | H3 + 5% D1 | ETM1 | 6.9 | 5.8 | x = 0.15/y = 0.20 | 2200 |
| 30 | H4 + 5% D1 | ETM1 | 7.3 | 5.6 | x = 0.15/y = 0.19 | 2200 |
| 31 | H3 + 5% D1 | ETM2 | 7.5 | 5.3 | x = 0.15/y = 0.19 | 2600 |
| 32 | H1 + 5% D2 | ETM1 | 7.0 | 5.7 | x = 0.16/y = 0.20 | 2400 |
| 33 | H3 + 5% D2 | ETM1 | 7.2 | 5.3 | x = 0.14/y = 0.19 | 3100 |
| 34 | H4 + 5% D2 | ETM2 | 7.5 | 5.2 | x = 0.14/y = 0.19 | 2900 |
| 35 | H1 + 5% D3 | ETM1 | 21.4 | 5.1 | x = 0.18/y = 0.42 | 6300 |
| 36 | H2 + 5% D3 | ETM1 | 18.4 | 5.2 | x = 0.18/y = 0.43 | 7200 |
| 37 | H3 + 5% D3 | ETM1 | 20.2 | 5.3 | x = 0.18/y = 0.42 | 7500 |
| 38 | H1 + 5% D4 | ETM1 | 12.3 | 5.5 | x = 0.15/y = 0.30 | 5200 |
| 39 | H3 + 5% D4 | ETM1 | 12.7 | 5.4 | x = 0.14/y = 0.29 | 5300 |
| 40 | H3 + 5% D4 | ETM2 | 13.8 | 5.2 | x = 0.14/y = 0.29 | 5800 |
| 41 | H1 + 5% D5 | ETM1 | 9.2 | 5.6 | x = 0.15/y = 0.26 | 3100 |
| 42 | H2 + 5% D5 | ETM2 | 10.8 | 5.3 | x = 0.14/y = 0.26 | 3700 |
| 43 | H3 + 5% D5 | ETM2 | 9.9 | 5.5 | x = 0.14/y = 0.26 | 3800 |
| 44 | H1 + 5% D6 | ETM1 | 6.2 | 5.7 | x = 0.15/y = 0.14 | 2000 |
| 45 | H2 + 5% D6 | ETM1 | 6.0 | 5.6 | x = 0.14/y = 0.13 | 2200 |
| 46 | H3 + 5% D6 | ETM2 | 6.1 | 5.6 | x = 0.14/y = 0.13 | 2400 |
| 47 | H3 + 5% D7 | ETM2 | 12.6 | 5.3 | x = 0.14/y = 0.28 | 5900 |

[a] Comparative experiment in accordance with the prior art.

As can be seen from the results in Table 2, the OLEDs according to the invention have longer lifetimes than the OLEDs in accordance with the prior art (Example 29).

The invention claimed is:

1. A compound of the formula (1) to formula (4)

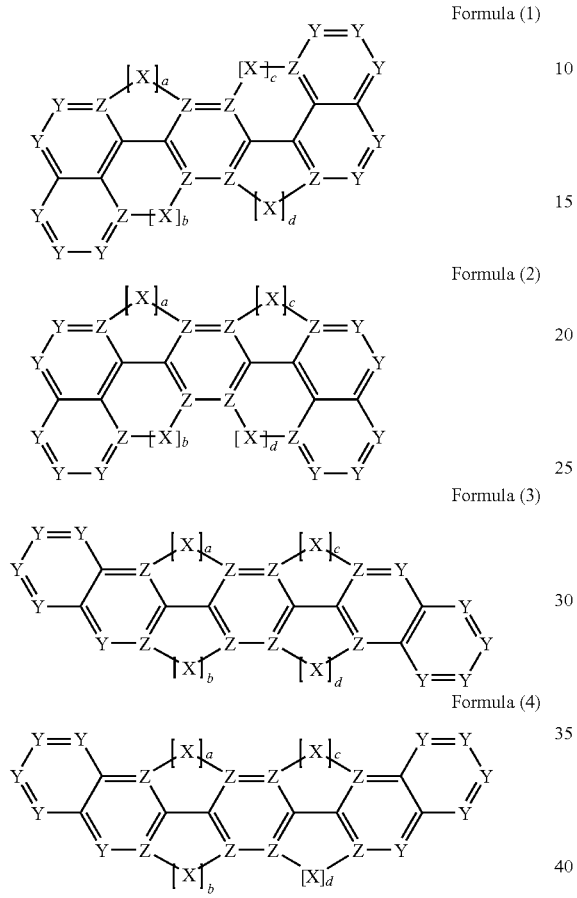

wherein
- Y is on each occurrence, identically or differently, $CR^1$ or N;
- Z is equal to C if a bridge X is bonded to the group Z and is equal to Y if no bridge X is bonded to the group Z;
- X is on each occurrence, identically or differently, a divalent bridge selected from the group consisting of $C(R^1)_2$, C=O, C=$NR^1$, O, S, S=O, $SO_2$, $NR^{100}$ and P(=O)$R^1$;
- $R^1$ is on each occurrence, identically or differently, H, F, Cl, Br, I, $N(Ar)_2$, C(=O)Ar, P(=O)$Ar_2$, S(=O)Ar, S(=O)$_2$Ar, $CR^2$=$CR^2$Ar, CN, $NO_2$, Si($R^2$)$_3$, B(O$R^2$)$_2$, OS$O_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$ and in which one or more non-adjacent $CH_2$ groups may be replaced by $R^2C$=$CR^2$, C≡C, Si($R^2$)$_2$, Ge($R^2$)$_2$, Sn($R^2$)$_2$, C=O, C=S, C=Se, C=$NR^2$, P(=O)($R^2$), SO, $SO_2$, $NR^2$, O, S or $CONR^2$ and in which one or more H atoms is optionally replaced by F, Cl, Br, I, CN or $NO_2$, or an aromatic or heteroaromatic ring system having 5 to 40 aromatic ring atoms, which optionally in each case be substituted by one or more radicals $R^2$, or an aryloxy or heteroaryloxy group having 5 to 40 aromatic ring atoms, which is optionally substituted by one or more radicals $R^2$, or a combination of these systems; two or more adjacent substituents $R^1$ here optionally form a mono- or polycyclic aliphatic or aromatic ring system with one another and with the proviso that at least one $R^1$ is not hydrogen;
- $R^{100}$ is on each occurrence, identically or differently, C(=O)Ar, P(=O)$Ar_2$, S(=O)Ar, S(=O)$_2$Ar, or a heteroaromatic ring system having 5 to 40 aromatic ring atoms, which optionally in each case be substituted by one or more radicals $R^2$, or a combination of these systems; two or more adjacent substituents $R^{100}$ here optionally form a mono- or polycyclic aliphatic or aromatic ring system with one another;
- Ar is on each occurrence, identically or differently, an aromatic or heteroaromatic ring system having 5-30 aromatic ring atoms, which is optionally substituted by one or more non-aromatic radicals $R^1$; two radicals Ar here on the same nitrogen or phosphorus atom are optionally linked to one another by a single bond or a bridge X;
- $R^2$ is on each occurrence, identically or differently, H or an aliphatic, aromatic and/or heteroaromatic hydrocarbon radical having 1 to 20 C atoms, in which, in addition, H atoms is optionally replaced by F; two or more adjacent substituents $R^2$ here optionally forms a mono- or polycyclic aliphatic or aromatic ring system with one another;
- a, b, c and d are on each occurrence, identically or differently, 0 or 1, with the proviso that a+b=1 or 2 and c+d=1 or 2, where a=0 and b=0 and c=0 and d=0 in each case means that the corresponding bridge X is not present;
- with the exception of the following compounds:

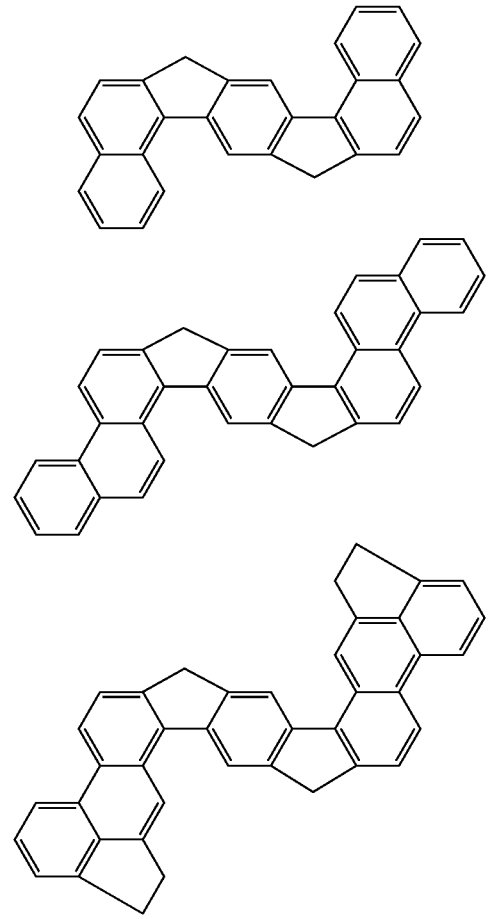

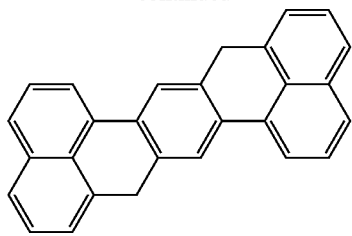
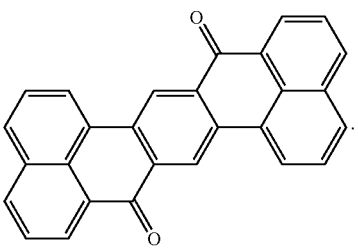
2. The compound according to claim 1, wherein a+b=1 and c+d=1.
3. The compound according to claim 1, wherein the compound is selected from the compound of the formula (5), (6), (7), (8), (9), (10), (11), (12), (13), (14), (15) or (16)
Formula (5)
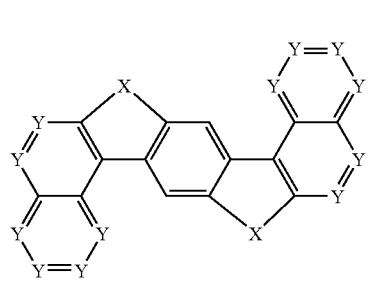
Formula (6)
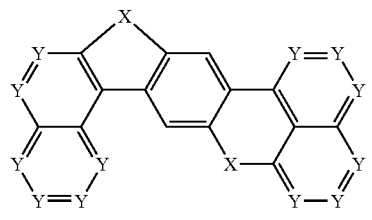
Formula (7)
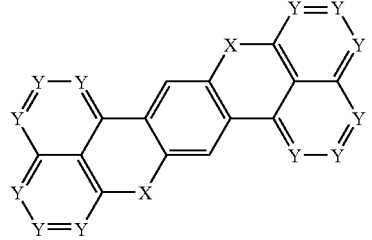
Formula (8)
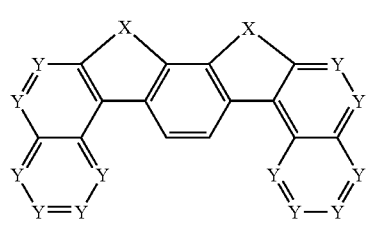
Formula (9)
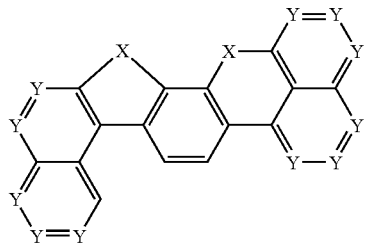
Formula (10)
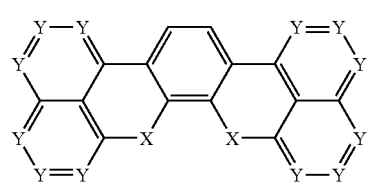
Formula (11)
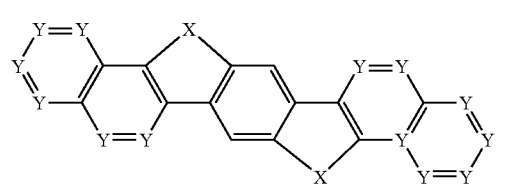
Formula (12)
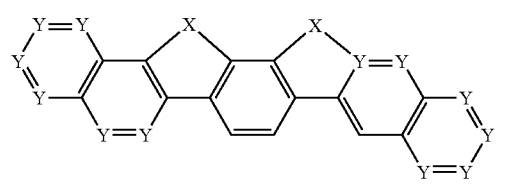
Formula (13)
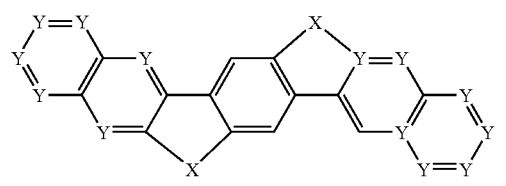
Formula (14)
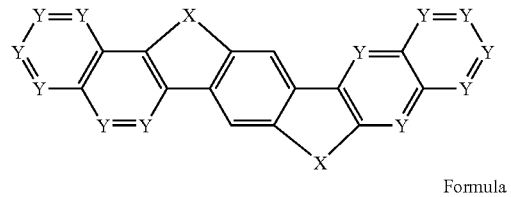
Formula (15)
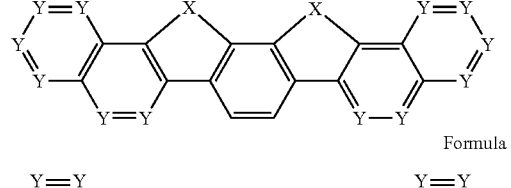
Formula (16)
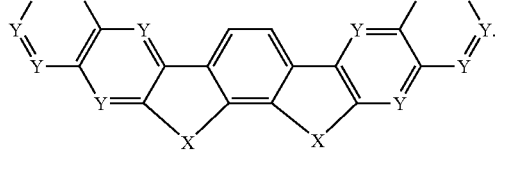

4. The compound according to claim 1, wherein the symbol Y stands for nitrogen a total of 0, 1, 2, 3 or 4 times, where the other symbols Y stand for $CR^1$.

5. The compound according to claim 1, wherein the compound is selected from the formulae (5a), (6a), (7a), (8a), (9a), (10a) or (11a)

Formula (5a)

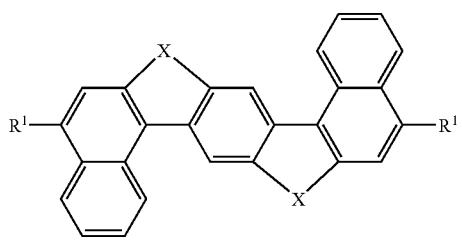

Formula (6a)

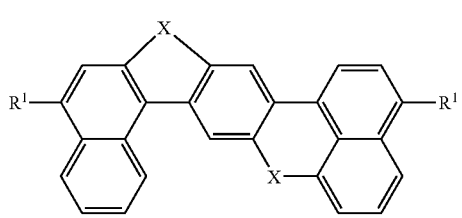

Formula (7a)

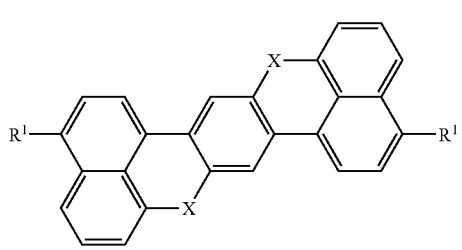

Formula (8a)

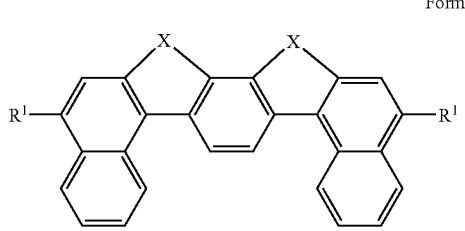

Formula (9a)

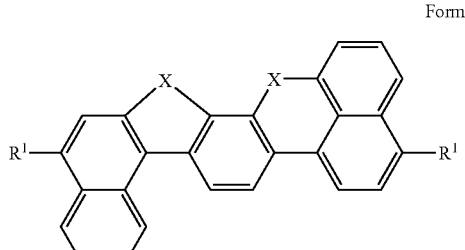

Formula (10a)

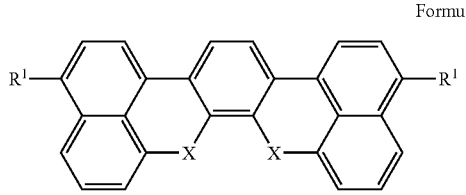

Formula (11a)

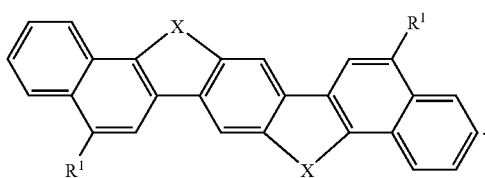

6. The compound according to claim 1, wherein $R^1$, identically or differently on each occurrence, stands for H, F, Br, C(=O)Ar, P(=O)Ar$_2$, $CR^2$=$CR^2$Ar, a straight-chain alkyl group having 1 to 5 C atoms or a branched alkyl group having 3 to 5 C atoms, in which one or more non-adjacent $CH_2$ groups is optionally replaced by —$R^2C$=$CR^2$—, —C≡C— or —O— and in which one or more H atoms is optionally replaced by F, or an aryl group having 6 to 16 C atoms or a heteroaryl group having 2 to 16 C atoms or a spirobifluorene group, each of which is optionally substituted by one or more radicals $R^2$, or a combination of two or three of these systems, and/or in that at least one symbol $R^1$ stands for a group N(Ar)$_2$ of the formula (17) or (18)

Formula (17)

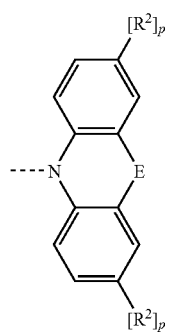

Formula (18)

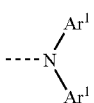

where $R^2$ has the meaning mentioned in claim 1 and furthermore:

E is a single bond, O, S, N($R^2$) or C($R^2$)$_2$;

$Ar^1$ is, identically or differently on each occurrence, an aryl or heteroaryl group having 5 to 20 aromatic ring atoms or a triarylamine group having 15 to 30 aromatic ring atoms, each of which is optionally substituted by one or more radicals $R^2$, each of which is optionally substituted by one or more radicals $R^2$;

p is on each occurrence, identically or differently, 0 or 1.

7. The compound according to claim 1, wherein $Ar^1$ is an aryl or heteroaryl group having 6 to 14 aromatic ring atoms or a triarylamine group having 18 to 22 aromatic ring atoms, each of which is optionally substituted by one or more radicals $R^2$.

8. The compound according to claim 1, wherein the symbol X is on each occurrence, identically or differently, a divalent bridge selected from the group consisting of C($R^1$)$_2$, C=O, C=$NR^1$, O, S, S=O, SO$_2$, and P(=O)$R^1$.

9. The compound according to claim 1, wherein radicals $R^1$ which are bonded to the bridges X are identical or different and are selected from H, straight-chain alkyl groups having 1 to 5 C atoms or branched alkyl groups having 3 to 5 C atoms, in which one or more non-adjacent $CH_2$ groups is optionally replaced by $-R^2C=CR^2-$, $-C\equiv C-$ or $-O-$ and in which one or more H atoms is optionally replaced by F, or aryl groups having 6 to 16 C atoms or heteroaryl groups having 2 to 16 C atoms, each of which is optionally substituted by one or more radicals $R^2$, or a combination of two or three of these systems; two of the radicals $R^1$ which are bonded to the same bridge atom here optionally forms a ring system with one another.

10. The compound according to claim 1, wherein X is on each occurrence, identically or differently, a divalent bridge selected from the group consisting of $C(R^1)_2$, $C=O$ and $C=NR^1$.

11. A process for the preparation of the compound according to claim 1, comprising the steps:
   a) coupling of a functionalised naphthalene to a tetrafunctionalised benzene derivative;
   b) ring closure with acid catalysis; and
   c) functionalisation of the parent structure obtained by steps a) and b) by bromination, followed by Hartwig-Buchwald coupling to an aromatic amine or Suzuki coupling to an arylboronic acid or an arylboronic acid derivative.

12. An organic electronic device comprising at least one compound of the formula (1) to formula (4)

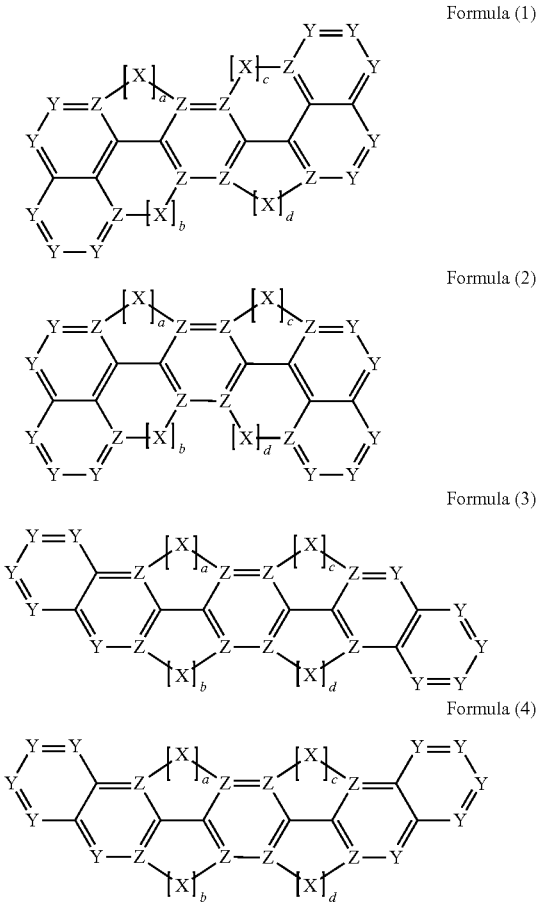

wherein
Y is on each occurrence, identically or differently, $CR^1$ or N;

Z is equal to C if a bridge X is bonded to the group Z and is equal to Y if no bridge X is bonded to the group Z;

X is on each occurrence, identically or differently, a divalent bridge selected from the group consisting of $C(R^1)_2$, $C=O$, $C=NR^1$, O, S, $S=O$, $SO_2$, $NR^{100}$ and $P(=O)R^1$;

$R^1$ is on each occurrence, identically or differently, H, F, Cl, Br, I, $N(Ar)_2$, $C(=O)Ar$, $P(=O)Ar_2$, $S(=O)Ar$, $S(=O)_2Ar$, $CR^2=CR^2Ar$, CN, $NO_2$, $Si(R^2)_3$, $B(OR^2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$ and in which one or more non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and in which one or more H atoms is optionally replaced by F, Cl, Br, I, CN or $NO_2$, or an aromatic or heteroaromatic ring system having 5 to 40 aromatic ring atoms, which optionally in each case be substituted by one or more radicals $R^2$, or an aryloxy or heteroaryloxy group having 5 to 40 aromatic ring atoms, which is optionally substituted by one or more radicals $R^2$, or a combination of these systems; two or more adjacent substituents $R^1$ here optionally form a mono- or polycyclic aliphatic or aromatic ring system with one another;

$R^{100}$ is on each occurrence, identically or differently, $C(=O)Ar$, $P(=O)Ar_2$, $S(=O)Ar$, $S(=O)_2Ar$, or a heteroaromatic ring system having 5 to 40 aromatic ring atoms, which optionally in each case be substituted by one or more radicals $R^2$, or a combination of these systems; two or more adjacent substituents $R^{100}$ here optionally form a mono- or polycyclic aliphatic or aromatic ring system with one another;

Ar is on each occurrence, identically or differently, an aromatic or heteroaromatic ring system having 5-30 aromatic ring atoms, which is optionally substituted by one or more non-aromatic radicals $R^1$; two radicals Ar here on the same nitrogen or phosphorus atom are optionally linked to one another by a single bond or a bridge X;

$R^2$ is on each occurrence, identically or differently, H or an aliphatic, aromatic and/or heteroaromatic hydrocarbon radical having 1 to 20 C atoms, in which, in addition, H atoms is optionally replaced by F; two or more adjacent substituents $R^2$ here optionally forms a mono- or polycyclic aliphatic or aromatic ring system with one another;

a, b, c and d are on each occurrence, identically or differently, 0 or 1, with the proviso that a+b=1 or 2 and c+d=1 or 2, where a=0 and b=0 and c=0 and d=0 in each case means that the corresponding bridge X is not present;

with the exception of the following compounds:

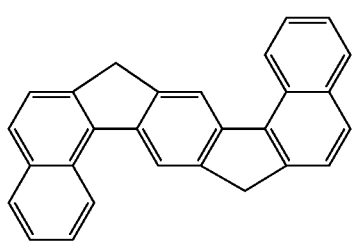

-continued

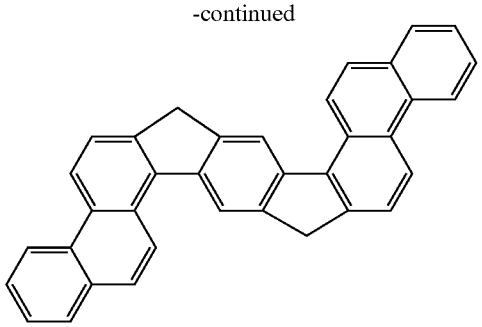

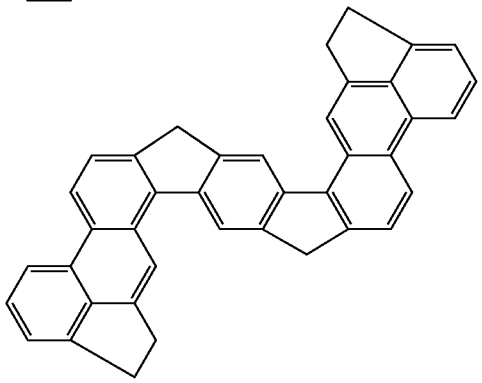

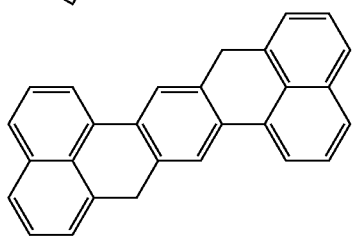

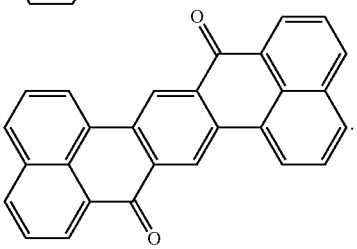

13. The organic electronic device as claimed in claim 12 further comprising an anode, cathode and wherein said at least one compound is in at least one organic layer.

14. A polymer, oligomer or dendrimer containing one or more compounds according to claim 1, wherein one or more radicals $R^1$ represent bonds to the polymer, oligomer or dendrimer.

15. The organic electronic device according to claim 12 selected from organic electroluminescent devices (OLEDs, PLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) and organic photo receptors.

16. The organic electronic device according to claim 15, wherein the device is an organic electroluminescent device comprising cathode, anode, one or more emitting layers and optionally further layers selected from hole-injection layer, hole-transport layer, electron-transport layer, electron-injection layer and/or charge-generation layer.

17. An organic electronic device selected from the group consisting of organic electroluminescent devices (OLEDs, PLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) and organic photo receptors wherein said device comprises a cathode, an anode, one or more emitting layers and optionally further layers selected from hole-injection layer, hole-transport layer, electron-transport layer, electron-injection layer and/or charge-generation layer wherein one or more substituents $R^1$ are selected from simple or condensed aryl or heteroaryl groups, and a compound of the formula (1) to formula (4)

Formula (1)

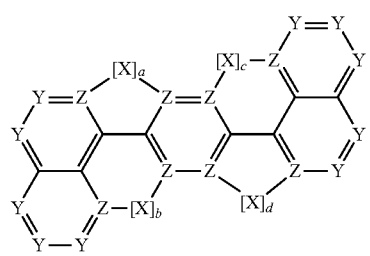

Formula (2)

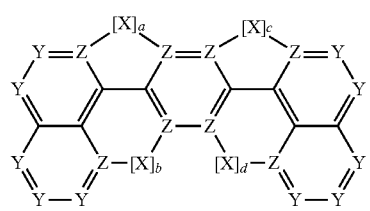

Formula (3)

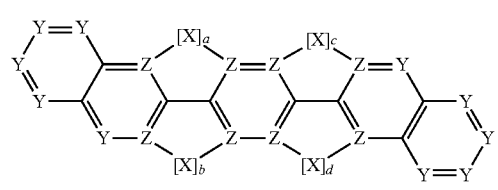

Formula (4)

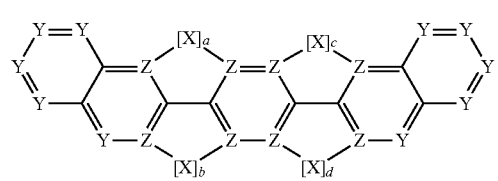

wherein
Y is on each occurrence, identically or differently, $CR^1$ or N;
Z is equal to C if a bridge X is bonded to the group Z and is equal to Y if no bridge X is bonded to the group Z;
X is on each occurrence, identically or differently, a divalent bridge selected from the group consisting of $C(R^1)_2$, C=O, C=$NR^1$, O, S, S=O, $SO_2$, $NR^{100}$ and P(=O)$R^1$;
$R^1$ is on each occurrence, identically or differently, H, F, Cl, Br, I, $N(Ar)_2$, C(=O)Ar, P(=O)$Ar_2$, S(=O)Ar, S(=O)$_2$Ar, $CR^2$=$CR^2$Ar, CN, $NO_2$, Si($R^2$)$_3$, B(OR$^2$)$_2$, OSO$_2$R$^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$ and in which one or more non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, $SO$, $SO_2$, $NR^2$, $O$, $S$ or $CONR^2$ and in which one or more H atoms is optionally replaced by F, Cl, Br, I, CN or $NO_2$, or an aromatic or heteroaromatic ring system having 5 to 40 aromatic ring atoms, which optionally in each case be substituted by one or more radicals $R^2$, or an aryloxy or heteroaryloxy group having 5 to 40 aromatic ring atoms, which is optionally substituted by one or more radicals $R^2$, or a combination of these systems; two or more adjacent substituents $R^1$ here optionally form a mono- or polycyclic aliphatic or aromatic ring system with one another;

$R^{100}$ is on each occurrence, identically or differently, $C(=O)Ar$, $P(=O)Ar_2$, $S(=O)Ar$, $S(=O)_2Ar$, or a heteroaromatic ring system having 5 to 40 aromatic ring atoms, which optionally in each case be substituted by one or more radicals $R^2$, or a combination of these systems; two or more adjacent substituents $R^{100}$ here optionally form a mono- or polycyclic aliphatic or aromatic ring system with one another;

Ar is on each occurrence, identically or differently, an aromatic or heteroaromatic ring system having 5-30 aromatic ring atoms, which is optionally substituted by one or more non-aromatic radicals $R^1$; two radicals Ar here on the same nitrogen or phosphorus atom are optionally linked to one another by a single bond or a bridge X;

$R^2$ is on each occurrence, identically or differently, H or an aliphatic, aromatic and/or heteroaromatic hydrocarbon radical having 1 to 20 C atoms, in which, in addition, H atoms is optionally replaced by F; two or more adjacent substituents $R^2$ here optionally forms a mono- or polycyclic aliphatic or aromatic ring system with one another;

a, b, c and d are on each occurrence, identically or differently, 0 or 1, with the proviso that a+b=1 or 2 and c+d=1 or 2, where a=0 and b=0 and c=0 and d=0 in each case means that the corresponding bridge X is not present;

with the exception of the following compounds:

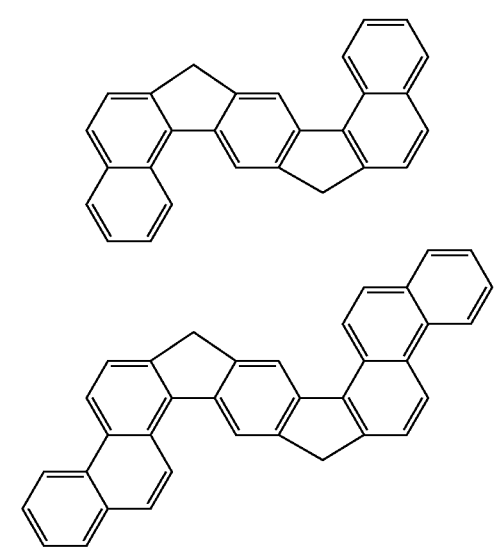

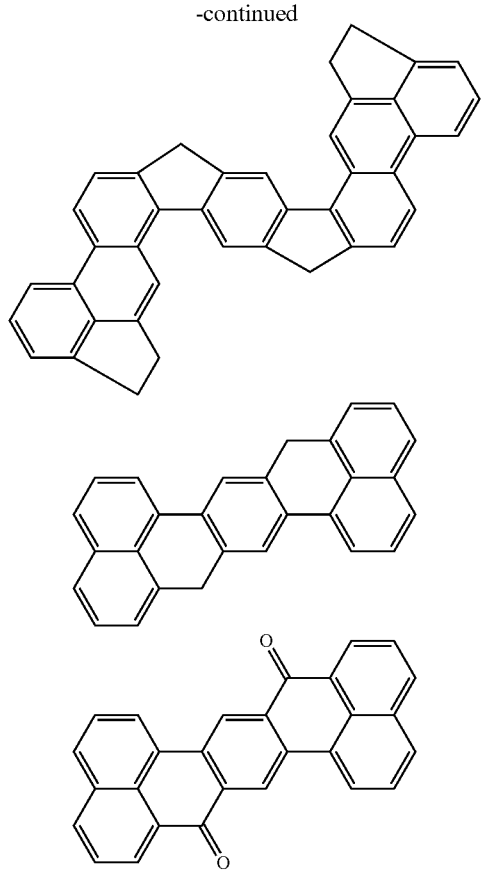

is employed in at least one of the following:
(a) the compound of the formula (1) to formula (4) is employed as host for a fluorescent dopant and/or in that one or more substituents $R^1$ and/or bridges X contain at least one group $C=O$, $P(=O)$ and/or $SO_2$,
(b) the compound of the formula (1) to formula (4) is employed as matrix for phosphorescent dopants and/or in that one or more substituents $R^1$ contain at least one vinylaryl unit, at least one vinylarylamine unit and/or at least one arylamino unit,
(c) the compounds of the formula (1) to formula (4) are employed as emitting materials and/or in that one or more substituents $R^1$ stand for a group $N(Ar)_2$,
(d) the compound of the formula (1) to formula (4) may optionally be doped with electron-acceptor compounds and in that the compound is employed as hole-transport material or as hole-injection material, and/or in that one or more substituents $R^1$ contain at least one unit $C=O$, $P(=O)$ and/or $SO_2$, or
(e) the compound of the formula (1) to formula (4) may optionally be doped with an electron-donor compound and are employed as electron-transport material.

18. An organic electronic device selected from the group consisting of organic electroluminescent devices (OLEDs, PLEDs), organic field-effect transistors (O-FETs organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) and organic photo receptors wherein said device comprises a cathode, an anode, one or more emitting layers and optionally further layers selected from hole-injection layer, hole-transport layer, electron-transport layer, electron-injection layer and/or charge-generation layer wherein one or more substituents $R^1$ are selected from simple or condensed aryl or heteroaryl groups, and the compound of the formula (1) to formula (4)

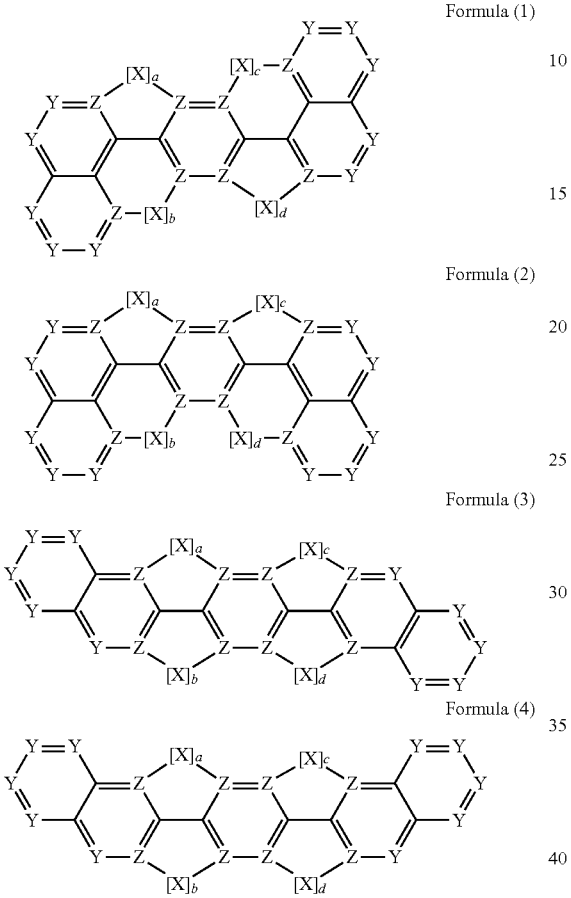

Formula (1)

Formula (2)

Formula (3)

Formula (4)

wherein
- Y is on each occurrence, identically or differently, $CR^1$ or N;
- Z is equal to C if a bridge X is bonded to the group Z and is equal to Y if no bridge X is bonded to the group Z;
- X is on each occurrence, identically or differently, a divalent bridge selected from the group consisting of $C(R^1)_2$, C=O, C=NR$^1$, O, S, S=O, SO$_2$, NR$^{100}$ and P(=O)R$^1$;
- $R^1$ is on each occurrence, identically or differently, H, F, Cl, Br, I, N(Ar)$_2$, C(=O)Ar, P(=O)Ar$_2$, S(=O)Ar, S(=O)$_2$Ar, $CR^2$=$CR^2$Ar, CN, NO$_2$, Si($R^2$)$_3$, B(OR$^2$)$_2$, OSO$_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$ and in which one or more non-adjacent CH$_2$ groups may be replaced by $R^2$C=$CR^2$, C≡C, Si($R^2$)$_2$, Ge($R^2$)$_2$, Sn($R^2$)$_2$, C=O, C=S, C=Se, C=NR$^2$, P(=O)($R^2$), SO, SO$_2$, NR$^2$, O, S or CONR$^2$ and in which one or more H atoms is optionally replaced by F, Cl, Br, I, CN or NO$_2$, or an aromatic or heteroaromatic ring system having 5 to 40 aromatic ring atoms, which optionally in each case be substituted by one or more radicals $R^2$, or an aryloxy or heteroaryloxy group having 5 to 40 aromatic ring atoms, which is optionally substituted by one or more radicals $R^2$, or a combination of these systems; two or more adjacent substituents $R^1$ here optionally form a mono- or polycyclic aliphatic or aromatic ring system with one another;
- $R^{100}$ is on each occurrence, identically or differently, C(=O)Ar, P(=O)Ar$_2$, S(=O)Ar, S(=O)$_2$Ar, or a heteroaromatic ring system having 5 to 40 aromatic ring atoms, which optionally in each case be substituted by one or more radicals $R^2$, or a combination of these systems; two or more adjacent substituents $R^{100}$ here optionally form a mono- or polycyclic aliphatic or aromatic ring system with one another;
- Ar is on each occurrence, identically or differently, an aromatic or heteroaromatic ring system having 5-30 aromatic ring atoms, which is optionally substituted by one or more non-aromatic radicals $R^1$; two radicals Ar here on the same nitrogen or phosphorus atom are optionally linked to one another by a single bond or a bridge X;
- $R^2$ is on each occurrence, identically or differently, H or an aliphatic, aromatic and/or heteroaromatic hydrocarbon radical having 1 to 20 C atoms, in which, in addition, H atoms is optionally replaced by F; two or more adjacent substituents $R^2$ here optionally forms a mono- or polycyclic aliphatic or aromatic ring system with one another;
- a, b, c and d are on each occurrence, identically or differently, 0 or 1, with the proviso that a+b=1 or 2 and c+d=1 or 2, where a=0 and b=0 and c=0 and d=0 in each case means that the corresponding bridge X is not present;
with the exception of the following compounds:

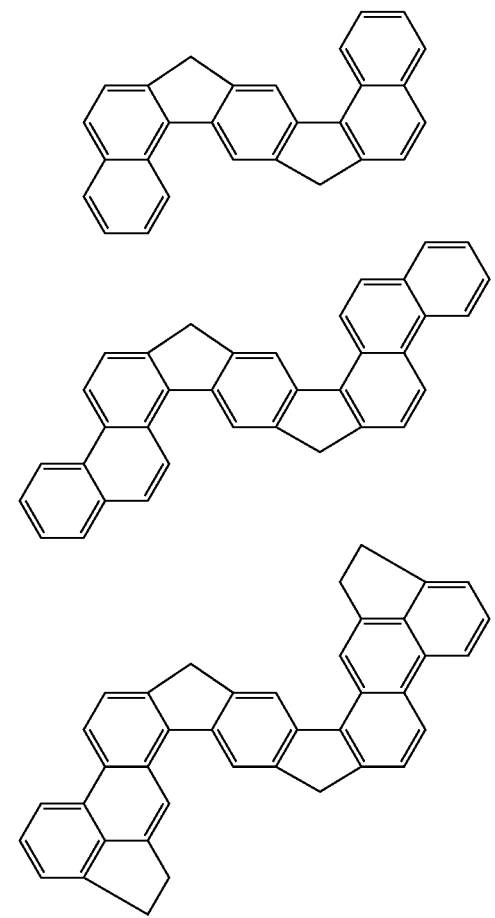

-continued

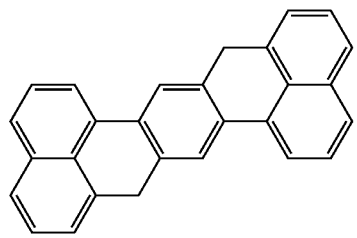

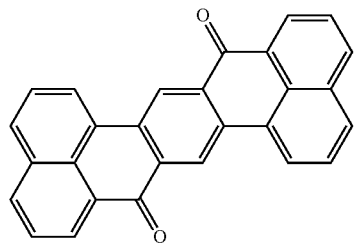

is employed in at least one of the following:
(a) the compound of the formula (1) to formula (4) is employed as host for a fluorescent dopant and/or in that one or more substituents $R^1$ and/or bridges X contain at least one group C=O, P(=O) and/or $SO_2$,
(b) the compound of the formula (1) to formula (4) is employed as matrix for phosphorescent dopants and/or in that one or more substituents $R^1$ contain at least one vinylaryl unit, at least one vinylarylamine unit and/or at least one arylamino unit,
(c) the compounds of the formula (1) to formula (4) are employed as emitting materials and/or in that one or more substituents $R^1$ stand for a group $N(Ar)_2$,
(d) the compound of the formula (1) to formula (4) may optionally be doped with electron-acceptor compounds and in that it is employed in a hole-transport or hole-injection layer, and/or in that one or more substituents $R^1$ contain at least one unit C=O, P(=O) and/or $SO_2$, or
(e) the compound of the formula (1) to formula (4) may optionally be doped with an electron-donor compound and are employed as electron-transport material.

* * * * *